United States Patent
Hahn et al.

(10) Patent No.: US 6,921,770 B2
(45) Date of Patent: Jul. 26, 2005

(54) 2-PHENYLIMINOTHIAZOLINES, THEIR PREPARATION METHOD AND ANTI-RICE BLAST AGENT CONTAINING THE SAME

(75) Inventors: Hoh Gyu Hahn, Seoul (KR); Kee Dal Nam, Seoul (KR); Kee Hyuk Chang, Seoul (KR); Kwang Yun Cho, Taejon (KR); Heung Tae Kim, Taejon (KR)

(73) Assignee: Korea Institute of Science and Technology, Seoul (KR)

( * ) Notice: Subject to any disclaimer, the term of this patent is extended or adjusted under 35 U.S.C. 154(b) by 5 days.

(21) Appl. No.: 10/333,460

(22) PCT Filed: Jul. 28, 2001

(86) PCT No.: PCT/KR01/01289

§ 371 (c)(1),
(2), (4) Date: May 30, 2003

(87) PCT Pub. No.: WO02/13611

PCT Pub. Date: Feb. 21, 2002

(65) Prior Publication Data

US 2003/0203950 A1 Oct. 30, 2003

(30) Foreign Application Priority Data

Jul. 28, 2000 (KR) ......................... 2000/43795

(51) Int. Cl.$^7$ ..................... A61K 31/426; C07D 277/18
(52) U.S. Cl. ....................... 514/370; 548/194
(58) Field of Search ........................ 514/370; 548/194

(56) References Cited

FOREIGN PATENT DOCUMENTS

| JP | 57-183766 | 11/1982 |
|---|---|---|
| KR | 10-0247729 B1 | 12/1999 |

OTHER PUBLICATIONS

Hahn, Hoh–Gyu et al: "Synthesis of new 2–iminothiazolines and their antifungal activities" Han'Guk Nonghwa Hakhoechi (1997), 40(2), 139–143, XP009026106.

Hahn, Hoh–Gyu et al: "Synthesis of new 2–iminothiazolines and their antifungal activities" II Han'Guk Nonghwa Hakhoechi (1998), 41(6), 471–476, XP009026107.

*Primary Examiner*—Taofiq Solola
(74) *Attorney, Agent, or Firm*—Morrison & Foerster LLP

(57) ABSTRACT

2-phenyliminothiazolines of the following formula I, their salts, their preparation method and their use for treating rice blast. The phenyliminothiazolines and their salts of the present invention have low toxicity to environment or living organisms, and exert high activity at low concentration for treating rice blast through a new control mechanism, that is by inhibiting pentaketide synthesis and cyclization of the melanin sythesis process in formula I

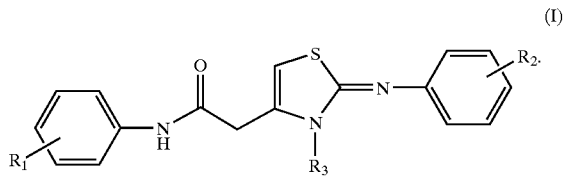

(I)

10 Claims, 2 Drawing Sheets

CK=Untreated control
K5=Compound 5 (5μg/ml)
K5=Tricyclazole (5μg/ml)
KT5=Compound 5+Tricyclazole

2-PHENYLIMINOTHIAZOLINES, THEIR PREPARATION METHOD AND ANTI-RICE BLAST AGENT CONTAINING THE SAME

This Application is a 371 of PCT/KR01/01289 filed Jul. 28, 2001.

TECHNICAL FIELD

The present invention relates to 2-phenyliminothiazoline derivatives and their salts that have powerful antimicrobial activity, their preparation method and their use as fungicides, especially as rice blast fungicides.

BACKGROUND OF THE INVENTION

Generally, an agricultural chemical is a drug that can prevent the infection of the contagious pathogens including bacteria and fungi, prevent the occurrence of the disease even when infected or treat the disease. The agricultural chemical can act by inhibiting the growth or proliferation of the pathogen in some cases. The agricultural chemicals can be divided by the target site and mechanism. Firstly, the drugs containing various metal ions and dithiocarbamates such as Captan act by inhibiting the respiration of cytoplasm or mitochondria, and oxycarboxines act by inhibiting electron transfer system. Secondly, the drugs that inhibit the biosynthesis of the fungi are another kind of agricultural chemicals. For instance, blasticidine-S inhibiting protein biosynthesis, dicarboximides inhibiting biosynthesis of cell wall component chitin of fungi, pyrimidines, triazoles and imidazoles inhibiting steroid biosynthesis of cell membrane, tricyclazoles inhibiting cell membrane triglyceride biosynthesis and acylalanines inhibiting nucleic acid synthesis belong to this category. Thirdly, benomyls inhibit the proliferation by preventing the nuclear division. Fourthly, dodines inhibit the function of the cell membrane by the physical means. And fifthly, fosetyl-Al increases the resistance of the host plant.

One of the differences of *Magnaporthe grisea* that causes rice blast, one of the main rice diseases, is the fact that melanin pigment accumulates between he appressorium cell membrane and cell wall when *Magnaporthe grisee* invades and damages the plant If the pigment cannot accumulate inside the appressorium by preventing the biosynthesis of melanin pigment, this mechanism of action can be used in developing fungicides to prevent rice blast.

The thiazdine derivatives in preventing rice blast have been known. The structures of the representative compounds are shown as Formulas II-1, II-2, II-3, II-4, and II-5 [Swiss patent application number 755,894 (May 7, 1975), German patent 2,619,724(Nov. 18, 1976), U.S. Pat. No. 4,079,144 (Mar. 14, 1978), Japanese Patent Announcement No. 85,054,314 (Nov. 29, 1985), EP 683,160 (1995) (Chem. Abstr. 124:202283j), Fiziol. Akt. Veshchestva (USSR) 1976, 8, 109–112 (Chem. Abstr 87:48807s(1977), Geman Laid-Open Patent Publication No. 3,836,160 (1988) (Chem. Abstr. 113:128074w(1990), Geman Laid-Open Patent Publication No. 3836184 (1988) (Chain. Abstr 113:1 52457u (1990)), Ger (East) DD 241,844 (1985) (Chem. Abstr. 107:91901 m(1 987)).

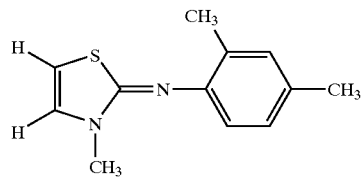

II-1

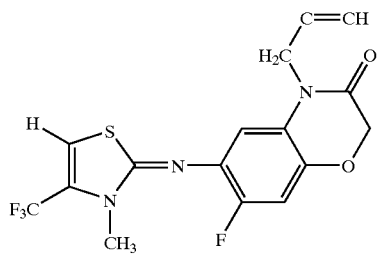

II-2

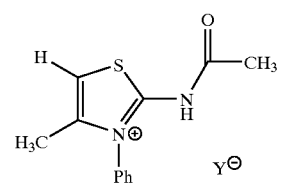

II-3

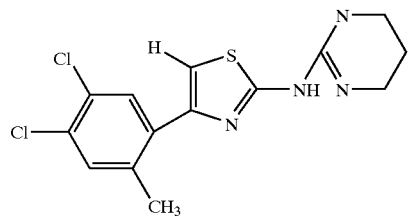

II-4

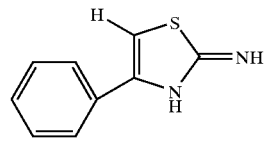

II-5

The problem of these agricultural chemicals including those shown above, however, is that fungus becomes resistant against these chemicals. Therefore, the chemicals become less effective even at higher concentrations. Therefore, to solve these problems, it is necessary to develop chemicals with tally different mechanism of action.

SUMMARY OF THE INVENTION

Therefore, an object of the present invention is to develop compounds to prevent rice blast by different mechanism of action from the conventional fungicides.

Another object of the present invention is to provide a preparation method of the above compounds.

Yet another object of the present invention is to provide a fungicide composition of the above compound as an active ingredient to treat rice blast.

DETAILED DESCRIPTION OF THE PRESENT INVENTION

Figure 1:
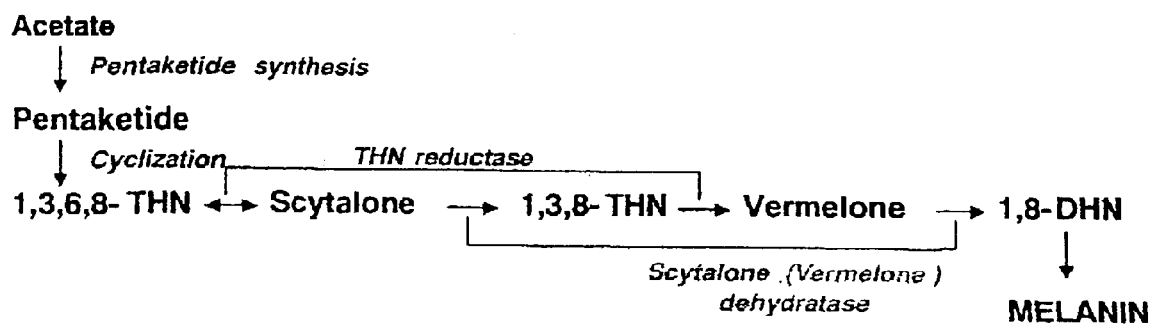
FIG. 1 is a schematic representation of the melanin pigment biosynthesis of *Magnaporthe grisea*.

To achieve the above objects, the present inventors have found that the compound having the following Formula (I) and their salts of the present invention shown below have a selective antifungal activity against rice blast fungi selectively as a result of intensive research in synthesizing the compounds that prevent rice blast with a different mechanism.

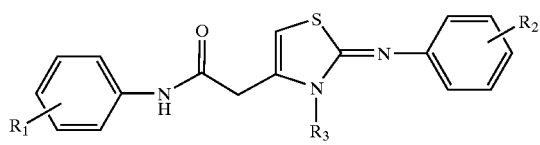

wherein, $R_1$ and $R_2$ each represent a hydrogen, an alkyl group selected from the group consisting of methyl, ethyl, propyl, butyl, pentyl and hexyl, a halide group selected from fluoro, chloro and bromo, an alkoxy group selected from methoxy, ethoxy, propoxy, isopropoxy, butyl, isobutoxy and sec-butoxy, cyano, nitro, trifluoromethyl, trifluoromethoxy, methylthio, phenyl, phenoxy, or an alkoxycarbonyl group selected from methoxycarbonyl, ethoxycarbonyl, propoxycarbonyl and isopropoxycarbonyl, and $R_3$ represents a hydrogen, an alkyl group or cycloalkyl group selected from the group consisting of methyl, ethyl, propyl, isopropyl, cyclopropyl, butyl, pentyl, cyclopentyl, hexyl and cyclohexyl.

In the present invention the salts refers to hydrochloride or hydrobromide.

In other words, 2-iminothiazoline derivatives of the present invention manifest its activity by inhibiting the biosynthesis of melanin. More particularly, melanin is biosynthesized by a series of steps including the cyclization from acetyl-CoA. It is believed that 2-iminothiazoline derivatives of the present invention inhibits pentaketide synthesis and cyclization among the above series of reactions which is vastly different action mechanism from conventionally used agricultural chemicals inhibiting *Magnaporthe grisea*.

The present inventors have synthesized thiazoline compounds and applied a patent (Korean Patent Application 97-82359). In the above patent application, many compounds including specific ones are mentioned. However, the above patent, in all respects, merely mentions the compounds themselves without mentioning which compound has an inhibitory effect. The present inventors have found that the inhibition activity changes dramatically depending on the substituting groups in these compounds and have selected preferable compounds with high inhibition activities by changing the substituting groups.

The compounds which have preferable antifungal activity against *Magnaporthe grisea* in the present invention are those shown in Formula (I) wherein the substituting groups $R_1$ and $R_2$ each represent methyl, ethyl, methoxy, isopropoxy, fluoro, chloro, bromo, trifluoromethyl, trifluoromethoxy or cyano and $R_3$ represents methyl. More preferably, $R_1$ represent p-methyl, p-methoxy or p-ethyl and $R_2$ represent p-cyano or p-fluoro.

2-Phenyliminothiazoline derivatives and their salts, i.e., hydrochloride and hydrobromide represented by Formula (I) of the present invention can be prepared by the following reaction processes as described in detail as below.

Process 1

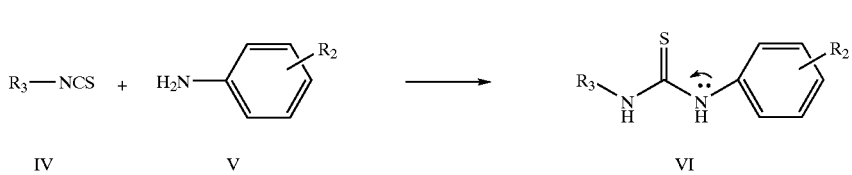

Process 2

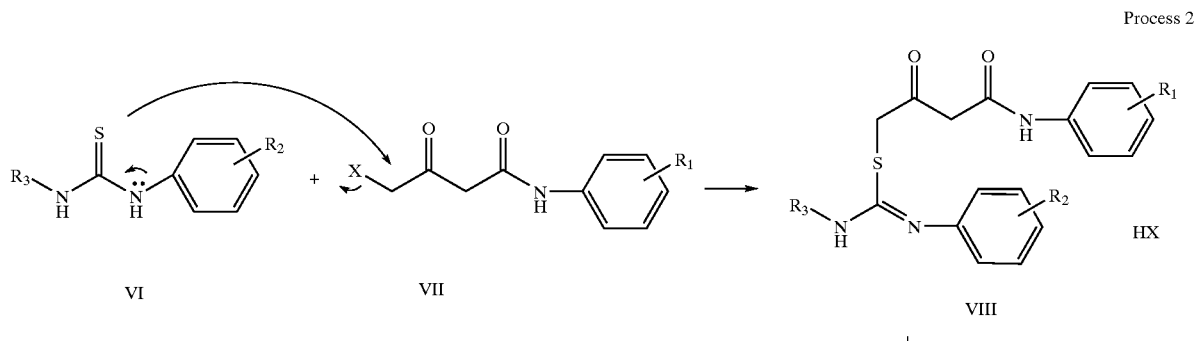

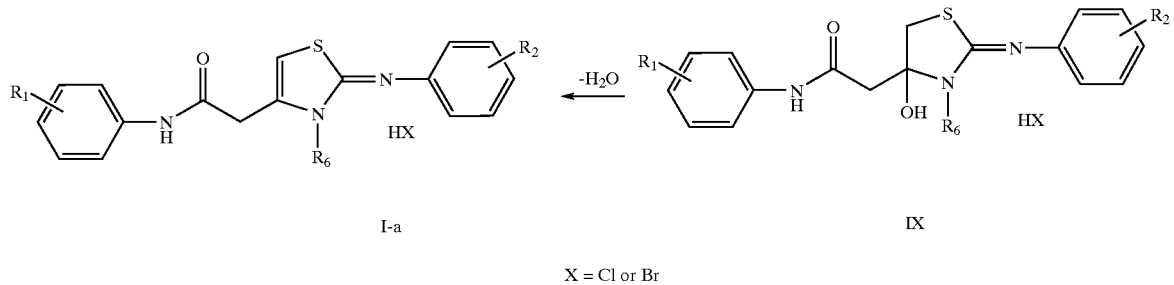

I-a          IX

X = Cl or Br

The above reaction processes can be divided into two steps. [Step 1] is a process to prepare the intermediate, phenylthiourea derivatives represented by Formula (VI) by reacting isothiocyanate derivatives represented by Formula (IV) and phenylamines represented by Formula (V). The reaction can be performed at 0~130° C. and preferably at 20~80° C. The solvents on the reaction can be selected from inactive organic solvents such as acetone, methylene chloride, methanol, chloroform, ethylacetate, ethanol, benzene, isopropanol and toluene. It is economical to use acetone as a solvent since the reaction yield is highest and that there is no need to change the solvent at [Step 2] to prepare Formula (I-a) by reacting Formula (VI) and Formula (VII).

[Step 2] is a process of preparing 2-phenyliminothiazoline hydrochloride or hydrobromide represented by Formula (I-a) after going through a reaction to prepare sulfide compounds represented by Formula (VIII) and a hydroxy intermediate represented by Formula (IX) by reacting phenylthiourea derivatives represented by Formula (VI) and γ-halo-β-keto anilide derivatives represented by Formula (VII). The reaction can be performed at 0~130° C. and preferably at 40~80° C. The solvents on the reaction can be selected from inactive organic solvents such as acetone, methylene chloride, methanol, chloroform, ethylacetate, ethanol, benzene, isopropanol and toluene. It is economical to use acetone as a solvent since it does not have to be changed after [Step 1]. Also it becomes easy to separate 2-phenyliminothiazoline hydrochloride or hydrobromide represented by Formula (I-a) of the present invention produced after the reaction in [Step 2]. [Step 1] and [Step 2] were divided for the sake of convenience to explain the reaction mechanism, but it is not necessary to separate phenylthiourea derivatives represented by Formula (VI) to prepare 2-phenyliminothiazoline derivatives represented by Formula (I-a). The reaction mechanism in [Step 2] can be explained as follows. The intermediate represented by Formula (VIII) is produced by the process that sulfur atom in phenylthiourea derivative represented by Formula (VI) attacks the carbon neighboring the halogen in γ-halo-β-keto anilide derivative represented by Formula (VII). In this process, nitrogen atom neighboring the phenyl group of thiourea derivative participates in the reaction due to its high electron density. Sulfur atom related to the lone paired electrons of the nitrogen atom attacks nucleophilically the carbon neighboring the halogen of γ-halo-β-keto anilide derivative to produce the sulfide intermediate represented by Formula (VIII). Hydroxy intermediate in produced by the attack of the nitrogen atom neighboring $R_3$ of the intermediate sulfide compound represented by Formula (VIII) to carbon of the intramolecular ketone. The hydroxy intermediate represented by Formula (IX) cannot be separated, but dehydrates spontaneously to form 2-phenyliminothiazoline hydrochloride or hydrobromide represented by Formula (I-a). Hydrochloride or hydrobromide, produced from the reaction between the intermediate phenylthiourea derivative represented by Formula (VI) and γ-halo-β-keto anilide derivative represented by Formula (VII), binds with 2-phenyliminothiazoline derivative represented by Formula (I) to produce 2-phenyliminothiazoline derivative represented by Formula (I-a). Hydrochloride or hydrobromide, produced from the reaction between the phenylthiourea derivative represented by Formula (VI) and γ-halo-β-keto anilide derivative represented by Formula (VII), forms a salt with the produced 2-phenyliminothiazoline equivalently, and therefore hydrochloride or hydrobromide does not come out of the reaction solution. Since the solubility of the produced 2-phenyliminothiazoline hydrochloride or hydrobromide is low in the organic solvent such as acetone, they precipitated as solid. Some of 2-phenyliminothiazoline derivatives represented by Formula (I), however, dissolves well in organic solvents and exists as an oily liquid.

In the present invention, 2-phenyliminothiazoline hydrochloride or hydro bromide represented by Formula (I-a) can be treated with inorganic base or organic base to produce 2-phenyliminothiazoline derivative represented by Formula (I) without hydrochloride or hydrobromide. In other words, 2-phenyliminothiazoline hydrochloride or hydrobromide represented by Formula (I-a) can be treated with aqueous solution containing inorganic base such as sodium bicarbonate or sodium hydroxide or organic base such as triethylamine. 2-Phenyliminothiazoline derivatives represented by Formula (I) can be separated easily by extracting with inactive organic solvents such as ethyl acetate, methylene chloride or toluene. To use as agricultural chemical, especially as fungicides in the present invention, it is not necessary to separate hydrochloride or hydrobromide.

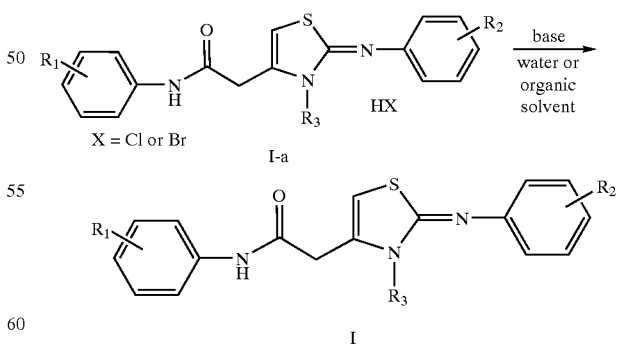

Melting point, characteristics and Yield of 2-phenyliminothiazoline derivatives or their salts represented by Formula (I) or Formula (I-a) of the present invention are summarized in Table 1, but not limited to the examples given.

TABLE 1

| No. | R₁ | R₂ | R₃ | HX | Yield (%) | mp (° C.) |
|---|---|---|---|---|---|---|
| 1 | H | 3-CF₃ | CH₃ | HBr | 82 | 234–235 |
| 2 | H | 4-CF₃ | CH₃ | HBr | 71 | 251–252 |
| 3 | H | 4-OC₆H₅ | CH₃ | HBr | 94 | 249–250 |
| 4 | 4-CH₃ | 3-Cl, 5-Cl | CH₃ | HBr | 85 | 250–251 |
| 5 | H | 3-Cl, 5-Cl | CH₃ | HBr | 86 | 262–263 |
| 6 | 4-CH₃ | 3-CF₃ | CH₃ | HBr | 71 | 199–200 |
| 7 | 3-CF₃ | 3-CF₃ | CH₃ | HBr | 84 | 223–224 |
| 8 | 3-CF₃ | 4-CF₃ | CH₃ | HBr | 76 | 218–219 |
| 9 | 3-CF₃ | 2-CF₃ | CH₃ | HBr | 96 | 197–198 |
| 10 | 3-CF₃ | 3-Cl, 5-Cl | CH₃ | HBr | 81 | 198–199 |
| 11 | 3-CF₃ | 4-OC₆H₅ | CH₃ | HBr | 86 | 229–230 |
| 12 | 3-CF₃ | 3-NO₂ | CH₃ | HBr | 76 | 241–242 |
| 13 | 4-CH₃ | 4-OC₆H₅ | CH₃ | HBr | 87 | 255–256 |
| 14 | 4-CH₃ | 4-CF₃ | CH₃ | HBr | 94 | 263–264 |
| 15 | 4-CH₃ | 3-NO₂ | CH₃ | HBr | 92 | 217 |
| 16 | 4-CH₃ | 4-NO₂ | CH₃ | HBr | 92 | 239 |
| 17 | 3-Cl | 4-OC₆H₅ | CH₃ | HBr | 82 | 240–241 |
| 18 | 3-Cl | 3-NO₂ | CH₃ | HBr | 92 | 238–240 |
| 19 | 3-Cl | 3-CF₃ | CH₃ | HBr | 89 | 253 |
| 20 | 3-Cl | 4-CF₃ | CH₃ | HBr | 93 | 231–232 |
| 21 | 3-Cl | 3-Cl, 5-Cl | CH₃ | HBr | 91 | 291–220 |
| 22 | H | 4-Cl, 3-OCH₂CH=CH(CH₃)₂ | CH₃ | HBr | 75 | 196–197 |
| 23 | H | 4-Cl, 3-CO₂CH(CH₃)₂ | CH₃ | HBr | 89 | 196 |
| 24 | H | 5-Cl, 2-CH₃ | CH₃ | HBr | 83 | 202–204 |
| 25 | H | 4-Cl, 2-CH₃ | CH₃ | HBr | 84 | 225–226 |
| 26 | H | 4-Br, 2-CH₃ | CH₃ | HBr | 86 | 227–229 |
| 27 | H | 2-F, 4-F | CH₃ | HBr | 98 | 240 |
| 28 | 4-CH₃ | 2-OCH₃ | CH₃ | HBr | 99 | 217–218 |
| 29 | 4-CH₃ | 4-OCH₃ | CH₃ | HBr | 90 | 261–262 |
| 30 | 4-CH₃ | 4-(CH₂)₃CH₃ | CH₃ | HBr | 87 | 228–229 |
| 31 | 4-CH₃ | 2-F, 4-F | CH₃ | HBr | 88 | 206–207 |
| 32 | 4-CH₃ | 4-Cl, 2-CH₃ | CH₃ | HBr | 89 | 228–230 |
| 33 | 4-CH₃ | 4-Br, 2-CH₃ | CH₃ | HBr | 91 | 230–231 |
| 34 | 4-CH₃ | 5-Cl, 2-CH₃ | CH₃ | HBr | 99 | 195–196 |
| 35 | 4-CH₃ | 3-Cl, 4-CH₃ | CH₃ | HBr | 91 | 242–244 |
| 36 | 3-CF₃ | 4-OCH₃ | CH₃ | HBr | 71 | 222–224 |
| 37 | H | 4-Cl, 3-CF₃ | CH₃ | HBr | 83 | 214–215 |
| 38 | H | 2-F, 4-NO₂ | CH₃ | HBr | 59 | 240–245 |
| 39 | H | 4-OCF₃ | CH₃ | HBr | 99 | 242–243 |
| 40 | H | 2-Cl, 4-Cl | CH₃ | HBr | 99 | 149–151 |
| 41 | H | 3-Cl, 4-CH₃ | CH₃ | HBr | 85 | 219–221 |
| 42 | H | 4-Cl, 2-F | CH₃ | HBr | 72 | 227–229 |
| 43 | H | 3-Cl, 4-F | CH₃ | HBr | 87 | 217–218 |
| 44 | H | 2-F, 5-CH₃ | CH₃ | HBr | 91 | 214–216 |
| 45 | H | 3-CF₃, 5-CF₃ | CH₃ | HBr | 74 | 209–211 |
| 46 | 4-CH₃ | 4-CN | CH₃ | HBr | 99 | 238–239 |
| 47 | 4-CH₃ | 4-OCF₃ | CH₃ | HBr | 99 | 254–255 |
| 48 | 4-CH₃ | 3-F | CH₃ | HBr | 94 | 240–242 |
| 49 | 4-CH₃ | 2-Cl, 4-Cl | CH₃ | HBr | 86 | 196–198 |
| 50 | 4-CH₃ | 4-Cl, 2-F | CH₃ | HBr | 99 | 206–208 |
| 51 | 4-CH₃ | 3-Cl, 4-F | CH₃ | HBr | 87 | 242–243 |
| 52 | 4-CH₃ | 2-F, 5-CH₃ | CH₃ | HBr | 41 | 186–190 |
| 53 | 4-CH₃ | 4-Cl, 3-CF₃ | CH₃ | HBr | 82 | 230–231 |
| 54 | 4-CH₃ | 3-CF₃, 5-CF₃ | CH₃ | HBr | 94 | 205–206 |
| 55 | 4-CH₃ | 2-F, 4-NO₂ | CH₃ | HBr | 40 | 258–260 |
| 56 | 3-Cl | 4-(CH₂)₃CH₃ | CH₃ | HBr | 39 | 223–224 |
| 57 | 3-Cl | 4-CN | CH₃ | HBr | 58 | 198–200 |
| 58 | 3-Cl | 4-OCF₃ | CH₃ | HBr | 41 | 228 |
| 59 | 3-Cl | 3-F | CH₃ | HBr | 48 | 226 |
| 60 | 3-Cl | 2-Cl, 4-Cl | CH₃ | HBr | 41 | 139–142 |
| 61 | 3-Cl | 4-Cl, 2-CH₃ | CH₃ | HBr | 49 | 219–220 |
| 62 | 3-Cl | 3-Cl, 4-CH₃ | CH₃ | HBr | 49 | 213–215 |
| 63 | 3-Cl | 4-Cl, 2-CH₃ | CH₃ | HBr | 52 | 217–218 |
| 64 | 3-Cl | 3-Cl, 4-F | CH₃ | HBr | 49 | 210–211 |
| 65 | 3-CF₃ | 2-OCH₃ | CH₃ | HBr | 50 | 153–154 |
| 66 | 3-Cl | 4-Cl, 2-F | CH₃ | HBr | 33 | 141–143 |
| 67 | 3-Cl | 2-F, 5-CH₃ | CH₃ | HBr | 31 | 143–144 |
| 68 | 3-Cl | 2-F, 4-F | CH₃ | HBr | 18 | 136 |
| 69 | H | 4-Cl, 2-F, 5-OCH(CH₃)₂ | CH₃ | HBr | 79 | 206–208 |
| 70 | H | 4-Cl, 2-F, 5-OCH₂CH=C(CH₃)₂ | CH₃ | HBr | 72 | 169–177 |
| 71 | H | H | CH₃ | HBr | 97 | 253–254 |
| 72 | 4-OCH₃ | 3-F, 4-CH₃ | CH₃ | HCl | 38 | 241–244 |
| 73 | 2-F | 3-CF₃ | CH₃ | HCl | 61 | 187–193 |
| 74 | 2-F | 2-CH₃, 4-CH₃ | CH₃ | HCl | 77 | 198–205 |
| 75 | 2-F | Cl, 5-Cl | CH₃ | HCl | 80 | 222–224 |
| 76 | 2-F | 3-F | CH₃ | HCl | 75 | 201–202 |
| 77 | 2-F | 4-(CH₂)₃CH₃ | CH₃ | HCl | 97 | 189–195 |

TABLE 1-continued

| No. | R₁ | R₂ | R₃ | HX | Yield (%) | mp (° C.) |
|---|---|---|---|---|---|---|
| 78 | 2-F | 4-OCH₃ | CH₃ | HCl | 93 | 254–255 |
| 79 | 2-F | 4-OCF₃ | CH₃ | HCl | 25 | 200–207 |
| 80 | 2-F | 4-Cl, 2-CH₃ | CH₃ | HCl | 94 | 190–201 |
| 81 | 2-F | 4-Cl, 3-CF₃ | CH₃ | HCl | 80 | 201–204 |
| 82 | 2-F | 4-CN | CH₃ | HCl | 88 | 224–227 |
| 83 | 2-F | 4-CF₃ | CH₃ | HCl | 70 | 215–219 |
| 84 | 2-F | 4-OC₆H₅ | CH₃ | HCl | 97 | 212–215 |
| 85 | 2-F | 4-C₆H₅ | CH₃ | HCl | 65 | 221–222 |
| 86 | 2-F | 3-OCH(CH₃)₂ | CH₃ | HCl | 84 | 184–287 |
| 87 | 2-F | 3-OCH₃ | CH₃ | HCl | 91 | 163–165 |
| 88 | 2-F | 4-Cl | CH₃ | HCl | 51 | 224–226 |
| 89 | 2-F | 2-F | CH₃ | HCl | 99 | 179–183 |
| 90 | 2-F | 3-Cl | CH₃ | HCl | 58 | 171–173 |
| 91 | 2-Cl, 4-Cl, 6-Cl | 4-CN | CH₃ | HCl | 66 | 237–241 |
| 92 | 2-OCF₃ | 4-CN | CH₃ | HCl | 67 | 212–213 |
| 93 | 2-Cl, 4-Cl, 6-Cl | 3-Cl, 5-Cl | CH₃ | HCl | 29 | 218–222 |
| 94 | 4-OCF₃ | 3-Cl, 5-Cl | CH₃ | HCl | 43 | 221 |
| 95 | 4-Cl | 4-CF₃ | CH₃ | HCl | 99 | 215–218 |
| 96 | 2-Cl, 4-Cl, 6-Cl | 4-CF₃ | CH₃ | HCl | 71 | 182–191 |
| 97 | 4-OCF₃ | 4-CF₃ | CH₃ | HCl | 73 | 223–228 |
| 98 | 4-Cl | 4-CF₃ | CH₃ | HCl | 77 | 220–223 |
| 99 | 2-Cl, 4-Cl, 6-Cl | 4-OC₆H₅ | CH₃ | HCl | 85 | 218–220 |
| 100 | 4-OCF₃ | 4-OC₆H₅ | CH₃ | HCl | 94 | 242–246 |
| 101 | 4-OCF₃ | 4-Br | CH₃ | HCl | 48 | 215–218 |
| 102 | 4-OCH₃ | 2-Cl, 5-Cl | CH₃ | HCl | 53 | 215–217 |
| 103 | 2-Cl, 4-Cl, 6-Cl | 2-CH₃, 4-CH₃ | CH₃ | HCl | 59 | 200–204 |
| 104 | 4-OCH₃ | 4-Cl | CH₃ | HCl | 80 | 241–244 |
| 105 | 2-F | 4-OCH(CH₃)₂ | CH₃ | HCl | 30 | 209–212 |
| 106 | 2-F | 4-F | CH₃ | HCl | 48 | 180–188 |
| 107 | 2-F | 3-NO₂ | CH₃ | HCl | 94 | 185–189 |
| 108 | 4-OCF₃ | 4-OCF₃ | CH₃ | HCl | 47 | 236–239 |
| 109 | 4-OCF₃ | 3-OCH(CH₃)₂ | CH₃ | HCl | 73 | 208–210 |
| 110 | 4-OCF₃ | 4-(CH₂)₃CH₃ | CH₃ | HCl | 71 | 240–243 |
| 111 | 4-OCF₃ | 4-NO₂ | CH₃ | HCl | 56 | 178–184 |
| 112 | 4-OCF₃ | 3-OCH₃ | CH₃ | HCl | 77 | 233–236 |
| 113 | 4-OCF₃ | 4-OCH₃ | CH₃ | HCl | 55 | 240–244 |
| 114 | 4-OCF₃ | 4-Cl | CH₃ | HCl | 72 | 224–228 |
| 115 | 4-OCF₃ | 4-F | CH₃ | HCl | 57 | 238–239 |
| 116 | 4-OCF₃ | 4-C₆H₅ | CH₃ | HCl | 66 | 232–233 |
| 117 | 4-OCF₃ | 3-CF₃ | CH₃ | HCl | 43 | 201–204 |
| 118 | 4-Cl | 4-OCH₃ | CH₃ | HCl | 44 | 250–253 |
| 119 | 4-Cl | 3-OCH₃ | CH₃ | HCl | 74 | 228–231 |
| 120 | 4-Cl | 4-OC₆H₅ | CH₃ | HCl | 38 | 238–242 |
| 121 | 4-Cl | 4-OCF₃ | CH₃ | HCl | 20 | 237–240 |
| 122 | 4-Cl | 4-Cl | CH₃ | HCl | 90 | 239–242 |
| 123 | 4-Cl | 3-OCH(CH₃)₂ | CH₃ | HCl | 65 | 201–203 |
| 124 | 4-Cl | 4-(CH₂)₃CH₃ | CH₃ | HCl | 59 | 239–241 |
| 125 | 4-Cl | 3-NO₂ | CH₃ | HCl | 26 | 228 |
| 126 | 4-Cl | 3-CF₃ | CH₃ | HCl | 63 | 204–207 |
| 127 | 4-Cl | 4-NO₂ | CH₃ | HCl | 78 | 202–205 |
| 128 | 4-Cl | 4-CN | CH₃ | HCl | 75 | 222–225 |
| 129 | 4-Cl | 3-F | CH₃ | HCl | 47 | 234–236 |
| 130 | 4-Cl | 4-Br | CH₃ | HCl | 71 | 228–235 |
| 131 | 4-Cl | 4-C₆H₅ | CH₃ | HCl | 64 | 238–241 |
| 132 | 4-Br | 4-CF₃ | CH₃ | HCl | 37 | 220–223 |
| 133 | 4-Br | 2-F, 4-F | CH₃ | HCl | 40 | 207–209 |
| 134 | 4-Br | 3-Cl, 2-F | CH₃ | HCl | 34 | 217–227 |
| 135 | 4-Br | 2-CH₃, 4-CH₃ | CH₃ | HCl | 70 | 205–207 |
| 136 | 4-Br | 4-F | CH₃ | HCl | 55 | 230–237 |
| 137 | 4-Br | 3-Br | CH₃ | HCl | 34 | 218–229 |
| 138 | 4-Br | 3-Cl, 5-Cl | CH₃ | HCl | 42 | 227 |
| 139 | 4-Br | 4-OCF₃ | CH₃ | HCl | 43 | 235 |
| 140 | 4-Br | 2-Cl, 4-F | CH₃ | HCl | 57 | 218 |
| 141 | 4-Br | 4-OC₆H₅ | CH₃ | HCl | 76 | 232–235 |
| 142 | 4-Br | 4-Br, 2-CH₃ | CH₃ | HCl | 79 | 219–221 |
| 143 | 4-Br | 4-Br | CH₃ | HCl | 41 | 239 |
| 144 | 4-Br | 4-NO₂ | CH₃ | HCl | 28 | 214–223 |
| 145 | 4-Br | 2-OCH₃, 5-CH₃ | CH₃ | HCl | 57 | 205–208 |
| 146 | 4-Br | 3-F | CH₃ | HCl | 49 | 234–235 |
| 147 | 4-Br | 4-(CH₂)₃CH₃ | CH₃ | HCl | 46 | 238–240 |
| 148 | 4-Br | 2-F | CH₃ | HCl | 49 | 188–192 |
| 149 | 2-F | 3-Cl, 4-F | CH₃ | HCl | 44 | 195–201 |
| 150 | 2-F | 4-Cl, 2-F | CH₃ | HCl | 30 | 183–186 |
| 151 | 2-F | 4-Cl, 2-F, 5-OCH(CH₃)₂ | CH₃ | HCl | 46 | 177–179 |
| 152 | 2-F | 4-Br | CH₃ | HCl | 31 | 229–230 |
| 153 | 2-F | 3-Br | CH₃ | HCl | 41 | 169–174 |
| 154 | 4-Cl | 2-CH₃, 4-CH₃ | CH₃ | HCl | 86 | 219–221 |

TABLE 1-continued

| No. | R₁ | R₂ | R₃ | HX | Yield (%) | mp (° C.) |
|---|---|---|---|---|---|---|
| 155 | 4-Cl | 3-Cl, 4-F | CH₃ | HCl | 67 | 211–213 |
| 156 | 4-Cl | 3-Br | CH₃ | HCl | 49 | 226–229 |
| 157 | 4-Cl | 2-OCH₃, 5-CH₃ | CH₃ | HCl | 59 | 205–208 |
| 158 | 4-Cl | 4-Cl, 2-F | CH₃ | HCl | 30 | 211–214 |
| 159 | 4-Cl | 2-F, 4-F | CH₃ | HCl | 36 | 205–207 |
| 160 | 4-Cl | 2-F | CH₃ | HCl | 66 | 199–204 |
| 161 | 4-Cl | 4-Cl, 2-F, 5-OCH(CH₃)₂ | CH₃ | HCl | 40 | 198–204 |
| 162 | 4-CH₃ | 4-Br | CH₃ | HCl | 37 | 241–248 |
| 163 | 4-CH₃ | 4-F | CH₃ | HCl | 78 | 246–248 |
| 164 | 4-CH₃ | 4-Cl | CH₃ | HCl | 65 | 248–252 |
| 165 | 4-CH₃ | 2-CH₃, 4-CH₃ | CH₃ | HCl | 76 | 214–216 |
| 166 | 4-CH₃ | 2-OCH₃, 5-CH₃ | CH₃ | HCl | 48 | 207–210 |
| 167 | 4-CH₃ | 2-F | CH₃ | HCl | 54 | 178–180 |
| 168 | 4-CH₃ | 4-Cl, 2-F, 5-OCH(CH₃)₂ | CH₃ | HCl | 39 | 195–198 |
| 169 | 4-NO₂ | 4-CN | CH₃ | HCl | 37 | 250–252 |
| 170 | 4-NO₂ | 2-F, 4-F | CH₃ | HCl | 56 | 245–247 |
| 171 | 4-NO₂ | 4-Br | CH₃ | HCl | 48 | 240–241 |
| 172 | 4-NO₂ | 4-CF₃ | CH₃ | HCl | 58 | 252–254 |
| 173 | 4-NO₂ | 3-Cl, 5-Cl | CH₃ | HCl | 37 | 235–239 |
| 174 | 4-NO₂ | 4-OC₆H₅ | CH₃ | HCl | 55 | 228–229 |
| 175 | 4-NO₂ | 2-CH₃, 4-CH₃ | CH₃ | HCl | 70 | 204–207 |
| 176 | 4-NO₂ | 4-OCF₃ | CH₃ | HCl | 49 | 229–230 |
| 177 | 4-NO₂ | 4-F | CH₃ | HCl | 61 | 257 |
| 178 | 4-NO₂ | 3-F | CH₃ | HCl | 65 | 224–229 |
| 179 | 4-NO₂ | 4-Cl | CH₃ | HCl | 73 | 247 |
| 180 | 4-NO₂ | 3-Cl, 4-F | CH₃ | HCl | 60 | 239 |
| 181 | 4-NO₂ | 4-(CH₂)₃CH₃ | CH₃ | HCl | 60 | 242 |
| 182 | 4-NO₂ | 2-OCH₃, 5-CH₃ | CH₃ | HCl | 59 | 227–229 |
| 183 | 4-NO₂ | 4-Cl, 2-F, 5-OCH(CH₃)₂ | CH₃ | HCl | 57 | 225–227 |
| 184 | 4-NO₂ | 2-F | CH₃ | HCl | 63 | 238–239 |
| 185 | 4-Br | 4-Cl, 2-F, 5-OCH(CH₃)₂ | CH₃ | HCl | 85 | 201–205 |
| 186 | 4-OCF₃ | 2-CH₃, 4-CH₃ | CH₃ | HCl | 88 | 203–207 |
| 187 | 4-OCF₃ | 4-Br | CH₃ | HCl | 39 | 205–208 |
| 188 | 4-OCF₃ | 3-Cl, 4-F | CH₃ | HCl | 38 | 217–218 |
| 189 | 4-OCF₃ | 3-F | CH₃ | HCl | 42 | 225–227 |
| 190 | 4-OCF₃ | 4-CF₃ | CH₃ | HCl | 38 | 217–219 |
| 191 | 4-OCF₃ | 3-Br | CH₃ | HCl | 57 | 220–224 |
| 192 | 4-OCF₃ | 2-F, 4-F | CH₃ | HCl | 58 | 205–209 |
| 193 | 4-OCF₃ | 2-OCH₃, 5-CH₃ | CH₃ | HCl | 76 | 199–204 |
| 194 | 4-OCF₃ | 4-Cl, 2-F, 5-OCH(CH₃)₂ | CH₃ | HCl | 50 | 200–203 |
| 195 | 4-OCF₃ | 4-Cl, 2-F | CH₃ | HCl | 98 | 201–208 |
| 196 | 4-OCH₃ | 2-CH₃, 4-CH₃ | CH₃ | HCl | 76 | 170–174 |
| 197 | 4-OCH₃ | 4-(CH₂)₃CH₃ | CH₃ | HCl | 60 | 230–232 |
| 198 | 4-OCH₃ | 2-OCH₃, 5-CH₃ | CH₃ | HCl | 44 | 180–184 |
| 199 | 4-OC₆H₅ | 2-CH₃, 4-CH₃ | CH₃ | HCl | 73 | 184–187 |
| 200 | 4-OC₆H₅ | 2-OCH₃, 5-CH₃ | CH₃ | HCl | 53 | 198–203 |
| 201 | 4-OCH₃ | 3-Br | CH₃ | HCl | 50 | 223–225 |
| 202 | 4-OCH₃ | 3-Cl, 4-F | CH₃ | HCl | 37 | 224–231 |
| 203 | 4-OCH₃ | 3-F | CH₃ | HCl | 35 | 228–232 |
| 204 | 4-OCH₃ | 2-F | CH₃ | HCl | 68 | 190–195 |
| 205 | 4-OCH₃ | 4-CF₃ | CH₃ | HCl | 39 | 226–232 |
| 206 | 4-OCH₃ | 2-F, 4-F | CH₃ | HCl | 49 | 178–182 |
| 207 | 4-OCH₃ | 4-Cl, 2-F | CH₃ | HCl | 37 | 201–205 |
| 208 | 4-OCH₃ | 4-Cl, 2-F, 5-OCH(CH₃)₂ | CH₃ | HCl | 34 | 212–216 |
| 209 | 4-OCH₃ | 4-OCF₃ | CH₃ | HCl | 24 | 232–236 |
| 210 | 4-CN | 3-F | CH₃ | HCl | 59 | 216–219 |
| 211 | 4-CN | 4-F | CH₃ | HCl | 57 | 239–240 |
| 212 | 4-CN | 2-F | CH₃ | HCl | 60 | 214–219 |
| 213 | 4-CN | 4-CN | CH₃ | HCl | 35 | 238 |
| 214 | 4-CN | 4-Br | CH₃ | HCl | 49 | 239 |
| 215 | 4-CN | 4-OCF₃ | CH₃ | HCl | 54 | 196–199 |
| 216 | 4-CN | 4-Cl | CH₃ | HCl | 48 | 245–246 |
| 217 | 4-CN | 3-Cl, 5-Cl | CH₃ | HCl | 38 | 249–250 |
| 218 | 4-CN | 4-OC₆H₅ | CH₃ | HCl | 56 | 213–216 |
| 219 | 4-CN | 2-CH₃, 4-CH₃ | CH₃ | HCl | 79 | 216–221 |
| 220 | 4-CN | 3-Cl, 4-F | CH₃ | HCl | 50 | 221–225 |
| 221 | 4-CN | 4-(CH₂)₃CH₃ | CH₃ | HCl | 42 | 245–248 |
| 222 | 4-CN | 3-Br | CH₃ | HCl | 36 | 234–238 |
| 223 | 4-CN | 4-Cl, 2-F | CH₃ | HCl | 33 | 217–222 |
| 224 | 4-CN | 2-OCH₃, 5-CH₃ | CH₃ | HCl | 83 | 217–219 |
| 225 | 4-CN | 2-F, 4-F | CH₃ | HCl | 39 | 239–240 |
| 226 | 4-CN | 4-Cl, 2-F, 5-OCH(CH₃)₂ | CH₃ | HCl | 84 | 231–244 |
| 227 | 3-Cl, 4-CH₃ | 2-CH₃, 4-CH₃ | CH₃ | HCl | 88 | 194–196 |
| 228 | 3-Cl, 4-CH₃ | 4-CN | CH₃ | HCl | 64 | 230–234 |
| 229 | 3-Cl, 4-CH₃ | 4-Br | CH₃ | HCl | 58 | 252–254 |
| 230 | 3-Cl, 4-CH₃ | 3-Cl, 5-Cl | CH₃ | HCl | 63 | 216–221 |
| 231 | 3-Cl, 4-CH₃ | 4-OCF₃ | CH₃ | HCl | 58 | 236–240 |

TABLE 1-continued

| No. | $R_1$ | $R_2$ | $R_3$ | HX | Yield (%) | mp (° C.) |
|---|---|---|---|---|---|---|
| 232 | 3-Cl, 4-CH$_3$ | 2-F, 4-F | CH$_3$ | HCl | 69 | 217–220 |
| 233 | 3-Cl, 4-CH$_3$ | 4-Cl | CH$_3$ | HCl | 68 | 244–245 |
| 234 | 3-Cl, 4-CH$_3$ | 4-(CH$_2$)$_3$CH$_3$ | CH$_3$ | HCl | 77 | 234–236 |
| 235 | 3-Cl, 4-CH$_3$ | 2-F | CH$_3$ | HCl | 51 | 196–199 |
| 236 | 3-Cl, 4-CH$_3$ | 3-F | CH$_3$ | HCl | 65 | 228 |
| 237 | 3-Cl, 4-CH$_3$ | 4-F | CH$_3$ | HCl | 89 | 239–242 |
| 238 | 3-Cl, 4-CH$_3$ | 3-Cl, 4-F | CH$_3$ | HCl | 58 | 229–231 |
| 239 | 3-Cl, 4-CH$_3$ | 2-OCH$_3$, 5-CH$_3$ | CH$_3$ | HCl | 40 | 190–195 |
| 240 | 3-Cl, 4-CH$_3$ | 4-OC$_6$H$_5$ | CH$_3$ | HCl | 79 | 237–243 |
| 241 | 4-OC$_6$H$_5$ | 4-Cl, 2-F | CH$_3$ | HCl | 55 | 208–210 |
| 242 | 4-OC$_6$H$_5$ | 4-F | CH$_3$ | HCl | 42 | 234–238 |
| 243 | 4-OC$_6$H$_5$ | 3-F | CH$_3$ | HCl | 49 | 214–217 |
| 244 | 4-OC$_6$H$_5$ | 2-F, 4-F | CH$_3$ | HCl | 43 | 202–205 |
| 245 | 4-OC$_6$H$_5$ | 2-F | CH$_3$ | HCl | 43 | 187–191 |
| 246 | 4-OC$_6$H$_5$ | 3-Br | CH$_3$ | HCl | 40 | 196–201 |
| 247 | 4-OC$_6$H$_5$ | 3-Cl, 4-F | CH$_3$ | HCl | 37 | 221–225 |
| 248 | 4-OC$_6$H$_5$ | 3-Cl, 5-Cl | CH$_3$ | HCl | 20 | 219–223 |
| 249 | 4-OC$_6$H$_5$ | 4-Cl | CH$_3$ | HCl | 47 | 242–246 |
| 250 | 4-OC$_6$H$_5$ | 4-(CH$_2$)$_3$CH$_3$ | CH$_3$ | HCl | 66 | 231–235 |
| 251 | 4-OC$_6$H$_5$ | 4-OCF$_3$ | CH$_3$ | HCl | 41 | 236–240 |
| 252 | 4-OC$_6$H$_5$ | 4-Br | CH$_3$ | HCl | 38 | 243–247 |
| 253 | 4-OC$_6$H$_5$ | 4-Cl, 2-F, 5-OCH(CH$_3$)$_2$ | CH$_3$ | HCl | 25 | 211–217 |
| 254 | 4-OC$_6$H$_5$ | 4-CN | CH$_3$ | HCl | 19 | 208–212 |
| 255 | 4-OC$_6$H$_5$ | 4-OC$_6$H$_5$ | CH$_3$ | HCl | 52 | 232–237 |
| 256 | 4-OC$_6$H$_5$ | 4-CF$_3$ | CH$_3$ | HCl | 28 | 231–234 |
| 257 | 3-Cl, 4-CH$_3$ | 4-Cl, 2-F, 5-OCH(CH$_3$)$_2$ | CH$_3$ | HCl | 62 | 157–161 |
| 258 | 4-Br | 2-F, 4-F | cyclopropyl | HCl | 50 | 194–196 |
| 259 | 4-Br | 4-OC$_6$H$_5$ | cyclopropyl | HCl | 74 | 199–215 |
| 260 | 4-Br | 4-CN | cyclopropyl | HCl | 13 | 231–245 |
| 261 | 4-Br | 3-F | cyclopropyl | HCl | 71 | 242–245 |
| 262 | 4-Br | H | cyclopropyl | HCl | 86 | 231–236 |
| 263 | 4-Br | 2-CH$_3$, 4-CH$_3$ | cyclopropyl | HCl | 76 | 218–221 |
| 264 | H | 3-CF$_3$ | CH(CH$_3$)$_2$ | HBr | 20 | 136–142 |
| 265 | H | 2-CH$_3$, 4-CH$_3$ | cyclohexyl | HBr | | |
| 266 | 4-F | 2-CH$_3$, 4-CH$_3$ | CH$_2$CH$_2$C$_6$H$_5$ | HBr | | |
| 267 | H | 2-CH$_3$, 5-CH$_3$ | CH$_2$CH=CH$_2$ | HBr | | |
| 268 | 4-F | 2-CH$_3$, 4-CH$_3$ | CH$_2$CH=CH$_2$ | HBr | | |
| 269 | H | 4-Cl, 2-CH$_3$ | CH$_3$ | HBr | 82 | 230–232 |
| 270 | H | 2-CH$_3$, 4-CH$_3$ | CH$_3$ | HBr | 91 | 182–184 |
| 271 | H | 3-CN | CH$_3$ | HBr | 31 | 227 |
| 272 | 4-F | 2-F, 4-F | CH$_3$ | HBr | 54 | 231–232 |
| 273 | H | 4-CH$_3$ | CH$_3$ | HBr | 68 | 247 |
| 274 | H | 2-CH$_3$ | CH$_3$ | HBr | 89 | 179–181 |
| 275 | H | 3-CH$_3$ | CH$_3$ | HBr | 93 | 194–195 |
| 276 | H | 4-F | CH$_3$ | HBr | 94 | 238 |
| 277 | H | 2-F | CH$_3$ | HBr | 96 | 192–194 |
| 278 | H | 3-F | CH$_3$ | HBr | 95 | 215–216 |
| 279 | H | 2-OCH$_3$ | CH$_3$ | HBr | 96 | 208–210 |
| 280 | H | 4-OCH$_3$ | CH$_3$ | HBr | 99 | 112 |
| 281 | H | 2-C$_6$H$_5$ | CH$_3$ | HBr | 86 | 209–211 |
| 282 | H | 4-C$_6$H$_5$ | CH$_3$ | HBr | 90 | 254 |
| 283 | H | 4-Cl | CH$_3$ | HBr | 93 | 247 |
| 284 | H | 3-Cl | CH$_3$ | HBr | 93 | 210 |
| 285 | H | 2-Cl | CH$_3$ | HBr | 89 | 188–190 |
| 286 | H | 4-CH$_2$CH$_3$ | CH$_3$ | HBr | 99 | 119 (dec) |
| 287 | H | 4-Br | CH$_3$ | HBr | 99 | 225–227 |
| 288 | H | 3-SCH$_3$ | CH$_3$ | HBr | 93 | 119–200 |
| 289 | H | 3-NO$_2$ | CH$_3$ | HBr | 95 | 232 |
| 290 | H | 4-OCH(CH$_3$)$_2$ | CH$_3$ | HBr | 99 | 119 (dec) |
| 291 | H | 3-OCH(CH$_3$)$_2$ | CH$_3$ | HBr | 93 | 178–180 |
| 292 | H | 4-NO$_2$ | CH$_3$ | HBr | 42 | 156 |
| 293 | H | 4-tert-butyl | CH$_3$ | HBr | 88 | 232–234 |
| 294 | H | 2-tert-butyl | CH$_3$ | HBr | 96 | 239–241 |
| 295 | H | 2-CH(CH$_3$)$_2$ | CH$_3$ | HBr | 90 | 214–215 |
| 296 | H | 3-CH(CH$_3$)$_2$ | CH$_3$ | HBr | 91 | 213–215 |
| 297 | H | 4-CH(CH$_3$)$_2$ | CH$_3$ | HBr | 93 | 241–242 |
| 298 | H | 4-(CH$_2$)$_3$CH$_3$ | CH$_3$ | HBr | 94 | 216–218 |
| 299 | H | 3-OC$_6$H$_5$ | CH$_3$ | HBr | 88 | 212–214 |
| 300 | H | 2-OC$_6$H$_5$ | CH$_3$ | HBr | 18 | 218 |
| 301 | H | 3-CN | CH$_3$ | HBr | 88 | 237 |
| 302 | H | 4-CN | CH$_3$ | HBr | 94 | 199–200 |
| 303 | 4-Cl | 3-OCH(CH$_3$)$_2$ | CH$_3$ | HBr | 67 | 226 |
| 304 | 4-Cl | 4-CH$_2$CH$_3$ | CH$_3$ | HBr | 54 | 202 |
| 305 | 4-Cl | H | CH$_3$ | HBr | 15 | 226 |
| 306 | 4-OCH$_3$ | H | CH$_3$ | HBr | 99 | 230 |
| 307 | 4-OCH$_3$ | 4-OCH$_3$ | CH$_3$ | HBr | 18 | 250 |
| 308 | 4-Cl | 4-OCH$_3$ | CH$_3$ | HBr | 87 | 240 |

TABLE 1-continued

| No. | R₁ | R₂ | R₃ | HX | Yield (%) | mp (° C.) |
|---|---|---|---|---|---|---|
| 309 | 4-OCH₃ | 4-CH₃ | CH₃ | HBr | 100 | 241 |
| 310 | 4-Cl | 2-CH₃ | CH₃ | HBr | 33 | 217 |
| 311 | 4-OCH₃ | 2-OCH₃ | CH₃ | HBr | 94 | 257 |
| 312 | 4-OCH₃ | 2-CH₃ | CH₃ | HBr | 25 | 247 |
| 313 | 4-OCH₃ | 4-OCH(CH₃)₂ | CH₃ | HBr | 90 | 247 |
| 314 | 4-Cl | 4-OCH(CH₃)₂ | CH₃ | HBr | 23 | 229 |
| 315 | 4-OCH₃ | 4-F | CH₃ | HBr | 99 | 240 |
| 316 | 4-Cl | 4-F | CH₃ | HBr | 91 | 234 |
| 317 | 4-Cl | 4-Br | CH₃ | HBr | 74 | 229 |
| 318 | 4-OCH₃ | 4-Br | CH₃ | HBr | 92 | 230 |
| 319 | 4-Cl | 4-O6H₅ | CH₃ | HBr | 89 | 229 |
| 320 | 4-OCH₃ | 4-O6H₅ | CH₃ | HBr | 79 | 228 |
| 321 | H | 2-CH₃, 4-CH₃, 6-CH₃ | CH₃ | HBr | 93 | 243 |
| 322 | 4-Cl | 4-CN | CH₃ | HBr | 80 | 241 |
| 323 | 4-OCH₃ | 4-CN | CH₃ | HBr | 88 | 213–215 |
| 324 | 2-CH₃ | 4-CN | CH₃ | HBr | 72 | 127 |
| 325 | H | 3-Cl, 4-Cl | CH₃ | HBr | 87 | 248 |
| 326 | 4-OCH₃ | 4-t-butyl | CH₃ | HBr | 83 | 210 |
| 327 | 2-OCH₃ | 4-t-butyl | CH₃ | HBr | 65 | 212 |
| 328 | 2-OCH₃ | 3-CH₃ | CH₃ | HBr | 20 | 214 |
| 329 | 4-Cl | 4-CN | CH₃ | — | 64 | 210–212 |
| 330 | 4-OCH₃ | 4-CN | CH₃ | — | 72 | 225–256 |
| 331 | H | 2-F, 4-F | CH₃ | — | 71 | 214–215 |
| 332 | 4-CH₃ | 2-F, 4-F | CH₃ | — | 59 | 183–184 |
| 333 | 4-CH₃ | 4-Cl, 2-F, 5-OCH(CH₃)₂ | CH₃ | — | 63 | 172–173 |
| 334 | 4-OCH₃ | 4-(CH₂)₃CH₃ | CH₃ | — | 67 | 141–142 |
| 335 | 4-OCH₃ | 3-Br | CH₃ | — | 70 | 173–174 |
| 336 | 4-OCH₃ | 4-Br, 5-Cl | CH₃ | — | 73 | 165–166 |
| 337 | 4-OCH₃ | 3-F | CH₃ | — | 72 | 182–184 |
| 338 | 4-OCH₃ | 2-F | CH₃ | — | 69 | 183–185 |
| 339 | 4-OCH₃ | 4-CF₃ | CH₃ | — | 61 | 180–183 |
| 340 | 4-OCH₃ | 2-F, 4-F | CH₃ | — | 74 | 200–202 |
| 341 | 4-CH₂CH₃ | 4-CN | CH₃ | Hal | 52 | 226~229 |
| 342 | 4-CH₃ | 4-Cl, 2-F, 5-OCH(CH₃)₂ | CH₃ | HCl | 39 | 194.7~198.2 |
| 343 | 3-F, 4-OCH₃ | 4-CF₃ | CH₃ | HCl | 23 | 228 |
| 344 | 3-F, 4-OCH₃ | 4-CN | CH₃ | HCl | 23 | 233~234 |
| 345 | 4-CH₂CH₃ | 4-CN | CH₃ | — | 81 | 243 |
| 346 | 4-CH₂CH₃ | 4-OCF₃ | CH₃ | HCl | 67 | 258~260 |

The following figures and examples will serve to further illustrate the preparation method of the compounds of the present invention summarized in the above Table 1 and their reaction mechanism, but not limited to the examples given. Representative Method of Preparation 1: Preparation of 2-phenylimino-3-methyl-4-(N-phenylcarbamoylmethyl)-1,3-thiazol-4-ine hydrobromide ($R_1$=H, $R_2$=H, $R_3$=CH₃, HX=HBr)
After dissolving 0.2 moles of aniline in 50 ml acetone and slowing adding 0.2 moles methylisothiocyanate, the solution was stirred for 15 hours at room temperature. The produced thiourea derivative (CH₃NHCSNHC₆H₅) precipitate was filtered to obtain the white powder. After suspending the produced white powder in 30 ml of acetone and adding 0.2 moles of 4-bromo-3-oxo-N-phenylbutane amide (BrCH₂COCH₂CONHC₆H₅), the suspension was refluxed for 24 hours. The produced solid was filters and air-dried to obtain 2-phenylimino-3-methyl-4-(N-phenylcarbamoylmethyl)-1,3-thiazol-4-ine hydrobromide ($R_1$=H, $R_2$=H, $R_3$=CH₃, HX=HBr).
In below, the starting material, the yield of the reaction product, and the physical properties such as melting point, proton nuclear magnetic resonance (¹H NMR) data are shown in the preparation of 2-iminothiazoline derivatives of Formula (I).

[Compound 1]
2-(3-trifluoromethylphenylimino)-3-methyl-4-(N-phenylcarbamoylmethyl)-1,3-thiazol-4-ine hydrobromide (R1=H, $R_2$=3-CF₃, $R_3$=CH₃, HX=HBr).
Starting materials: methylisothiocyanate, 3-trifluoromethylaniline, 4-bromo-3-oxo-N-phenylbutane amide
Yield: 82% Melting point: 234–235° C. ¹H NMR (DMSO-d₆) δ 3.69 (s, 3H, 3-CH₃), 4.02 (s, 2H, 4-CH₂), 6.97 (s, 1H, 5-vinyl H), 7.08~7.83 (m, 9H, ArH), 10.42 (s, 1H, NH).

[Compound 2]
2-(4-trifluoromethylphenylimino)-3-methyl-4-(N-phenylcarbamoylmethyl)-1,3-thiazol-4-ine hydrobromide (R1=H, $R_2$=4-CF₃, $R_3$=CH₃, HX=HBr).
Starting materials: methylisothiocyanate, 4-trifluoromethylaniline, 4-bromo-3-oxo-N-phenylbutane amide
Yield: 71% Melting point: 251–252° C. ¹H NMR (DMSO-d₆) δ 3.62 (s, 3H, 3-CH₃), 3.96 (s, 2H, 4-CH₂), 6.85 (s, 1H, 5-vinyl H), 7.07~7.85 (m, 9H, ArH), 10.35 (s, 1H, NH); IR(KBr) 3435 (NH), 1664 (C=O) cm⁻¹.

[Compound 3]
2-(4-phenoxyphenylimino)-3-methyl-4-(N-phenylcarbamoylmethyl)-1,3-thiazol-4-ine hydrobromide (R1=H, $R_2$=OC₆H₅, $R_3$=CH₃, HX=HBr).
Starting materials: methylisothiocyanate, 4-phenoxyaniline, 4-bromo-3-oxo-N-phenylbutane amide
Yield: 94% Melting point: 249–250° C. ¹H NMR (DMSO-d₆) δ 3.70 (s, 3H, 3-CH₃), 4.02 (s, 2H, 4-CH₂), 7.01 (s, 1H, 5-vinyl H), 7.08~7.62 (m, 14H, ArH), 10.42 (s, 1H, NH); IR(KBr) 3424 (NH), 1662 (C=O) cm⁻¹.

[Compound 4]
2-(3,5-dichlorophenylimino)-3-methyl-4-[N-(4-methylphenyl)carbamoylmethyl]-1,3-thiazol-4-ine hydrobromide (R1=CH₃, $R_2$=3-Cl, 5-Cl, $R_3$=CH₃, HX=HBr).
Starting materials: methylisothiocyanate, 3,5-dichloroaniline, 4-bromo-3-oxo-N-(4-methylphenyl)butane amide Yield: 85% Melting point: 250–251° C. $^1$H NMR (DMSO-d$_6$) δ 2.25 (s, 3H, ArCH$_3$), 3.53 (s, 3H, 3-CH$_3$), 3.89 (s, 2H, 4-CH$_2$), 6.70 (s, 1H, 5-vinyl H), 7.11~7.49 (m, 7H, ArH), 10.24 (s, 1H, NH); IR(KBr) 3425 (NH), 1656 (C=O) cm$^{-1}$.

[Compound 5]
2-(3,5-dichlorophenylimino)-3-methyl-4-(N-phenylcarbamoylmethyl)-1,3-thiazol-4-ine hydrobromide (R1=H, R$_2$=3-Cl, 5-Cl, R$_3$=CH$_3$, HX=HBr).

Starting materials: methylisothiocyanate, 3,5-dichloroaniline, 4-bromo-3oxo-N-phenylbutane amide Yield: 86% Melting point: 262–263° C. $^1$H NMR (DMSO-d$_6$) δ 3.57 (s, 3H, 3-CH$_3$), 3.94 (s, 2H, 4-CH$_2$), 6.79 (s, 1H, 5-vinyl H), 7.05~7.62 (m, 9H, ArH), 10.37 (s, 1H, NH); IR(KBr) 3425 (NH), 1658 (C=O) cm$^{-1}$.

[Compound 6]
2-(3-trifluoromethylphenylimino)-3-methyl-4-[N-(4-methylphenyl)carbamoylmethyl]-1,3-thiazol-4-ine hydrobromide (R1=4-CH$_3$, R$_2$=3-CF$_3$, R$_3$=CH$_3$, HX=HBr).

Starting materials: methylisothiocyanate, 3-trifluoromethylaniline, 4-bromo-3-oxo-N-(4-methylphenyl)butane amide Yield: 71% Melting point: 199–200° C. $^1$H NMR (DMSO-d$_6$) δ 2.25 (s, 3H, ArCH$_3$), 3.67 (s, 3H, 3-CH$_3$), 3.98 (s, 2H, 4-CH$_2$), 6.93 (s, 1H, 5-vinyl H), 7.12~7.80 (m, 8H, ArH), 10.31 (s, 1H, NH); IR(KBr) 3435 (NH), 1660 (C=O) cm$^{-1}$.

[Compound 7]
2-(3-trifluoromethylphenylimino)-3-methyl-4-[N-(3-trifluoromethylphenyl)carbamoylmethyl]-1,3-thiazol-4-ine hydrobromide (R1=3-CF$_3$, R$_2$=3-CF$_3$, R$_3$=CH$_3$, HX=HBr).

Starting materials: methylisothiocyanate, 3-trifluoromethylaniline, 4-bromo-3-oxo-N-(3-trifluoromethylphenyl)butane amide Yield: 84% Melting point: 223–224° C. $^1$H NMR (DMSO-d$_6$) δ 3.66 (s, 3H, 3-CH$_3$), 4.05 (s, 2H, 4-CH$_2$), 6.95 (s, 1H, 5-vinyl H), 7.43~8.14 (m, 8H, ArH), 10.78 (s, 1H, NH); IR(KBr) 3435 (NH), 1688 (C=O) cm$^{-1}$.

[Compound 8]
2(4-trifluoromethylphenylimino)-3-methyl-4-[N-(3-trifluoromethylphenyl)carbamoylmethyl]-1,3-thiazol-4-ine hydrobromide (R1=3-CF$_3$, R$_2$=4-CF$_3$, R$_3$=CH$_3$, HX=HBr).

Starting materials: methylisothiocyanate, 4-trifluoromethylaniline, 4-bromo-3-oxo-N-(3-trifluoromethylphenyl)butane amide Yield: 76% Melting point: 218–219° C. $^1$H NMR (DMSO-d$_6$) δ 3.52 (s, 3H, 3-CH$_3$), 3.91 (s, 2H, 4-CH$_2$), 6.66 (s, 1H, 5-vinyl H), 7.15~8.23 (m, 8H, ArH), 10.53 (s, 1H, NH); IR(KBr) 3435 (NH), 1664 (C=O) cm$^{-1}$.

[Compound 9]
2-(2-trifluoromethylphenylimino)-3-methyl-4-[N-(3-trifluoromethylphenyl)carbamoylmethyl]-1,3-thiazol-4-ine hydrobromide (R1=3-CF$_3$, R$_2$=2-CF$_3$, R$_3$=CH$_3$, HX=HBr).

Starting materials: methylisothiocyanate, 2-trifluoromethylaniline, 4-bromo-3-oxo-N-(3-trifluoromethylphenyl)butane amide Yield: 96% Melting point: 197–198° C. $^1$H NMR (DMSO-d$_6$) δ 3.48 (s, 3H, 3-CH$_3$), 3.90 (s, 2H, 4-CH$_2$), 6.50 (s, 1H, 5-vinyl H), 7.31~8.12 (m, 8H, ArH), 10.71 (s, 1H, NH); IR(KBr) 3435 (NH), 1688 (C=O) cm$^{-1}$.

[Compound 10]
2-(3,5-dichlorophenylimino)-3-methyl-4-[N-(3-trifluoromethylphenyl)carbamoylmethyl]-1,3-thiazol-4-ine hydrobromide (R1=3-CF$_3$, R$_2$=3-Cl, 5-Cl, R$_3$=CH$_3$, HX=HBr).

Starting materials: methylisothiocyanate, 3,5-dichloroaniline, 4-bromo-3oxo-N-(3-trifluoromethylphenyl)butane amide Yield: 81% Melting point: 198–199° C. $^1$H NMR (DMSO-d$_6$) δ 3.52 (s, 3H, 3-CH$_3$), 3.95 (s, 2H, 4-CH$_2$), 6.70 (s, 1H, 5-vinyl H), 7.30~8.11 (m, 7H, ArH), 10.70 (s, 1H, NH); IR(KBr) 3396 (NH), 1672 (C=O) cm$^{-1}$.

[Compound 11]
2-(4-phenoxyphenylimino)-3-methyl-4-[N-(3-trifluoromethylphenyl)carbamoylmethyl]-1,3-thiazol-4-ine hydrobromide (R1=3-CF$_3$, R$_2$=4-OC$_6$H$_5$, R$_3$=CH$_3$, HX=HBr).

Starting materials: methylisothiocyanate, 4-phenoxyaniline, 4-bromo-3-oxo-N-(3-trifluoromethylphenyl)butane amide Yield: 86% Melting point: 229–230° C. $^1$H NMR (DMSO-d$_6$) δ 3.68 (s, 3H, 3-CH$_3$), 4.05 (s, 2H, 4-CH$_2$), 7.01 (s, 1H, 5-vinyl H), 7.08~7.79 (m, 13H, ArH), 10.77 (s, 1H, NH); IR(KBr) 3435 (NH), 1670 (C=O) cm$^{-1}$.

[Compound 12]
2-(3-nitrophenylimino)-3-methyl-4-[N-(3-trifluoromethylphenyl)carbamoylmethyl]-1,3-thiazol-4-ine hydrobromide (R1=3-CF$_3$, R$_2$=3-NO$_2$, R$_3$=CH$_3$, HX=HBr).

Starting materials: methylisothiocyanate, 3-nitroaniline, 4-bromo-3-oxo-N-(3-trifluoromethylphenyl)butane amide Yield: 76% Melting point: 241–242° C. $^1$H NMR (DMSO-d$_6$) δ 3.68 (s, 3H, 3-CH$_3$), 4.07 (s, 2H, 4-CH$_2$), 7.00 (s, 1H, 5-vinyl H), 7.41~8.27 (m, 8H, ArH), 10.82 (s, 1H, NH); IR(KBr) 3425 (NH), 1698 (C=O) cm$^{-1}$.

[Compound 13]
2-(4-phenoxyphenylimino)-3-methyl-4-[N-(4-methylphenyl)carbamoylmethyl]-1,3-thiazol-4-ine hydrobromide (R1=4-CH$_3$, R$_2$=4-OC$_6$H$_5$, R$_3$=CH$_3$, HX=HBr).

Starting materials: methylisothiocyanate, 4-phenoxyaniline, 4-bromo-3-oxo-N-(4-methylphenyl)butane amide Yield: 87% Melting point: 255–256° C. $^1$H NMR (DMSO-d$_6$) δ 2.25 (s, 3H, ArCH$_3$), 3.67 (s, 3H, 3-CH$_3$), 3.97 (s, 2H, 4-CH$_2$), 6.96 (s, 1H, 5-vinyl H), 7.07~7.49 (m, 13H, ArH), 10.28 (s, 1H, NH); IR(KBr) 3425 (NH), 1658 (C=O) cm$^{-1}$.

[Compound 14]
2-(4-trifluoromethylphenylimino)-3-methyl-4-[N-(4-methylphenyl)carbamoylmethyl]-1,3-thiazol-4-ine hydrobromide (R1=4-CH$_3$, R$_2$=4-CF$_3$, R$_3$=CH$_3$, HX=HBr).

Starting materials: methylisothiocyanate, 4-trifluoromethylaniline, 4-bromo-3-oxo-N-(4-methylphenyl)butane amide Yield: 94% Melting point: 263–264° C. $^1$H NMR (DMSO-d$_6$) δ 2.25 (s, 3H, ArCH$_3$), 3.62 (s, 3H, 3-CH$_3$), 3.93 (s, 2H, 4-CH$_2$), 6.83 (s, 1H, 5-vinyl H), 7.11~7.84 (m, 8H, ArH), 10.25 (s, 1H, NH); IR(KBr) 3435 (NH), 1656 (C=O) cm$^{-1}$.

[Compound 15]
2-(3-nitrophenylimino)-3-methyl-4-[N-(4-methylphenyl)carbamoylmethyl]-1,3-thiazol-4-ine hydrobromide (R1=4-CH$_3$, R$_2$=3-NO$_2$, R$_3$=CH$_3$, HX=HBr).

Starting materials: methylisothiocyanate, 3-nitroaniline, 4-bromo-3-oxo-N-(4-methylphenyl)butane amide Yield: 92% Melting point: 217° C. $^1$H NMR (DMSO-6) δ 2.25 (s, 3H, ArCH$_3$), 3.61 (s, 3H, 3-CH$_3$), 4.00 (s, 2H, 4-CH$_2$), 6.85 (s, 1H, 5-vinyl H), 7.42–8.12 (m, 8H, ArH), 10.72 (s, 1H, NH); IR(KBr) 3236 (NH), 1654 (C=O) cm$^{-1}$.

[Compound 16]
2-(4-nitrophenylimino)-3-methyl-4-[N-(4-methylphenyl)carbamoylmethyl]-1,3-thiazol-4-ine hydrobromide (R1=4-CH$_3$, R$_2$=4-NO$_2$, R$_3$=CH$_3$, HX=HBr).

Starting materials: methylisothiocyanate, 4-nitroaniline, 4-bromo-3-oxo-N-(4-methylphenyl)butane amide Yield: 92% Melting point: 239° C. $^1$H NMR (DMSO-$d_6$) δ 2.25 (s, 3H, $CH_3$), 3.66 (s, 3H, 3-$CH_3$), 3.98 (s, 2H, 4-$CH_2$), 6.96 (s, 1H, 5-vinyl H), 7.48~8.32 (m, 8H, ArH), 10.33 (s, 1H, NH); IR(KBr) 3445 (NH), 1654 (C=O) $cm^{-1}$.

[Compound 17]

2-(4-phenoxyphenylimino)-3-methyl-4-[N-(3-chlorophenyl)carbamoylmethyl]-1,3-thiazol-4-ine hydrobromide (R1=3-Cl, $R_2$=4-$OC_6H_5$, $R_3$=$CH_3$, HX=HBr).

Starting materials: methylisothiocyanate, 4-phenoxyaniline, 4-bromo-3-oxo-N-(3-chlorophenyl)butane amide Yield: 82% Melting point: 240–241° C. $^1$H NMR (DMSO-$d_6$) δ 3.67 (s, 3H, 3-$CH_3$), 4.02 (s, 2H, 4-$CH_2$), 7.00 (s, 1H, 5-vinyl H), 7.07~7.83 (m, 13H, ArH), 10.61 (s, 1H, NH); IR(KBr) 3445 (NH), 1668 (C=O) $cm^{-1}$.

[Compound 18]

2-(3-nitrophenylimino)-3-methyl-4-[N-(3-chlorophenyl)carbamoylmethyl]-1,3-thiazol-4-ine hydrobromide (R1=3-Cl, $R_2$=3-$NO_2$, $R_3$=$CH_3$, HX=HBr).

Starting materials: methylisothiocyanate, 3-nitroaniline, 4-bromo-3-oxo-N-(3-chlorophenyl)butane amide Yield: 92% Melting point: 238–240° C. $^1$H NMR (DMSO-$d_6$) δ 3.64 (s, 3H, 3-$CH_3$), 4.00 (s, 2H, 4-$CH_2$), 6.89 (s, 1H, 5-vinyl H), 7.14~7.83 (m, 8H, ArH), 10.59 (s, 1H, NH); IR(KBr) 3435 (NH), 1686 (C=O) $cm^{-1}$.

[Compound 19]

2-(3-trifluoromethylphenylimino)-3-methyl-4-[N-(3-chlorophenyl)carbamoylmethyl]-1,3-thiazol-4-ine hydrobromide (R1=3-Cl, $R_2$=3-$CF_3$, $R_3$=$CH_3$, HX=HBr).

Starting materials: methylisothiocyanate, 3-trifluoromethylaniline, 4-bromo-3-oxo-N-(3-chlorophenyl)butane amide Yield: 89% Melting point: 253° C. $^1$H NMR (DMSO-$d_6$) δ 3.64 (s, 3H, 3-$CH_3$), 4.00 (s, 2H, 4-$CH_2$), 6.89 (s, 1H, 5-vinyl H), 7.16~7.83 (m, 8H, ArH), 10.59 (s, 1H, NH); IR(KBr) 3445 (NH), 1686 (C=O) $cm^{-1}$.

[Compound 20]

2-(4-trifluoromethylphenylimino)-3-methyl-4-[N-(3-chlorophenyl)carbamoylmethyl]-1,3-thiazol-4-ine hydrobromide (R1=3-Cl, $R_2$=4-$CF_3$, $R_3$=$CH_3$, HX=HBr).

Starting materials: methylisothiocyanate, 4-trifluoromethylaniline, 4-bromo-3-oxo-N-(3-chlorophenyl)butane amide Yield: 93% Melting point: 231–232° C. $^1$H NMR (DMSO-$d_6$) δ 3.64 (s, 3H, 3-$CH_3$), 4.00 (s, 2H, 4-$CH_2$), 6.91 (s, 1H, 5-vinyl H), 7.13~7.87 (m, 8H, ArH), 10.60 (s, 1H, NH); IR(KBr) 3424 (NH), 1662 (C=O) $cm^{-1}$.

[Compound 21]

2-(3,5-dichlorophenylimino)-3-methyl-4-[N-(3-chlorophenyl)carbamoylmethyl]-1,3-thiazol-4-ine hydrobromide (R1=3-Cl, $R_2$=3-Cl, 5-Cl $R_3$=$CH_3$, HX=HBr).

Starting materials: methylisothiocyanate, 3,5-dichloroaniline, 4-bromo-3-oxo-N-(3-chlorophenyl)butane amide Yield: 91% Melting point: 291–220° C. $^1$H NMR (DMSO-$d_6$) δ 3.57 (s, 3H, 3-CH3), 3.97 (s, 2H, 4-$CH_2$), 6.82 (s, 1H, 5-vinyl H), 6.95~7.82 (m, 7H, ArH), 10.59 (s, 1H, NH); IR(KBr) 3445 (NH), 1668 (C=O) $cm^{-1}$.

[Compound 22]

2-(4-chloro-3-(3,3-dimethylallyloxy)phenylimino)-3-methyl-4-(N-phenylcarbamoylmethyl)-1,3-thiazol-4-ine hydrobromide (R1=H, $R_2$=4-Cl, 3-$OCH_2CH$=$C(CH_3)_2$, $R_3$=$CH_3$, HX=HBr).

Starting materials: methylisothiocyanate, 4-chloro-3-(3,3-dimethylallyloxy)aniline, 4-bromo-3-oxo-N-phenylbutane amide Yield: 75% Melting point: 196–197° C. $^1$H NMR (DMSO-$d_6$) δ 1.70 (s, 3H, $CH_3$), 1.76 (s, 3H, $CH_3$), 3.67 (s, 3H, 3-$CH_3$), 4.01 (s, 2H, 4-$CH_2$), 4.62 (d, 2H, $OCH_2$), 5.46 (t, 1H, CH), 7.00 (s, 1H, 5-vinyl H), 7.05~7.60 (m, 8H, ArH), 10.39 (s, 1H, NH); IR(KBr) 3435 (NH), 1676 (C=O) $cm^{-1}$.

[Compound 23]

2-(4-chloro-3-isopropyloxycarbonylphenylimino)-3-methyl-4-(N-phenylcarbamoylmethyl)-1,3-thiazol-4-ine hydrobromide (R1=H, $R_2$=4-Cl, 3-$CO_2CH(CH_3)_2$, $R_3$=$CH_3$, HX=HBr).

Starting materials: methylisothiocyanate, 4-chloro-3-isopropyloxycarbonylaniline, 4-bromo-3-oxo-N-phenylbutane amide Yield: 89% Melting point: 196° C. $^1$H NMR (DMSO-$d_6$) δ 1.32 (d, 6H, $(CH_3)_2$), 3.61 (s, 3H, $CH_3$), 3.96 (s, 2H, 4-$CH_2$), 5.16 (m, 1H, OCH), 6.85 (s, 1H, 5-vinyl H), 7.05~7.74 (m, 8H, ArH), 10.36 (s, 1H, NH); IR(KBr) 3424 (NH), 1658 (C=O) $cm^{-1}$.

[Compound 24]

2-(5-chloro-2-methylphenylimino)-3-methyl-4-(N-phenylcarbamoymethyl)-1,3-thiazol-4-ine hydrobromide (R1=H, $R_2$=5-Cl, 2-$CH_3$, $R_3$=$CH_3$, HX=HBr).

Starting materials: methylisothiocyanate, 5-chloro-2-methylaniline, 4-bromo-3-oxo-N-phenylbutane amide Yield: 83% Melting point: 202–204° C. $^1$H NMR (DMSO-$d_6$) δ 2.23 (s, 3H, $ArCH_3$), 3.67 (s, 3H, 3-$CH_3$), 3.98 (s, 2H, 4-$CH_2$), 6.90 (s, 1H, 5-vinyl H), 7.05~7.62 (m, 8H, ArH), 10.39 (s, 1H, NH); IR(KBr) 3445 (NH), 1680 (C=O) $cm^{-1}$.

[Compound 25]

2-(4-chloro-2-methylphenylimino)-3-methyl-4-(N-phenylcarbamoylmethyl)-1,3-thiazol-4-ine hydrobromide (R1=H, $R_2$=4-Cl, 2-$CH_3$, $R_3$=$CH_3$, HX=HBr).

Starting materials: methylisothiocyanate, 4-chloro-2-methylaniline, 4-bromo-3-oxo-N-phenylbutane amide Yield: 84% Melting point: 225–226° C. $^1$H NMR (DMSO-$d_6$) δ 2.25 (s, 3H, $ArCH_3$), 3.68 (s, 3H, 3-$CH_3$), 3.98 (s, 2H, 4-$CH_2$), 6.92 (s, 1H, 5-vinyl H), 7.05~7.61 (m, 8H, ArH), 10.38 (s, 1H, NH); IR(KBr) 3425 (NH), 1668 (C=O) $cm^{-1}$.

[Compound 26]

2-(4-bromo-2-methylphenylimino)-3-methyl-4-(N-phenylcarbamoylmethyl)-1,3-thiazol-4-ine hydrobromide (R1=H, $R_2$=4-Br, 2-$CH_3$, $R_3$=$CH_3$, HX=HBr).

Starting materials: methylisothiocyanate, 4-bromo-2-methylaniline, 4-bromo-3-oxo-N-phenylbutane amide Yield: 86% Melting point: 227–229° C. $^1$H NMR (DMSO-$d_6$) δ 2.25 (s, 3H, $ArCH_3$), 3.67 (s, 3H, 3-$CH_3$), 3.97 (s, 2H, 4-$CH_2$), 6.91 (s, 1H, 5-vinyl H), 7.05~7.69 (m, 8H, ArH), 10.38 (s, 1H, NH); IR(KBr) 3415 (NH), 1668 (C=O) $cm^{-1}$.

[Compound 27]

2-(2,4-difluorophenylimino)-3-methyl-4-(N-phenylcarbamoylmethyl)-1,3-thiazol-4-ine hydrobromide (R1=H, $R_2$=2-F, 4-F, $R_3$=$CH_3$, HX=HBr).

Starting materials: methylisothiocyanate, 2,4-difluoroaniline, 4-bromo-3-oxo-N-phenylbutane amide Yield: 98% Melting point: 240° C. $^1$H NMR (DMSO-$d_6$) δ 3.63 (s, 3H, 3-$CH_3$), 3.95 (s, 2H, 4-$CH_2$), 6.86 (s, 1H, 5-vinyl H), 7.05~7.61 (m, 8H, ArH), 10.37 (s, 1H, NH); IR(KBr) 3435 (NH), 1676 (C=O) $cm^{-1}$.

[Compound 28]

2-(2-methoxyphenylimino)-3-methyl-4-[N-(4-methylphenyl)carbamoylmethyl]-1,3-thiazol-4-ine hydrobromide (R1=$CH_3$, $R_2$=2-$OCH_3$, $R_3$=$CH_3$, HX=HBr).

Starting materials: methylisothiocyanate, 2-methoxyaniline, 4-bromo-3-oxo-N-(4-methylphenyl)butane amide Yield: 99% Melting point: 217–218° C. $^1$H NMR (DMSO-$d_6$) δ 2.26 (s, 3H, ArCH$_3$), 3.70 (s, 3H, 3-CH$_3$), 3.85 (s, 3H, OCH$_3$), 3.99 (s, 2H, 4-CH$_2$), 6.98 (s, 1H, 5-vinyl H), 7.09~7.52 (m, 8H, ArH), 10.31 (s, 1H, NH); IR(KBr) 3435 (NH), 1682 (C=O) cm$^{-1}$.

[Compound 29]
2-(4-methoxyphenylimino)-3-methyl-4-[N-(4-methylphenyl)carbamoylmethyl]-1,3-thiazol-4-ine hydrobromide (R1=CH$_3$, R$_2$=4-OCH$_3$, R$_3$=CH$_3$, HX=HBr).

Starting materials: methylisothiocyanate, 4-methoxyaniline, 4-bromo-3-oxo-N-(4-methylphenyl)butane amide Yield: 90% Melting point; 261–262° C. $^1$H NMR (DMSO-$d_6$) δ 2.25 (s, 3H, CH$_3$), 3.68 (s, 3H, 3-CH$_3$), 3.80 (s, 3H, OCH$_3$), 3.99 (s, 2H, 4-CH$_2$), 6.99 (s, 1H, 5-vinyl H), 7.09~7.50 (m, 8H, ArH), 10.33 (s, 1H, NH); IR(KBr) 3425 (NH), 1664 (C=O) cm$^{-1}$.

[Compound 30]
2-[4-(n-butyl)phenylimino]-3-methyl-4-[N-(4-methylphenyl)carbamoylmethyl]-1,3-thiazol-4-ine hydrobromide (R1=CH$_3$, R$_2$=(CH$_2$)$_3$CH$_3$, R$_3$=CH$_3$, HX=HBr).

Starting materials: methylisothiocyanate, 4-(n-butyl)aniline, 4-bromo-3-oxo-N-(4-methylphenyl)butane amide Yield: 87% Melting point: 228–229° C. $^1$H NMR (DMSO-$d_6$) δ 0.91 (t, 3H, J=7.3 Hz, CH$_3$), 1.32 (m, 2H, CH$_2$), 1.58 (m, 2H, CH$_2$), 2.25 (s, 3H, CH$_3$), 2.63 (t, 2H, CH$_2$), 3.69 (s, 3H, 3-CH$_3$), 3.99 (s, 2H, 4-CH$_2$), 7.00 (s, 1H, 5-vinyl H), 7.12~7.52 (m, 8H, ArH), 10.31 (s, 1H, NH); IR(KBr) 3435 (NH), 1666 (C=O) cm$^{-1}$.

[Compound 31]
2-(2,4-difluorophenylimino)-3-methyl-4-[N-(4-methylphenyl)carbamoylmethyl]-1,3-thiazol-4-ine hydrobromide (R1=CH$_3$, R$_2$=2-F, 4-F, R$_3$=CH$_3$, HX=HBr).

Starting materials: methyl isothiocyanate, 2,4-difluoroaniline, 4-bromo-3-oxo-N-(4-methylphenyl)butane amide Yield: 88% Melting point: 206–207° C. $^1$H NMR (DMSO-$d_6$) δ 2.25 (s, 3H, ArCH$_3$), 3.62 (s, 3H, 3-CH$_3$), 3.93 (s, 2H, 4-CH$_2$), 6.84 (s, 1H, 5-vinyl H), 7.11~7.58 (m, 7H, ArH), 10.27 (s, 1H, NH); IR(KBr) 3435 (NH), 1670 (C=O) cm$^{-1}$.

[Compound 32]
2-(4-chloro-2-methylphenylimino)-3-methyl-4-[N-(4-methylphenyl)carbamoylmethyl]-1,3-thiazol-4-ine hydrobromide (R1=CH$_3$, R$_2$=4-Cl, 2-CH$_3$, R$_3$=CH$_3$, HX=HBr).

Starting materials: methylisothiocyanate, 4-chloro-2-methylaniline, 4-bromo-3-oxo-N-(4-methylphenyl)butane amide Yield: 89% Melting point: 228–230° C. $^1$H NMR (DMSO-$d_6$) δ 2.26 (s, 3H, ArCH$_3$), 3.69 (s, 3H, 3-CH$_3$), 3.96 (s, 2H, 4-CH$_2$), 6.98 (s, 1H, 5-vinyl H), 7.12~7.57 (m, 7H, ArH), 10.31 (s, 1H, NH); IR(KBr) 3435 (NH), 1662 (C=O) cm$^{-1}$.

[Compound 33]
2-(4-bromo-2-methylphenylimino)-3-methyl-4-[N-(4-methylphenyl)carbamoylmethyl]-1,3-thiazol-4-ine hydrobromide (R1=CH$_3$, R$_2$=4-Br, 2-CH$_3$, R$_3$=CH$_3$, HX=HBr).

Starting materials: methylisothiocyanate, 4-bromo-2-methylaniline, 4-bromo-3-oxo-N-(4-methylphenyl)butane amide Yield: 91% Melting point: 230–231° C. $^1$H NMR (DMSO-$d_6$) δ 2.25 (s, 3H, ArCH$_3$), 3.66 (s, 3H, 3-CH$_3$), 3.94 (s, 2H, 4-CH$_2$), 6.88 (s, 1H, 5-vinyl H), 7.11~7.69 (m, 7H, ArH), 10.28 (s, 1H, NH); IR(KBr) 3425 (NH), 1662 (C=O) cm$^{-1}$.

[Compound 34]
2-(5-chloro-2-methylphenylimino)-3-methyl-4-[N-(4-methylphenyl)carbamoylmethyl]-1,3-thiazol-4-ine hydrobromide (R1=CH$_3$, R$_2$=5-Cl, 2-CH$_3$, R$_3$=CH$_3$, HX=HBr).

Starting materials: methylisothiocyanate, 5-chloro-2-methylaniline, 4-bromo-3-oxo-N-(4-methylphenyl)butane amide Yield: 99% Melting point: 195–196° C. $^1$H NMR (DMSO-$d_6$) δ 2.25 (s, 3H, ArCH$_3$), 3.69 (s, 3H, 3-CH$_3$), 3.97 (s, 2H, 4-CH$_2$), 6.92 (s, 1H, 5-vinyl H), 7.12~7.59 (m, 7H, ArH), 10.32 (s, 1H, NH); IR(KBr) 3445 (NH), 1656 (C=O) cm$^{-1}$.

[Compound 35]
2-(3-chloro-4-methylphenylimino)-3-methyl-4[N-(4-methylphenyl)carbamoylmethyl]-1,3-thiazol-4-ine hydrobromide (R1=CH$_3$, R$_2$=3-Cl, 4-CH$_3$, R$_3$=CH$_3$, HX=HBr).

Starting materials: methylisothiocyanate, 3-chloro-2-methylaniline, 4-bromo-3-oxo-N-(4-methylphenyl)butane amide Yield: 91% Melting point: 242–244° C. $^1$H NMR (DMSO-$d_6$) δ 2.25 (s, 3H, ArCH$_3$), 2.37 (s, 3H, CH$_3$), 3.69 (s, 3H 3-CH$_3$), 4.00 (s, 2H, 4-CH$_2$), 7.01 (s, 1H, 5-vinyl H), 7.12~7.59 (m, 8H, ArH), 10.32 (s, 1H, NH); IR(KBr) 3445 (NH), 1668 (C=O) cm$^{-1}$.

[Compound 36]
2-(4-methoxyphenylimino)-3-methyl-4-[N-(3-trifluoromethylphenyl)carbamoylmethyl]-1,3-thiazol-4-ine hydrobromide (R1=CF$_3$, R$_2$=4-OCH$_3$, R$_3$=CH$_3$, HX=HBr).

Starting materials: methylisothiocyanate, 4-methoxyaniline, 4-bromo-3-oxo-N-(3-trifluoromethylphenyl)butane amide Yield: 71% Melting point: 222–224° C. $^1$H NMR (DMSO-$d_6$) δ 3.67 (s, 3H, 3-CH$_3$), 3.81 (s, 3H, OCH$_3$), 4.04 (s, 2H, 4-CH$_2$), 6.99 (s, 1H, 5-vinyl H), 7.10~8.13 (m, 8H, ArH), 10.75 (s, 1H, NH); IR(KBr) 3445 (NH), 1676 (C=O) cm$^{-1}$.

[Compound 37]
2-(4-chloro-3-trifluoromethylphenylimino)-3-methyl-4-(N-phenylcarbamoylmethyl)-1,3-thiazol-4-ine hydrobromide (R1=H, R$_2$=4-Cl, 3-CF$_3$, R$_3$=CH$_3$, HX=HBr).

Starting materials: methylisothiocyanate, 4-chloro-3-trifluoromethylaniline, 4-bromo-3-oxo-N-phenylbutane amide Yield: 83% Melting point: 214–215° C. $^1$H NMR (DMSO-$d_6$) δ 3.56 (s, 3H, 3-CH$_3$), 3.92 (s, 2H, 4-CH$_2$), 6.73 (s, 1H, 5-vinyl H), 7.05~7.80 (m, 8H, ArH), 10.33 (s, 1H, NH); IR(KBr) 3435 (NH), 1658 (C=O) cm$^{-1}$.

[Compound 38]
2-(2-fluoro-4-nitrophenylimino)-3-methyl-4-(N-phenylcarbamoylmethyl)-1,3-thiazol-4-ine hydrobromide (R1=H, R$_2$=2-F, 4-NO$_2$, R$_3$=CH$_3$, HX=HBr).

Starting materials: methylisothiocyanate, 2-fluoro-4-nitroaniline, 4-bromo-3-oxo-N-phenylbutane amide Yield: 59% Melting point: 240–245° C. $^1$H NMR (DMSO-$d_6$) δ 3.50 (s, 3H, 3-CH$_3$), 4.07 (s, 2H, 4-CH$_2$), 7.03 (s, 1H, 5-vinyl H), 7.30~7.99 (m, 8H, ArH), 9.71 (s, 1H, NH); IR(KBr) 3432 (NH), 1659 (C=O) cm$^{-1}$.

[Compound 39]
2-(4-trifluoromethoxyphenylimino)-3-methyl-4-(N-phenylcarbamoylmethyl)-1,3-thiazol-4-ine hydrobromide (R1=H, R$_2$=4-OCF$_3$, R$_3$=CH$_3$, HX=HBr).

Starting materials: methylisothiocyanate, 4-trifluoromethoxyaniline, 4-bromo-3-oxo-N-phenylbutane amide Yield: 99% Melting point: 242–243° C. $^1$H NMR (DMSO-$d_6$) δ 3.68 (s, 3H, 3-CH$_3$), 4.01 (s, 2H, 4-CH$_2$), 6.99 (s, 1H, 5-vinyl H), 7.05~7.61 (m, 9H, ArH), 10.39 (s, 1H, NH); IR(KBr) 3445 (NH), 1656 (C=O) cm$^{-1}$.

[Compound 40]
2-(2,4-dichlorophenylimino)-3-methyl-4-(N-phenylcarbamoylmethyl)-1,3-thiazol-4-ine hydrobromide (R1=H, R$_2$=2-Cl, 4-Cl, R$_3$=CH$_3$, HX=HBr).

Starting materials: methylisothiocyanate, 2,4-dichloroaniline, 4-bromo-3oxo-N-phenylbutane amide Yield: 99% Melting point: 149–151° C. $^1$H NMR (DMSO-d$_6$) δ 3.57 (s, 3H, 3-CH$_3$), 3.91 (s, 2H, 4-CH$_2$), 6.67 (s, 1H, 5-vinyl H), 7.02~7.79 (m, 8H, ArH), 10.37 (s, 1H, NH); IR(KBr) 3405 (NH), 1668 (C=O) cm$^{-1}$.

[Compound 41]

2-(3-chloro-4-methylphenylimino)-3-methyl-4-(N-phenylcarbamoylmethyl)-1,3-thiazol-4-ine hydrobromide (R1=H, R$_2$=3-Cl, 4-CH$_3$, R$_3$=CH$_3$, HX=HBr).

Starting materials: methylisothiocyanate, 3-chloro-4-methylaniline, 4-bromo-3-oxo-N-phenylbutane amide Yield: 85% Melting point: 219–221° C. $^1$H NMR (DMSO-d$_6$) δ 2.36 (s, 3H, ArCH$_3$), 3.68 (s, 3H, 3-CH$_3$), 4.01 (s, 2H, 4-CH$_2$), 7.01 (s, 1H, 5-vinyl H), 7.05~7.62 (m, 8H, ArH), 10.41 (s, 1H, NH); IR(KBr) 3415 (NH), 1656 (C=O) cm$^{-1}$.

[Compound 42)]

2-(4-chloro-2-fluorophenylimino)-3-methyl-4-(N-phenylcarbamoylmethyl)-1,3-thiazol-4-ine hydrobromide (R1=H, R$_2$=4-Cl, 2-F, R$_3$=CH$_3$, HX=HBr).

Starting materials: methylisothiocyanate, 4-chloro-2-fluoroaniline, 4-bromo-3-oxo-N-phenylbutane amide Yield: 72% Melting point: 227–229° C. $^1$H NMR (DMSO-d$_6$) δ 3.61 (s, 3H, 3-CH$_3$), 3.94 (s, 2H, 4-CH$_2$), 6.81 (s, 1H, 5-vinyl H), 7.05~7.81 (m, 8H, ArH), 10.36 (s, 1H, NH); IR(KBr) 3415 (NH), 1684 (C=O) cm$^{-1}$.

[Compound 43]

2-(3-chloro-4-fluorophenylimino)-3-methyl-4-(N-phenylcarbamoylmethyl)-1,3-thiazol-4-ine hydrobromide (R1=H, R$_2$=3-Cl, 4-F, R$_3$=CH$_3$, HX=HBr).

Starting materials: methylisothiocyanate, 3-chloro-4-fluoroaniline, 4-bromo-3-oxo-N-phenylbutane amide Yield: 87% Melting point: 217–218° C. $^1$H NMR (DMSO-d$_6$) δ 3.62 (s, 3H, 3-CH$_3$), 3.98 (s, 2H, 4-CH$_2$), 6.90 (s, 1H, 5-vinyl H), 7.06~7.70 (m, 8H, ArH), 10.37 (s, 1H, NH); IR(KBr) 3435 (NH), 1656 (C=O) cm$^{-1}$.

[Compound 44]

2-(2-fluoro-5-methylphenylimino)-3-methyl-4-(N-phenylcarbamoylmethyl)-1,3-thiazol-4-ine hydrobromide (R1=H, R$_2$=2-F, 5-CH$_3$, R$_3$=CH$_3$, HX=HBr).

Starting materials: methylisothiocyanate, 2-fluoro-5-methylaniline, 4-bromo-3-oxo-N-phenylbutane amide Yield: 91% Melting point: 214–216° C. $^1$H NMR (DMSO-d$_6$) δ 2.33 (s, 3H, ArCH$_3$), 3.69 (s, 3H, 3-CH$_3$), 4.01 (s, 2H, 4-CH$_2$), 6.98 (s, 1H, 5-vinyl H), 7.05~7.63 (m, 8H, ArH), 10.43 (s, 1H, NH); IR(KBr) 3445 (NH), 1684 (C=O) cm$^{-1}$.

[Compound 45]

2-(3,5-ditrifluoromethylphenylimino)-3-methyl-4-(N-phenylcarbamoylmethyl)-1,3-thiazol-4-ine hydrobromide (R1=H, R$_2$=3-CF$_3$, 5-CF$_3$, R$_3$=CH$_3$, HX=HBr).

Starting materials: methylisothiocyanate, 3,5-ditrifluoromethylaniline, 4-bromo-3-oxo-N-phenylbutane amide Yield: 74% Melting point: 209–211° C. $^1$H NMR (DMSO-d$_6$) δ 3.54 (s, 3H, 3-CH$_3$), 3.91 (s, 2H, 4-CH$_2$), 6.64 (s, 1H, 5-vinyl H), 7.04~7.85 (m, 8H, ArH), 10.34 (s, 1H, NH); IR(KBr) 3395 (NH), 1688 (C=O) cm$^{-1}$.

[Compound 46]

2-(4-cyanophenylimino)-3-methyl-4-[N-(4-methylphenyl)carbamoylmethyl-1,3-thiazol-4-ine hydrobromide (R1=4-CH$_3$, R$_2$=4-CN, R$_3$=CH$_3$, HX=HBr).

Starting materials: methylisothiocyanate, 4-cyanoaniline, 4-bromo-3-oxo-N-(4-methylphenyl)butane amide Yield: 99% Melting point: 238–239° C. $^1$H NMR (DMSO-d$_6$) δ 2.25 (s, 3H, ArCH$_3$), 3.67 (s, 3H, 3-CH$_3$), 3.99 (s, 2H, 4-CH$_2$), 6.98 (s, 1H, 5-vinyl H), 7.11~7.95 (m, 8H, ArH), 10.33 (s, 1H, NH), IR(KBr) 3425 (NH), 1654 (C=O) cm$^{-1}$.

[Compound 47]

2-(4-trifluoromethoxyphenylimino)-3-methyl-4-[N-(4-methylphenyl)carbamoylmethyl]-1,3-thiazol-4-ine hydrobromide (R1=4-CH$_3$, R$_2$=4-OCF$_3$, R$_3$=CH$_3$, HX=HBr).

Starting materials: methylisothiocyanate, 4-trifluoromethoxyaniline, 4-bromo-3-oxo-N-(4-methylphenyl)butane amide Yield: 99% Melting point: 254–255° C. $^1$H NMR (DMSO-d$_6$) δ 2.25 (s, 3H, ArCH$_3$), 3.71 (s, 3H, 3-CH$_3$), 4.02 (s, 2H, 4-CH$_2$), 7.04 (s, 1H, 5-vinyl H), 7.11~7.65 (m, 8H, ArH), 10.36 (s, 1H, NH); IR(KBr) 3445 (NH), 1656 (C=O) cm$^{-1}$.

[Compound 48]

2-(3-fluorophenylimino)-3-methyl-4-[N-(4-methylphenyl)carbamoylmethyl]-1,3-thiazol-4-ine hydrobromide (R1=4-CH$_3$, R$_2$=3-F, R$_3$=CH$_3$, HX=HBr).

Starting materials: methylisothiocyanate, 3-fluoroaniline, 4-bromo-3-oxo-N-(4-methylphenyl)butane amide Yield: 94% Melting point: 240–242° C. $^1$H NMR (DMSO-d$_6$) δ 2.25 (s, 3H, ArCH$_3$), 3.73 (s, 3H, 3-CH$_3$), 4.03 (s, 2H, 4-CH$_2$), 7.07 (s, 1H, 5-vinyl H), 7.11~7.63 (m, 8H, ArH), 10.38 (s, 1H, NH); IR(KBr) 3445 (NH), 1668 (C=O) cm$^{-1}$.

[Compound 49]

2-(2,4-dichlorophenylimino)-3-methyl-4-[N-(4-methylphenyl)carbamoylmethyl]-1,3-thiazol-4-ine hydrobromide (R1=4-CH$_3$, R$_2$=2-Cl, 4-Cl, R$_3$=CH$_3$, HX=HBr).

Starting materials: methylisothiocyanate, 2,4-dichloroaniline, 4-bromo-3-oxo-N-(4-methylphenyl)butane amide Yield: 86% Melting point: 196–198° C. $^1$H NMR (DMSO-d$_6$) δ 2.24 (s, 3H, ArCH$_3$), 3.61 (s, 3H, 3-CH$_3$), 3.93 (s, 2H, 4-CH$_2$), 6.76 (s, 1H, 5-vinyl H), 7.10~7.83 (m, 7H, ArH), 10.32 (s, 1H, NH); IR(KBr) 3425 (NH), 1656 (C=O) cm$^{-1}$.

[Compound 50]

2-(4-chloro-2-fluorophenylimino)-3-methyl-4-[N-(4-methylphenyl)carbamoylmethyl]-1,3-thiazol-4-ine hydrobromide (R1=4-CH$_3$, R$_2$=4-Cl, 2-F, R$_3$=CH$_3$, HX=HBr).

Starting materials: methylisothiocyanate, 4-chloro-2-fluoroaniline, 4-bromo-3-oxo-N-(4-methylphenyl)butane amide Yield: 99% Melting point: 206–208° C. $^1$H NMR (DMSO-d$_6$) δ 2.25 (s, 3H, ArCH$_3$), 3.68 (s, 3H, 3-CH$_3$), 3.98 (s, 2H, 4-CH$_2$), 6.96 (s, 1H, 5-vinyl H), 7.11~7.68 (m, 7H, ArH), 10.35 (s, 1H, NH); IR(KBr) 3415 (NH), 1670 (C=O) cm$^{-1}$.

[Compound 51]

2-(3-chloro-4-fluorophenylimino)-3-methyl-4-[N-(4-methylphenyl)carbamoylmethyl]-1,3-thiazol-4-ine hydrobromide (R1=4-CH$_3$, R$_2$=3-Cl, 4-F, R$_3$=CH$_3$, HX=HBr).

Starting materials: methylisothiocyanate, 3-chloro-4-fluoroaniline, 4-bromo-3-oxo-N-(4-methylphenyl)butane amide Yield: 87% Melting point: 242–243° C. $^1$H NMR (DMSO-d$_6$) δ 2.25 (s, 3H, ArCH$_3$), 3.69 (s, 3H, 3-CH$_3$), 4.01 (s, 2H, 4-CH$_2$), 7.02 (s, 1H, 5-vinyl H), 7.11~7.80 (m, 7H, ArH), 10.36 (s, 1H, NH); IR(KBr) 3455 (NH), 1656 (C=O) cm$^{-1}$.

[Compound 52]

2-(2-fluoro-5-methylphenylimino)-3-methyl-4-[N-(4-methylphenyl)carbamoylmethyl]-1,3-thiazol-4-ine hydrobromide (R1=2-F, 5-CH$_3$, R$_2$=4-CH$_3$, R$_3$=CH$_3$, HX=HBr).

Starting materials: methylisothiocyanate, 2-fluoro-5-methylaniline, 4-bromo-3-oxo-N-(4-methylphenyl)butane amide Yield: 41% Melting point: 186–190° C. $^1$H NMR (DMSO-d$_6$) δ 2.25 and 2.32 (2s, 6H, 2×ArCH$_3$), 3.71 (s, 3H, 3-CH$_3$), 4.01 (s, 2H, 4-CH$_2$), 7.03 (s, 1H, 5-vinyl H), 7.11~7.51 (m, 8H, ArH), 10.38 (s, 1H, NH); IR(KBr) 3405 (NH), 1672 (C=O) cm$^{-1}$.

[Compound 53]
2-(4-chloro-3-trifluoromethylphenylimino)-3-methyl-4-[N-(4-methylphenyl)carbamoylmethyl]-1,3-thiazol-4-ine hydrobromide (R1=4-CH$_3$, R$_2$=4-Cl, 3-CF$_3$, R$_3$=CH$_3$, HX=HBr).

Starting materials: methylisothiocyanate, 4-chloro-3-trifluoromethylaniline, 4-bromo-3-oxo-N-(4-methylphenyl)butane amide Yield: 82% Melting point: 230–231° C. $^1$H NMR (DMSO-d$_6$) δ 2.24 (s, 3H, ArCH$_3$), 3.69 (s, 3H, 3-CH$_3$), 4.01 (s, 2H, 4-CH$_2$), 7.01 (s, 1H, 5-vinyl H), 7.11~7.95 (m, 7H, ArH), 10.36 (s, 1H, NH); IR(KBr) 3445 (NH), 1660 (C=O) cm$^{-1}$.

[Compound 54]
2-(3,5-ditrifluoromethylphenylimino)-3-methyl-4-[N-(4-methylphenyl)carbamoylmethyl]-1,3-thiazol-4-ine hydrobromide (R1=4-CH$_3$, R$_2$=3-CF$_3$, 5-CF$_3$, R$_3$=CH$_3$, HX=HBr).

Starting materials: methylisothiocyanate, 3,5-ditrifluoromethylaniline, 4-bromo-3-oxo-N-(4-methylphenyl)butane amide Yield: 94% Melting point: 205–206° C. $^1$H NMR (DMSO-d$_6$) δ 2.24 (s, 3H, ArCH$_3$), 3.62 (s, 3H, 3-CH$_3$), 3.96 (s, 2H, 4-CH$_2$), 6.82 (s, 1H, 5-vinyl H), 7.11~7.99 (m, 7H, ArH), 10.32 (s, 1H, NH); IR(KBr) 3415 (NH), 1684 (C=O) cm$^{-1}$.

[Compound 55]
2-(2-fluoro-4-nitrophenylimino)-3-methyl-4-[N-(4-methylphenyl)carbamoylmethyl]-1,3-thiazol-4-ine hydrobromide (R1=4-CH$_3$, R$_2$=2-F, 4-CH$_3$, R$_3$=CH$_3$, HX=HBr).

Starting materials: methylisothiocyanate, 2-fluoro-4-nitroaniline, 4-bromo-3-oxo-N-(4-methylphenyl)butane amide Yield: 40% Melting point: 258–260° C. $^1$H NMR (DMSO-d$_6$) δ 2.50 (s, 3H, ArCH$_3$), 2.98 (s, 3H, 3-CH$_3$), 2.99 (s, 2H, 4-CH$_2$), 6.93 (s, 1H, 5-vinyl H), 7.26~7.97 (m, 7H, ArH), 10.47 (s, 1H, NH); IR(KBr) 3445 (NH), 1640 (C=O) cm$^{-1}$.

[Compound 56]
2-[4-(n-butyl)phenylimino]-3-methyl-4-[N-(3-chlorophenyl)carbamoylmethyl]-1,3-thiazol-4-ine hydrobromide (R1=4Cl, R$_2$=4-(CH$_2$)$_3$CH$_3$, R$_3$=CH$_3$, HX=HBr).

Starting materials: methylisothiocyanate, 4-(n-butyl)aniline, 4-bromo-3-oxo-N-(3-chlorophenyl)butane amide Yield: 49% Melting point: 223–224° C. $^1$H NMR (DMSO-d$_6$) δ 0.91 (m, 3H, n-butyl CH$_3$), 1.30 (m, 2H, CH$_2$), 1.53 (m, 2H, CH$_2$), 2.50 (m, 2H, CH$_2$), 3.39 (s, 3H, 3-CH$_3$), 4.02 (s, 2H, 4-CH$_2$), 6.98 (s, 1H, 5-vinyl H), 7.14~7.47 (m, 8H, ArH), 10.59 (s, 1H, NH); IR(KBr) 3462 (NH), 1653 (C=O) cm$^{-1}$.

[Compound 57]
2-(4-cyanophenylimino)-3-methyl-4-[N-(3-chlorophenyl)carbamoylmethyl]-1,3-thiazol-4-ine hydrobromide (R1=3-Cl, R$_2$=4-CN, R$_3$=CH$_3$, HX=HBr).

Starting materials: methylisothiocyanate, 4-cyanoaniline, 4-bromo-3-oxo-N-(3-chlorophenyl)butane amide Yield: 58% Melting point: 198–200° C. $^1$H NMR (DMSO-d$_6$) δ 3.66 (s, 3H, 3-CH$_3$), 4.03 (s, 2H, 4-CH$_2$), 6.98 (s, 1H, 5-vinyl H), 7.12~7.94 (m, 8H, ArH), 10.65 (s, 1H, NH); IR(KBr) 3395 (NH), 1686 (C=O) cm$^{-1}$.

[Compound 58]
2-(4-trifluoromethoxyphenylimino)-3-methyl-4-[N-(3-chlorophenyl)carbamoylmethyl]-1,3-thiazol-4-ine hydrobromide (R1=3-Cl, R$_2$=4-OCF$_3$, R$_3$=CH$_3$, HX=HBr).

Starting materials: methylisothiocyanate, 4-trifluoromethoxyaniline, 4-bromo-3-oxo-N-(3-chlorophenyl)butane amide Yield: 41% Melting point: 228° C. $^1$H NMR (DMSO-d$_6$) δ 3.68 (s, 3H, 3-CH$_3$), 4.04 (s, 2H, 4-CH$_2$), 7.01 (s, 1H, 5-vinyl H), 7.13~7.84 (m, 8H, ArH), 10.64 (s, 1H, NH); IR(KBr) 3445 (NH), 1666 (C=O) cm$^{-1}$.

[Compound 59]
2-(3-fluorophenylimino)-3-methyl-4-[N-(3-chlorophenyl)carbamoylmethyl]-1,3-thiazoyl-4-ine hydrobromide (R1=3-Cl, R$_2$=3-F, R$_3$=CH$_3$, HX=HBr).

Starting materials: methylisothiocyanate, 3-fluoroaniline, 4-bromo-3-oxo-N-(3-chlorophenyl)butane amide Yield: 48% Melting point: 226° C. $^1$H NMR (DMSO-d$_6$) δ 3.70 (s, 3H, 3-CH$_3$), 4.06 (s, 2H, 4-CH$_2$), 7.05 (s, 1H, 5-vinyl H), 7.13~7.83 (m, 8H, ArH), 10.66 (s, 1H, NH); IR(KBr) 3425 (NH), 1664 (C=O) cm$^{-1}$.

[Compound 60]
2-(2,4-dichloromethylphenylimino)-3-methyl-4-[N-(3-chlorophenyl)carbamoylmethyl]-1,3-thiazol-4-ine hydrobromide (R1=3-Cl, R$_2$=2-Cl, 4-Cl, R$_3$=CH$_3$, HX=HBr).

Starting materials: methylisothiocyanate, 2,4-dichloromethylaniline, 4-bromo-3-oxo-N-(3-chlorophenyl)butane amide Yield: 41% Melting point: 139–142° C. $^1$H NMR (DMSO-d$_6$) δ 3.58 (s, 3H, 3-CH$_3$), 3.94 (s, 2H, 4-CH$_2$), 6.71 (s, 1H, 5-vinyl H), 7.09~7.82 (m, 7H, ArH), 10.58 (s, 1H, NH); IR(KBr) 3424 (NH), 1656 (C=O) cm$^{-1}$.

[Compound 61]
2-(4-chloro-2-methylphenylimino)-3-methyl-4-[N-(3-chlorophenyl)carbamoylmethyl]-1,3-thiazol-4-ine hydrobromide (R1=3-Cl, R$_2$=4-Cl, 2-CH$_3$, R$_3$=CH$_3$, HX=HBr).

Starting materials: methylisothiocyanate, 4-chloro-2-methylaniline, 4-bromo-3-oxo-N-(3-chlorophenyl)butane amide Yield: 49% Melting point: 219–220° C. $^1$H NMR (DMSO-d$_6$) δ 2.25 (s, 3H, ArCH$_3$), 3.67 (s, 3H, 3-CH$_3$), 4.01 (s, 2H, 4-CH$_2$), 6.93 (s, 1H, 5-vinyl H), 7.13~7.85 (m, 7H, ArH), 10.63 (s, 1H, NH).

[Compound 62]
2-(3-chloro-4-methylphenylimino)-3-methyl-4-[N-(3-chlorophenyl)carbamoylmethyl]-1,3-thiazol-4-ine hydrobromide (R1=3-Cl, R$_2$=3-Cl, 4-CH$_3$, R$_3$=CH$_3$, HX=HBr).

Starting materials: methylisothiocyanate, 3-chloro-4-methylaniline, 4-bromo-3-oxo-N-(3-chlorophenyl)butane amide Yield: 49% Melting point: 213–215° C. $^1$H NMR (DMSO-d$_6$) δ 2.36 (s, 3H, ArCH$_3$), 3.69 (s, 3H, 3-CH$_3$), 4.03 (s, 2H, 4-CH$_2$), 7.03 (s, 1H, 5-vinyl H), 7.08~7.81 (m, 7H, ArH), 10.60 (s, 1H, NH).

[Compound 63]
2-(4-chloro-2-methylphenylimino)-3-methyl-4-[N-(3-chlorophenyl)carbamoylmethyl]-1,3-thiazol-4-ine hydrobromide (R1=3-Cl, R$_2$=4-Cl, 2-CH$_3$, R$_3$=CH$_3$, HX=HBr).

Starting materials: methylisothiocyanate, 4-chloro-2-methylaniline, 4-bromo-3-oxo-N-(3-chlorophenyl)butane amide Yield: 52% Melting point: 217–218° C. $^1$H NMR (DMSO-d$_6$) δ 2.27 (s, 3H, ArCH$_3$), 3.72 (s, 3H, 3-CH$_3$), 4.03 (s, 2H, 4-CH$_2$), 7.00 (s, 1H, 5-vinyl H), 7.09~7.83 (m, 7H, ArH), 10.65 (s, 1H, NH).

[Compound 64]
2-(3-chloro-4-fluorophenylimino)-3-methyl-4-[N-(3-chlorophenyl)carbamoylmethyl]-1,3-thiazol-4-ine hydrobromide (R1=3-Cl, $R_2$=3-Cl, 4-F, $R_3$=CH$_3$, HX=HBr).

Starting materials: methylisothiocyanate, 3-chloro-4-fluoroaniline, 4-bromo-3-oxo-N-(3-chlorophenyl)butane amide Yield: 49% Melting point: 210–211° C. $^1$H NMR (DMSO-d$_6$) δ 3.65 (s, 3H, 3-CH$_3$), 4.02 (s, 2H, 4-CH$_2$), 6.97 (s, 1H, 5-vinyl H), 7.11~7.82 (m, 7H, ArH), 10.62 (s, 1H, NH); IR(KBr) 3425 (NH), 1680 (C=O) cm$^{-1}$.

[Compound 65]
2-(2-methoxyphenylimino)-3-methyl-4-[N-(3-trifluoromethylphenyl)carbamoylmethyl]-1,3-thiazol-4-ine hydrobromide (R1=3-CF$_3$, $R_2$=2-OCH$_3$, $R_3$=CH$_3$, HX=HBr).

Starting materials: methylisothiocyanate, 2-methoxyaniline, 4-bromo-3-oxo-N-(3-trifluoromethylphenyl)butane amide Yield: 50% Melting point: 153–154° C. $^1$H NMR (DMSO-d$_6$) δ 3.30 (s, 3H, 3-OCH$_3$), 3.71 (s, 3H, 3-CH$_3$), 3.82 (s, 2H, 4-CH$_2$), 6.02 (s, 1H, 5-vinyl H), 6.82–7.78 (m, 8H, ArH), 10.59 (s, 1H, NH); IR(KBr) 3430 (NH), 1675 (C=O) cm$^{-1}$.

[Compound 66]
2-(4-chloro-2-fluorophenylimino)-3-methyl-4-[N-(3-chlorophenyl)carbamoylmethyl]-1,3-thiazol-4-ine hydrobromide (R1=3-Cl, $R_2$=4-Cl, 2-F, $R_3$=CH$_3$, HX=HBr).

Starting materials: methylisothiocyanate, 4-chloro-2-fluoroaniline, 4-bromo-3-oxo-N-(3-chlorophenyl)butane amide Yield: 33% Melting point: 141–143° C. $^1$H NMR (DMSO-d$_6$) δ 3.34 (s, 3H, 3-CH$_3$), 3.75 (s, 2H, 4-CH$_2$), 6.15 (s, 1H, 5-vinyl H), 7.00–7.81 (m, 7H, ArH), 10.45 (s, 1H, NH); IR(KBr) 3420 (NH) 1672 (C=O) cm$^{-1}$.

[Compound 67]
2-(2-fluoro-4-methylphenylimino)-3-methyl-4-[N-(3-chlorophenyl)carbamoylmethyl]-1,3-thiazol-4-ine hydrobromide (R1=3-Cl, $R_2$=2-F, 4-CH$_3$, $R_3$=CH$_3$, HX=HBr).

Starting materials: methylisothiocyanate, 2-fluoro-4-methylaniline, 4-bromo-3-oxo-N-(3-chlorophenyl)butane amide Yield: 31% Melting point: 143–144° C. $^1$H NMR (DMSO-d$_6$) δ 2.32 (s, 3H, ArCH$_3$), 3.66 (s, 3H, 3-CH$_3$), 4.01 (s, 2H, 4-CH$_2$), 6.94 (s, 1H, 5-vinyl H), 7.13~7.83 (m, 7H, ArH), 10.62 (s, 1H, NH).

[Compound 68]
2-(2,4-difluorophenylimino)-3-methyl-4-[N-(3-chlorophenyl)carbamoylmethyl]-1,3-thiazol-4-ine hydrobromide (R1=3-Cl, $R_2$=2-F 4-F, $R_3$=CH$_3$, HX=HBr).

Starting materials: methylisothiocyanate, 2,4-difluoroaniline, 4-bromo-3-oxo-N-(3-chlorophenyl)butane amide Yield: 18% Melting point: 136° C. $^1$H NMR (DMSO-d$_6$) δ 3.66 (s, 3H, 3-CH$_3$), 4.01 (s, 2H, 4-CH$_2$), 6.93 (s, 1H, 5-vinyl H), 7.03–7.51 (m, 7H, ArH), 9.19 (s, 1H, NH).

[Compound 69]
2-(4-chloro-2-fluoro-5-isoproxyphenylimino)-3-methyl-4-(N-phenylcarbamoylmethyl)-1,3-thiazol-4-ine hydrobromide (R1=H, $R_2$=4-Cl, 2-F, 5-OCH(CH$_3$)$_2$, $R_3$=CH$_3$, HX=HBr).

Starting materials: methylisothiocyanate, 4-chloro-2-fluoro-5-isoproxyaniline, 4-bromo-3-oxo-N-phenylbutane amide Yield: 79% Melting point: 206–208° C. $^1$H NMR (DMSO-d$_6$) δ 1.29 (d, 6H, (CH$_3$)$_2$), 3.62 (s, 3H, 3-CH$_3$), 3.96 (s, 2H, 4-CH$_2$), 4.58 (m, 1H, OCH), 6.85 (s, 1H, 5-vinyl H), 7.07~7.67 (m, 7H, ArH), 10.40 (s, 1H, NH).

[Compound 70]
2-(4-chloro-2-fluoro-5-(3,3,-dimethylallyloxy)phenylimino)-3-methyl-4-(N-phenylcarbamoylmethyl)-1,3-thiazol-4-ine hydrobromide (R1=H, $R_2$=4-Cl, 2-F, 5-OCH$_2$CH=C(CH$_3$)$_2$, $R_3$=CH$_3$, HX=HBr).

Starting materials: methylisothiocyanate, 4-chloro-2-fluoro-5-(3,3,-dimethylallyloxy)aniline, 4-bromo-3-oxo-N-phenylbutane amide Yield: 72% Melting point: 169–177° C. $^1$H NMR (DMSO-d$_6$) δ 1.69 and 1.75 (2s, 6H, 2×CH$_3$), 2.50 (m, 2H, OCH$_2$), 3.42 (s, 3H, 3-CH$_3$), 3.86 (s, 2H, 4-CH$_2$), 5.41 (m, 1H, CH=), 6.71 (s, 1H, 5-vinyl H), 7.03~7.68 (m, 7H, ArH), 10.50 (s, 1H, NH).

[Compound 71]
2-phenylimino-3-methyl-4-(N-phenylcarbamoylmethyl)-1,3-thiazol-4-ine hydrobromide (R1=H, $R_2$=H, $R_3$=CH$_3$, HX=HBr).

Starting materials: methylisothiocyanate, aniline, 4-bromo-3-oxo-N-phenylbutane amide Yield: 97% Melting point: 253–254° C. $^1$H NMR (DMSO-d$_6$) δ 3.73 (s, 3H, 3-CH$_3$), 4.05 (s, 2H, 4-CH$_2$), 7.05 (s, 1H, vinyl H), 7,08–7.63 (m, 10H, ArH), 10.45 (s, 1H, NH); IR(KBr) 3145 (NH), 1686 (C=O) cm$^{-1}$.

[Compound 72]
2-(3-fluoro-4-methylphenyl)imino-3-methyl-4-N-(4-methoxyphenylcarbamoylmethyl)-1,3-thiazol-4-ine hydrochloride (R1=4-OCH$_3$, $R_2$=3-F, 4-CH$_3$, $R_3$=CH$_3$, HX=HCl).

Starting materials: methylisothiocyanate, 3-fluoro-4-methylaniline, 4-chloro-3-oxo-N-(4-methoxyphenyl)butane amide Yield: 38% Melting point: 241–244° C. $^1$H NMR (DMSO-d$_6$) δ 2.26 (s, H, ArCH$_3$), 3.71 (s, 3H, 3-CH$_3$), 3.79 (s, 3H, OCH$_3$), 4.02 (s, 2H, 4-CH$_2$), 7.05 (s, 1H, 5-vinyl H), 6.87–7.57 (m, 7H, ArH), 10.65 (s, 1H, NH).

[Compound 73]
2-(3-trifluoromethylphenylimino)-3-methyl-4-[N-(2-fluorophenyl)carbamoylmethyl]-1,3-thiazol-4-ine hydrochloride (R1=2-F, $R_2$=3-CF$_3$, $R_3$=CH$_3$, HX=HCl).

Starting materials: methylisothiocyanate, 3-trifluoromethylaniline, 4-chloro-3-oxo-N-(2-fluorophenyl)butane amide Yield: 61% Melting point: 187–193° C. $^1$H NMR (DMSO-d$_6$) δ 3.79 (s, 3H, 3-CH$_3$), 4.08 (s, 2H, 4-CH$_2$), 7.02 (s, 1H, 5-vinyl H), 7.13~7.85 (m, 8H, ArH), 10.24 (s, 1H, NH).

[Compound 74]
2-(2,4-dimethylphenylimino)-3-methyl-4-[N-(2-fluorophenyl)carbamoylmethyl]-1,3-thiazol-4-ine hydrochloride (R1=2-F, $R_2$=2-CH$_3$, 4-CH$_3$, $R_3$=CH$_3$, HX=HCl).

Starting materials: methylisothiocyanate; 2,4-dimethylaniline, 4-chloro-3-oxo-N-(2-fluorophenyl)butane amide Yield: 77% Melting point: 198–205° C. $^1$H NMR (DMSO-d$_6$) δ 2.23 and 2.32 (s, 6H, 2×ArCH$_3$), 3.80 (s, 3H, 3-CH$_3$), 4.07 (s, 2H, 4-CH$_2$), 6.98 (s, 1H, 5-vinyl H), 7.13~7.86 (m, 7H, ArH), 10.30 (s, 1H NH).

[Compound75].
2-(3,5-dichlorophenylimino)-3-methyl-4-[N-(2-fluorophenyl)carbamoylmethyl]-1,3-thiazol-4-ine hydrochloride (R1=2-F, $R_2$=3-Cl, 5-Cl, $R_3$=CH$_3$, HX=HCl).

Starting materials: methylisothiocyanate, 3,5-dichloroaniline, 4-chloro-3-oxo-N-(2-fluorophenyl)butane amide Yield: 80% Melting point: 222–224° C. $^1$H NMR (DMSO-d$_6$) δ 3.70 (s, 3H, 3-CH$_3$), 4.03 (s, 2H, 4-CH$_2$), 6.93 (s, 1H, 5-vinyl H), 7.11~7.87 (m, 7H, ArH), 10.20 (s, 1H, NH).

[Compound 76]
2-(3-fluorophenylimino)-3-methyl-4-[N-(2-fluorophenyl)carbamoylmethyl]-1,3-thiazol-4-ine hydrochloride (R1=2-F, R$_2$=3-F, R$_3$=CH$_3$, HX=HCl).
Starting materials: methylisothiocyanate, 3-fluoroaniline, 4-chloro-3-oxo-N-(2-fluorophenyl)butane amide
Yield: 75% Melting point: 201–202° C. $^1$H NMR (DMSO-d$_6$) δ 3.89 (s, 3H, 3-CH$_3$), 4.08 (s, 2H, 4-CH$_2$), 7.03 (s, 1H, 5-vinyl H), 7.05~7.86 (m, 8H, ArH), 10.26 (s, 1H, NH).

[Compound 77]
2-[4-(n-butyl)phenylimino]-3-methyl-4-[N-(2-fluorophenyl)carbamoylmethyl]-1,3-thiazol-4-ine hydrochloride (R1=2-F, R$_2$=4-(CH$_2$)$_3$CH$_3$, R$_3$=CH$_3$, HX=HCl)
Starting materials: methylisothiocyanate, 4-(n-butyl)aniline, 4-chloro-3-oxo-N-(2-fluorophenyl)butane amide
Yield: 97% Melting point: 189–195° C. $^1$H NMR (DMSO-d$_6$) δ 0.90 (t, 3H, CH$_3$), 1.31 (m, 2H, CH$_2$), 1.57 (m, 2H, CH$_2$), 2.61 (t, 2H, CH$_2$), 3.80 (s, 3H, 3-CH$_3$), 4.09 (s, 2H, 4-CH$_2$), 7.03 (s, 1H, 5-vinyl H). 7.16~7.41 (m, 8H, ArH), 10.29 (s, 1H, NH).

[Compound 78]
2-(4-methoxyphenylimino)-3-methyl-4-[N-(2-fluorophenyl)carbamoylmethyl]-1,3-thiazol-4-ine hydrochloride (R1=2-F, R$_2$=4-OCH$_3$, R$_3$=CH$_3$, HX=HCl).
Starting materials: methylisothiocyanate, 4-methoxyaniline, 4-chloro-3-oxo-N-(2-fluorophenyl)butane amide
Yield: 93% Melting point: 254–255° C. $^1$H NMR (DMSO-d$_6$) δ 3.77 (s, 3H, 3-CH$_3$), 3.80 (s, 3H, 3-OCH$_3$), 4.08 (s, 2H, 4-CH$_2$), 7.01 (s, 1H, 5-vinyl H), 7.05~7.86 (m, 8H, ArH), 10.29 (s, 1H, NH).

[Compound 79]
2-(4-trifluoromethoxyphenylimino)-3-methyl-4-[N-(2-fluorophenyl)carbamoylmethyl]-1,3-thiazol-4-ine hydrochloride (R1=2-F, R$_2$=4-OCF$_3$, R$_3$=CH$_3$, HX=HCl).
Starting materials: methylisothiocyanate, 4-trifluoromethoxyaniline, 4-chloro-3-oxo-N-(2-fluorophenyl)butane amide
Yield: 25% Melting point: 200–207° C. $^1$H NMR (DMSO-d$_6$) δ 3.78 (s, 3H, 3-CH$_3$), 4.08 (s, 2H, 4-CH$_2$), 7.03 (s, 1H, 5-vinyl H), 7.13~7.91 (m, 8H, ArH), 10.23 (s, 1H, NH).

[Compound 80]
2-(4-chloro-2-methylphenylimino)-3-methyl-4-[N-(2-fluorophenyl)carbamoylmethyl]-1,3-thiazol-4-ine hydrochloride (R1=2-F, R$_2$=4-Cl, 2-CH$_3$, R$_3$=CH$_3$, HX=HCl).
Starting materials: methylisothiocyanate, 4-chloro-2-methylaniline, 4-chloro-3-oxo-N-(2-fluorophenyl)butane amide
Yield: 94% Melting point: 190–201° C. $^1$H NMR (DMSO-d$_6$) δ 2.28 (s, 3H, ArCH$_3$), 3.83 (s, 3H, 3-CH$_3$), 4.05 (s, 2H, 4-CH$_2$), 6.90 (s, 1H, 5-vinyl H), 7.11~7.89 (m, 7H, ArH), 10.23 (s, 1H, NH).

[Compound 81]
2-(4-chloro-3-trifluoromethylphenylimino)-3-methyl-4-[N-(2-fluorophenyl)carbamoylmethyl]-1,3-thiazol-4-ine hydrochloride (R1=2-F, R$_2$=4-Cl, 3-CF$_3$, R$_3$=CH$_3$, HX=HCl).
Starting materials: methylisothiocyanate, 4-chloro-3-trifluoromethylaniline, 4-chloro-3-oxo-N-(2-fluorophenyl)butane amide
Yield: 80% Melting point: 201–204° C. $^1$H NMR (DMSO-d$_6$) δ 3.69 (s, 3H, 3-CH$_3$), 4.05 (s, 2H, 4-CH$_2$), 6.90 (s, 1H, 5-vinyl H), 7.17~7.91 (m, 7H, ArH), 10.26 (s, 1H, NH).

[Compound 82]
2-(4-cyanophenylimino)-3-methyl-4-[N-(2-fluorophenyl)carbamoylmethyl]-1,3-thiazol-4-ine hydrochloride (R1=2-F, R$_2$=4-CN, R$_3$=CH$_3$, HX=HCl).
Starting materials: methylisothiocyanate, 4-cyanoaniline, 4-chloro-3-oxo-N-(2-fluorophenyl)butane amide
Yield: 88% Melting point: 224–227° C. $^1$H NMR (DMSO-d$_6$) δ 3.68 (s, 3H, 3-CH$_3$), 4.04 (s, 2H, 4-CH$_2$), 6.88 (s, 1H, 5-vinyl H), 7.17~7.91 (m, 8H, ArH), 10.24 (s, 1H, NH).

[Compound 83]
2-(4-trifluoromethylphenylimino)-3-methyl-4-[N-(2-fluorophenyl)carbamoylmethyl]-1,3-thiazol-4-ine hydrochloride (R1=2-F, R$_2$=4-CF$_3$, R$_3$=CH$_3$, HX=HCl).
Starting materials: methylisothiocyanate, 4-trifluoromethylaniline, 4-chloro-3-oxo-N-(2-fluorophenyl)butane amide
Yield: 70% Melting point: 215–219° C. $^1$H NMR (DMSO-d$_6$) δ 3.76 (s, 3H, 3-CH$_3$), 4.08 (s, 2H, 4-CH$_2$), 7.00 (s, 1H, 5-vinyl H), 7.17~7.87 (m, 8H, ArH), 10.31 (s, 1H, NH).

[Compound 84]
2-(4-phenoxyphenylimino)-3-methyl-4-[N-(2-fluorophenyl)carbamoylmethyl]-1,3-thiazol-4-ine hydrochloride (R1=2-F, R$_2$=4-OC$_6$H$_5$, R$_3$=CH$_3$, HX=HCl).
Starting materials: methylisothiocyanate, 4-phenoxyaniline, 4-chloro-3-oxo-N-(2-fluorophenyl)butane amide
Yield: 97% Melting point: 212–215° C. $^1$H NMR (DMSO-d$_6$) δ 3.76 (s, 3H, 3-CH$_3$), 4.08 (s, 2H, 4-CH$_2$), 7.01 (s, 1H, 5-vinyl H), 7.07~7.83 (m, 13H, ArH), 10.31 (s, 1H, NH).

[Compound 85]
2-(4-phenylphenylimino)-3-methyl-4-[N-(2-fluorophenyl)carbamoylmethyl]-1,3-thiazol-4-ine hydrochloride (R1=2-F, R$_2$=4-C$_6$H$_5$, R$_3$=CH$_3$, HX=HCl).
Starting materials: methylisothiocyanate, 4-phenylalanine, 4-chloro-3-oxo-N-(2-fluorophenyl)butane amide
Yield: 65% Melting point: 221–222° C. $^1$H NMR (DMSO-d$_6$) δ 3.76 (s, 3H, 3-CH$_3$), 4.08 (s, 2H, 4-CH$_2$), 7.01 (s, 1H, 5-vinyl H), 7.07~7.84 (m, 13H, ArH), 10.31 (s, 1H, NH).

[Compound 86]
2-(3-isopropoxyphenylimino)-3-methyl-4-[N-(2-fluorophenyl)carbamoylmethyl]-1,3-thiazol-4-ine hydrochloride (R1=2-F, R$_2$=3-OCH(CH$_3$)$_2$, R$_3$=CH$_3$, HX=H
Starting materials: methylisothiocyanate, 3-isopropoxyaniline, 4-chloro-3-oxo-N-(2-fluorophenyl)butane amide
Yield: 84% Melting point: 184–287° C. $^1$H NMR (DMSO-d$_6$) δ 1.28 (d, 6H, isoproxy (CH$_3$)$_2$), 3.79 (s, 3H, 3-CH$_3$), 4.10 (s, 2H, 4-CH$_2$), 4.61 (m, 1H, isoproxy CH), 6.90 (s, 1H, 5-vinyl H), 6.94~7.83 (m, 8H, ArH), 10.34 (s, 1H, NH).

[Compound 87]
2-(3-methoxyphenylimino)-3-methyl-4-[N-(2-fluorophenyl)carbamoylmethyl]-1,3-thiazol-4-ine hydrochloride (R1=2-F, R$_2$=4-OCH$_3$, R$_3$=CH$_3$, HX=HCl).
Starting materials: methylisothiocyanate, 3-methoxyaniline, 4-chloro-3-oxo-N-(2-fluorophenyl)butane amide
Yield: 91% Melting point: 163–165° C. $^1$H NMR (DMSO-d$_6$) δ 3.78 (s, 3H, 3-CH$_3$), 3.79 (s, 3H, 4-OCH$_3$) 4.09 (s, 2H, 4-CH$_2$), 7.04 (s, 1H, 5-vinyl H), 6.95~7.83 (m, 8H, ArH), 10.32 (s, 1H, NH).

[Compound 88]
2-(4-chlorophenylimino)-3-methyl-4-{N-(2-fluorophenyl)carbamoylmethyl]-1,3-thiazol-}4-ine hydrochloride (R1=2-F, R$_2$=4-Cl, R$_3$=CH$_3$, HX=HCl).
Starting materials: methylisothiocyanate, 4-chloroaniline, 4-chloro-3-oxo-N-(2-fluorophenyl)butane amide Yield: 51% Melting point: 224–226° C. $^1$H NMR (DMSO-$d_6$) δ 3.76 (s, 3H, 3-CH$_3$), 4.09 (s, 2H, 4-CH$_2$), 7.02 (s, 1H, 5-vinyl H), 7.16~7.84 (m, 8H, ArH), 10.81 (s, 1H, NH).

[Compound 89]
2-(2-fluorophenylimino)-3-methyl-4-[N-(2-fluorophenyl)carbamoylmethyl]-1,3-thiazol-4-ine hydrochloride (R1=2-F, R$_2$=2-F, R$_3$=CH$_3$, HX=HCl).

Starting materials: methylisothiocyanate, 2-fluoroaniline, 4-chloro-3-oxo-N-(2-fluorophenyl)butane amide Yield: 99% Melting point: 179–183° C. $^1$H NMR (DMSO-$d_6$) δ 3.72 (s, 3H, 3-CH$_3$), 4.05 (s, 2H, 4-CH$_2$), 6.90 (s, 1H, 5-vinyl H), 7.16~7.84 (m, 8H, ArH), 10.29 (s, 1H, NH).

[Compound 90]
2-(3-chlorophenylimino)-3-methyl-4-[N-(2-fluoro)phenylcarbamoylmethyl]-1,3-thiazol-4-ine hydrochloride (R1=4-Cl, R$_2$=3-Cl, R$_3$=CH$_3$, HX=HCl).

Starting materials: methylisothiocyanate, 3-chloroaniline, 4-chloro-3-oxo-N-(2-fluorophenyl)butane amide Yield: 58% Melting point: 171–173° C. $^1$H NMR (DMSO-$d_6$) δ 3.75 (s, 3H, 3-CH$_3$), 4.08 (s, 2H, 4-CH$_2$), 7.00 (s, 1H, 5-vinyl H), 7.16~7.84 (m, 8H, ArH), 10.29 (s, 1H, NH).

[Compound 91]
2-(4-cyanophenylimino)-3-methyl-4-[N-(2,4,6-trichlorophenyl)carbamoylmethyl]-1,3-thiazol-4-ine hydrochloride (R1=2-Cl, 4-Cl, 6-Cl, R$_2$=4-CN, R$_3$=CH$_3$, HX=HCl).

Starting materials: methylisothiocyanate, 4-cyanoaniline, 4-chloro-3-oxo-N-(2,4,6-trichlorophenyl)butane amide Yield: 66% Melting point: 237–241° C. $^1$H NMR (DMSO-$d_6$) δ 3.66 (s, 3H, 3-CH$_3$), 4.01 (s, 2H, 4-CH$_2$), 6.85 (s, 1H, 5-vinyl H), 7.48~7.89 (m, 6H, ArH), 10.47 (s, 1H, NH).

[Compound 92]
2-(4-cyanophenylimino)-3-methyl-4[N-(4-trifluoromethoxyphenyl)carbamoylmethyl]-1,3-thiazol-4-ine hydrochloride (R1=OCF$_3$, R$_2$=4-CN, R$_3$=CH$_3$, HX=HCl).

Starting materials: methylisothiocyanate, 4-cyanoaniline, 4-chloro-3-oxo-N-(4-trifluoromethoxyphenyl)butane amide Yield: 67% Melting point: 212–213° C. $^1$H NMR (DMSO-$d_6$) δ 3.70 (s, 3H, 3-CH$_3$), 4.02 (s, 2H, 4-CH$_2$), 6.94 (s, 1H, 5-vinyl H), 7.31~7.92 (m, 8H, ArH), 10.90 (s, 1H, NH).

[Compound 93]
2-(3,5-dichlorophenylimino)-3-methyl-4-[N-(2,4,6-trichlorophenyl)carbamoylmethyl]-1,3-thiazol-4-ine hydrochloride (R1=2-Cl, 4-Cl, 6-Cl, R$_2$=3-Cl, 5-Cl, R$_3$=CH$_3$, HX=HCl).

Starting materials: methylisothiocyanate, 3,5-dichloroaniline, 4-chloro-3-oxo-N-(2,4,6-trichlorophenyl)butane amide Yield: 29% Melting point: 218–222° C. $^1$H NMR (DMSO-$d_6$) δ 3.67 (s, 3H, 3-CH$_3$), 4.02 (s, 2H, 4-CH$_2$), 6.88 (s, 1H, 5-vinyl H), 7.45~7.78 (m, 5H, ArH), 10.48 (s, 1H, NH).

[Compound 94]
2-(3,5-dichlorophenylimino)-3-methyl-4-[N-(4-trifluoromethoxyphenyl)carbamoylmethyl]-1,3-thiazol-4-ine hydrochloride (R1=4-OCF$_3$, R$_2$=3-Cl, 5-Cl R$_3$=CH$_3$, HX=HCl).

Starting materials: methylisothiocyanate, 3,5-dichloroaniline, 4-chloro-3-oxo-N-(4-trifluoromethoxyphenyl)butane amide Yield: 43% Melting point: 221° C. $^1$H NMR (DMSO-$d_6$) δ 3.70 (s, 3H, 3-CH$_3$), 4.03 (s, 2H, 4-CH$_2$), 6.94 (s, 1H, 5-vinyl H), 7.32~7.78 (m, 7H, ArH), 10.94 (s, 1H, NH).

[Compound 95]
2-(4-trifluoromethylphenylimino)-3-methyl-4-[N-(4-chlorophenyl)carbamoylmethyl]-1,3-thiazol-4-ine hydrochloride (R1=4Cl, R$_2$=4-CF$_3$, R$_3$=CH$_3$, HX=HCl).

Starting materials: methylisothiocyanate, 4-trifluoromethylaniline, 4-chloro-3-oxo-N-(4-chlorophenyl)butane amide Yield: 99% Melting point: 215–218° C. $^1$H NMR (DMSO-$d_6$) δ 3.64 (s, 3H, 3-CH$_3$), 3.98 (s, 2H, 4-CH$_2$), 6.85 (s, 1H, 5-vinyl H), 7.36~7.67 (m, 8H, ArH), 10.78 (s, 1H, NH).

[Compound 96]
2-(4-trifluoromethylphenylimino)-3-methyl-4-[N-(2,4,6-trichlorophenyl)carbamoylmethyl]-1,3-thiazol-4-ine hydrochloride (R1=2-Cl, 4-Cl, 6-Cl, R$_2$=4-CF$_3$, R$_3$=CH$_3$, HX=HCl).

Starting materials: methylisothiocyanate, 4-trifluoromethylaniline, 4-chloro-3-oxo-N-(2,4,6-trichlorophenyl)butane amide Yield: 71% Melting point: 182–191° C. $^1$H NMR (DMSO-$d_6$) δ 3.74 (s, 3H, 3-CH$_3$), 4.06 (s, 2H, 4-CH$_2$), 6.98 (s, 1H, 5-vinyl H), 7.62~7.85 (m, 6H, ArH), 10.51 (s, 1H, NH).

[Compound 97]
2-(4-trifluoromethylphenylimino)-3-methyl-4-[N-(4-trifluoromethoxyphenyl)carbamoylmethyl]-1,3-thiazol-4-ine hydrochloride (R1=4-OCF$_3$, R$_2$=4-CF$_3$, R$_3$=CH$_3$, HX=HCl).

Starting materials: methylisothiocyanate, 4-trifluoromethylaniline, 4-chloro-3-oxo-N-(4-trifluoromethoxyphenyl)butane amide Yield: 73% Melting point: 223–228° C. $^1$H NMR (DMSO-$d_6$) δ 3.79 (s, 3H, 3-CH$_3$), 4.04 (s, 2H, 4-CH$_2$), 6.99 (s, 1H, 5-vinyl H), 7.32~7.86 (m, 8H, ArH), 10.92 (s, 1H, NH).

[Compound 98]
2-(4-trifluoromethylphenylimino)-3-methyl-4-[N-(4-chlorophenyl)carbamoylmethyl]-1,3-thiazol-4-ine hydrochloride (R1=4-Cl, R$_2$=4-CF$_3$, R$_3$=CH$_3$, HX=HCl).

Starting materials: methylisothiocyanate, 4-trifluoromethylaniline, 4-chloro-3-oxo-N-(4-chlorophenyl)butane amide Yield: 77% Melting point: 220–223° C. $^1$H NMR (DMSO-$d_6$) δ 3.72 (s, 3H, 3-CH$_3$), 4.02 (s, 2H, 4-CH$_2$), 6.97 (s, 1H, 5-vinyl H), 7.36~7.86 (m, 8H, ArH), 10.54 (s, 1H, NH).

[Compound 99]
2-(4-phenoxyphenylimino)-3-methyl-4-[N-(2,4,6-trichlorophenyl)carbamoylmethyl]-1,3-thiazol-4-ine hydrochloride (R1=2-Cl, 4-Cl, 6-Cl, R$_2$=4-OC$_6$H$_5$, R$_3$=CH$_3$, HX=HCl).

Starting materials: methylisothiocyanate, 4-phenoxyaniline, 4-chloro-3-oxo-N-(2,4,6-trichlorophenyl)butane amide Yield: 85% Melting point: 218–220° C. $^1$H NMR (DMSO-$d_6$) δ 3.75 (s, 3H, 3-CH$_3$), 4.08 (s, 2H, 4-CH$_2$), 7.03 (s, 1H, 5-vinyl H), 7.06~7.79 (m,11H, ArH), 10.54 (s, 1H, NH).

[Compound 100]
2-(4-phenoxyphenylimino)-3-methyl-4-[N-(4-trifluoromethoxyphenyl)carbamoylmethyl]-1,3-thiazol-4-ine hydrochloride (R1=OCF$_3$, R$_2$=4-OC$_6$H$_5$, R$_3$=CH$_3$, HX=HCl).

Starting materials: methylisothiocyanate, 4-phenoxyaniline, 4-chloro-3-oxo-N-(4-trifluoromethoxyphenyl)butane amide Yield: 94% Melting point: 242–246° C. $^1$H NMR (DMSO-$d_6$) δ 3.75 (s, 3H, 3-CH$_3$), 4.06 (s, 2H, 4-CH$_2$), 7.03 (s, 1H, 5-vinyl H), 7.07~7.77 (m, 13H, ArH), 10.98 (s, 1H, NH).

[Compound 101]
2-(4-bromophenylimino)-3-methyl-4-[N-(4-trifluoromethoxyphenyl)carbamoylmethyl]-1,3-thiazol-4-ine hydrochloride (R1=4-OCF$_3$, R$_2$=4-Br, R$_3$=CH$_3$, HX=HCl).

Starting materials: methylisothiocyanate, 4-bromoaniline, 4-chloro-3-oxo-N-(4-trifluoromethoxyphenyl)butane amide Yield: 48% Melting point: 215–218° C. $^1$H NMR (DMSO-d$_6$) δ 3.73 (s, 3H, 3-CH$_3$), 4.05 (s, 2H, 4-CH$_2$), 7.02 (s, 1H, 5-vinyl H), 7.33~7.76 (m, 8H, ArH), 10.94 (s, 1H, NH).

[Compound 102]
2-(3,5-dichlorophenylimino)-3-methyl-4-[N-(4-methoxyphenyl)carbamoylmethyl]-1,3-thiazol-4-ine hydrochloride (R1=4-OCH$_3$, R$_2$=2-Cl, 4-Cl, R$_3$=CH$_3$, HX=HCl).

Starting materials: methylisothiocyanate, 3,5-dichloroaniline, 4-chloro-3-oxo-N-(4-methoxyphenyl)butane amide Yield: 53% Melting point: 215–217° C. $^1$H NMR (DMSO-d$_6$) δ 3.66 (s, 3H, 3-CH$_3$), 3.72 (s, 3H, 4-OCH$_3$), 3.99 (s, 2H, 4-CH$_2$), 6.87 (s, 1H, 5-vinyl H), 6.88~7.54 (m, 7H, ArH), 10.43 (s, 1H, NH).

[Compound 103]
2-(2,4-dimethylphenylimino)-3-methyl-4-[N-(2,4,6-trichloromethylphenyl)carbamoylmethyl]-1,3-thiazol-4-ine hydrochloride (R1=2-Cl, 4-Cl, 6-Cl, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(2,4,6-trichloromethylphenyl)butane amide Yield: 59% Melting point: 200–204° C. $^1$H NMR (DMSO-d$_6$) δ 2.22 and 2.32 (2s, 6H, 2×ArCH$_3$, 3.70 (s, 3H, 3-CH$_3$), 4.08 (s, 2H, 4-CH$_2$), 7.01 (s, 1H, 5-vinyl H), 7.16–7.32 (m, 5H, ArH), 10.66 (s, 1H, NH).

[Compound 104]
2-(4-chlorophenylimino)-3-methyl-4-[N-(4-methoxyphenyl)carbamoylmethyl]-1,3-thiazol-4-ine hydrochloride (R1=4-OCH$_3$, R$_2$=4-Cl, R$_3$=CH$_3$, HX=HCl).

Starting materials: methylisothiocyanate, 4-chloroaniline, 4-chloro-3-oxo-N-(4-methoxyphenyl)butane amide Yield: 80% Melting point: 241–244° C. $^1$H NMR (DMSO-d$_6$) δ 3.72 (s, 3H, 3-CH$_3$), 3.75 (s, 3H, OCH$_3$), 3.98 (s, 2H, 4-CH$_2$), 7.00 (s, 1H, 5-vinyl H), 6.86~7.64 (m, 8H, ArH), 10.5 (s, 1H, NH).

[Compound 105]
2-(4-isopropoxyphenylimino)-3-methyl-4-[N-(2-fluorophenyl)carbamoylmethyl]-1,3-thiazol-4-ine hydrochloride (R1=2-F, R$_2$=4-OCH(CH$_3$)$_2$, R$_3$=CH$_3$, Starting materials: methylisothiocyanate, 4-isopropoxyaniline, 4-chloro-3-oxo-N-(2-fluorophenyl)butane amide Yield: 30% Melting point: 209–212° C. $^1$H NMR (DMSO-d$_6$) δ 1.28 (m, 6H, isopropoxy (CH$_3$)$_2$, 3.76 (s, 3H, 3-CH$_3$), 4.09 (s, 2H, 4-CH$_2$), 4.66 (m, 1H, isopropoxy CH), 7.00 (s, 1H, 5-vinyl H), 7.05–7.42 (m, 8H, ArH), 10.3 (s, 1H, NH).

[Compound 106]
2-(4-fluorophenylimino)-3-methyl-4-[N-(2-fluorophenyl)carbamoylmethyl]-1,3-thiazol-4-ine hydrochloride (R1=2-F, R$_2$=4-F, R$_3$=CH$_3$, HX=HCl).

Starting materials: methylisothiocyanate, 4-fluoroaniline, 4-chloro-3-oxo-N-(2-fluorophenyl)butane amide Yield: 48% Melting point: 180–188° C. $^1$H NMR (DMSO-d$_6$) δ 3.77 (s, 3H, 3-CH$_3$), 4.03 (s, 2H, 4-CH$_2$), 6.96 (s, 1H, 5-vinyl H), 7.16–7.59 (m, 8H, ArH), 10.3 (s, 1H, NH).

[Compound 107]
2-(3-nitrophenylimino)-3-methyl-4-[N-(2-fluorophenyl)carbamoylmethyl]-1,3-thiazol-4-ine hydrochloride (R1=2-F, R$_2$=3-NO$_2$, R$_3$=CH$_3$, HX=HCl).

Starting materials: methylisothiocyanate, 3-nitroaniline, 4-chloro-3-oxo-N-(2-fluorophenyl)butane amide Yield: 94% Melting point: 185–189° C. $^1$H NMR (DMSO-d$_6$) δ 3.72 (s, 3H, 3-CH$_3$), 4.07 (s, 2H, 4-CH$_2$), 6.93 (s, 1H, 5-vinyl H), 7.17–8.12 (m, 8H, ArH), 10.26 (s, 1H, NH).

[Compound 108]
2-(4-trifluoromethoxyphenylimino)-3-methyl-4-[N-(4-trifluoromethoxyphenyl)carbamoylmethyl]-1,3-thiazol-4-ine hydrochloride (R1=4-OCF$_3$, R$_2$=4-OCF$_3$, R$_3$=CH$_3$, HX=HCl).

Starting materials: methylisothiocyanate, 4-trifluoromethoxyaniline, 4-chloro-3-oxo-N-(4-trifluoromethoxyphenyl)butane amide Yield: 47% Melting point: 236–239° C. $^1$H NMR (DMSO-d$_6$) δ 3.74 (s, 3H, 3-CH$_3$), 4.05 (s, 2H, 4-CH$_2$), 7.01 (s, 1H, 5-vinyl H), 7.32–7.62 (m, 8H, ArH), 10.9 (s, 1H, NH).

[Compound 109]
2-(3-isopropoxyphenylimino)-3-methyl-4-[N-(4-trifluoromethoxyphenyl)carbamoylmethyl]-1,3-thiazol-4-ine hydrochloride (R1=4-OCF$_3$, R$_2$=OCH(CH$_3$)$_2$, R$_3$=CH$_3$, HX=HCl).

Starting materials: methylisothiocyanate, 3-isopropoxyaniline, 4-chloro-3-oxo-N-(4-trifluoromethoxyphenyl)butane amide Yield: 73% Melting point: 208–210° C. $^1$H NMR (DMSO-d$_6$) δ 1.28 (d, 6H, J=6.0Hz, isopropoxy (CH$_3$)$_2$, 3.75 (s, 3H, 3-CH$_3$), 4.06 (s, 2H, 4-CH$_2$), 4.61 (m, 1H, J=6.0 Hz, isopropoxy CH), 6.93 (s, 1H, 5-vinyl H), 6.94–7.77 (m, 8H, ArH), 10.4 (s, 1H, NH).

[Compound 110]
2-[4-(n-butyl)phenylimino]-3-methyl-4-[N-(4-trifluoromethoxyphenyl)carbamoylmethyl]-1,3-thiazol-4-ine hydrochloride (R1=4-OCF$_3$, R$_2$=4-(CH$_2$)$_3$CH$_3$, R$_3$=CH$_3$, HX=HCl).

Starting materials: methylisothiocyanate, 4-(n-butyl)aniline, 4-chloro-3-oxo-N-(4-trifluoromethoxyphenyl)butane amide Yield: 71% Melting point: 240–243° C. $^1$H NMR (DMSO-d$_6$) δ 0.90 (t, 3H, J=5.4Hz, n-butyl CH$_3$), 1.32 (m, 2H, CH$_2$H, CH$_2$), 1.57 (m, 2H, CH$_2$), 1.62 (t, 2H, J=5.4Hz, CH$_2$), 3.76 (s, 3H, 3-CH$_3$), 4.06 (s, 2H, 4-CH$_2$), 7.03 (s, 1H, 5-vinyl H), 7.35–7.77 (m, 8H, ArH), 11.0 (s, 1H, NH).

[Compound 111]
2-(4-nitrophenylimino)-3-methyl-4-[N-(4-trifluoromethoxyphenyl)carbamoylmethyl]-1,3-thiazol-4-ine hydrochloride (R1=4-OCF$_3$, R$_2$=4-NO$_2$, R$_3$=CH$_3$, HX=HCl).

Starting materials: methylisothiocyanate, 4-nitroaniline, 4-chloro-3-oxo-N-(4-trifluoromethoxyphenyl)butane amide Yield: 756% Melting point: 178–184° C. $^1$H NMR (DMSO-d$_6$) δ 3.64 (s, 3H, 3-CH$_3$), 3.99 (s, 2H, 4-CH$_2$), 6.86 (s, 1H, 5-vinyl H), 7.32–8.29 (m, 8H, ArH), 10.86 (s,1H, NH).

[Compound 112]
2-(3-methoxyphenylimino)-3-methyl-4-[N-(4-trifluoromethoxyphenyl)carbamoylmethyl]-1,3-thiazol-4-ine hydrochloride (R1=4-OCF$_3$, R$_2$=3-OCH$_3$, R$_3$=CH$_3$, HX=HCl).

Starting materials: methylisothiocyanate, 3-methoxyaniline, 4-chloro-3-oxo-N-(4-trifluoromethoxyphenyl)butane amide Yield: 77% Melting point: 233–236° C. $^1$H NMR (DMSO-d$_6$) δ 3.78 (s, 3H, 3-CH$_3$), 4.08 (s, 2H, 4-CH$_2$), 6.95 (s, 1H, 5-vinyl H), 6.98–7.78 (m, 8H, ArH), 11.06 (s, 1H, NH).

[Compound 113]

2-(4-methoxyphenylimino)-3-methyl-4-[N-(4-trifluoromethoxyphenyl)carbamoylmethyl]-1,3-thiazol-4-ine hydrochloride (R1=4-OCF$_3$, R$_2$=4-OCH$_3$, R$_3$=CH$_3$, HX=HCl).

Starting materials: methylisothiocyanate, 4-methoxyaniline, 4-chloro-3-oxo-N-(4-trifluoromethoxyphenyl)butane amide Yield: 55% Melting point: 240–244° C. $^1$H NMR (DMSO-d$_6$) δ 3.74 (s, 3H, 3-CH$_3$), 3.80 (s, 2H, 4-CH$_2$), 7.02 (s, 1H, 5-vinyl H), 7.80–7.77-(m, 8H, ArH), 11.04 (s, 1H, NH).

[Compound 114]

2-(4-chlorophenylimino)-3-methyl-4-[N-(4-trifluoromethoxyphenyl)carbamoylmethyl]-1,3-thiazol-4-ine hydrochloride (R1=4-OCF$_3$, R$_2$=4-Cl, R$_3$=CH$_3$, HX=HCl).

Starting materials: methylisothiocyanate, 4-chloroaniline, 4-chloro-3-oxo-N-(4-trifluoromethoxyphenyl)butane amide Yield: 72% Melting point: 224–228° C. $^1$H NMR (DMSO-d$_6$) δ 3.74 (s, 3H, 3-CH$_3$), 4.05 (s, 2H, 4CH$_2$), 7.03 (s, 1H, 5-vinyl H), 7.32–7.77 (m, 8H, ArH), 10.92 (s, 1H, NH).

[Compound 115]

2-(4-fluorophenylimino)-3-methyl-4-[N-(4-trifluoromethoxyphenyl)carbamoylmethyl]-1,3-thiazol-4-ine hydrochloride (R1=4-OCF$_3$, R$_2$=F, R$_3$=CH$_3$, HX=HCl).

Starting materials: methylisothiocyanate, 4-fluoroaniline, 4-chloro-3-oxo-N-(4-trifluoromethoxyphenyl)butane amide Yield: 57% Melting point: 238–239° C. $^1$H NMR (DMSO-d$_6$) δ 3.75 (s, 3H, 3-CH$_3$), 4.06 (s, 2H, 4-CH$_2$), 7.03 (s, 1H, 5-vinyl H), 7.30–7.78 (m, 8H, ArH), 11.01 (s, 1H, NH).

[Compound 116]

2-(4-phenylphenylimino)-3-methyl-4-[N-(4-trifluoromethoxyphenyl)carbamoylmethyl]-1,3-thiazol-4-ine hydrochloride (R1=4-OCF$_3$, R$_2$=4-C$_6$H$_5$, R$_3$=CH$_3$, HX=HCl).

Starting materials: methylisothiocyanate, 4-phenylaniline, 4-chloro-3-oxo-N-(4-trifluoromethoxyphenyl)butane amide Yield: 66% Melting point: 232–233° C. $^1$H NMR (DMSO-d$_6$) δ 3.75 (s, 3H, 3-CH$_3$), 4.07 (s, 2H, 4-CH$_2$), 7.03 (s, 1H, 5-vinyl H), 7.07–7.78 (m, 13H, ArH), 11.01 (s, 1H, NH).

[Compound 117]

2-(3-trifluoromethylphenylimino)-3-methyl-4-[N-(4-trifluoromethoxyphenyl)carbamoylmethyl]-1,3-thiazol-4-ine hydrochloride (R1=4-OCF$_3$, R$_2$=CF$_3$, R$_3$=CH$_3$, HX=HCl).

Starting materials: methylisothiocyanate, 3-trifluoromethylaniline, 4-chloro-3-oxo-N-(4-trifluoromethoxyphenyl)butane amide Yield: 43% Melting point: 201–204° C. $^1$H NMR (DMSO-d$_6$) δ 3.76(s, 3H, 3-CH$_3$), 4.07 (s, 2H, 4-CH$_2$), 7.02 (s, 1H, 5-vinyl H), 7.32–7.88 (m, 8H, ArH), 11.00 (s, 1H, NH).

[Compound 118]

2-(4-methoxyphenylimino)-3-methyl-4-[N-(4-chlorophenyl)carbamoylmethyl]-1,3-thiazol-4-ine hydrochloride (R1=4-Cl, R$_2$=4-OCH$_3$, R$_3$=CH$_3$, HX=HCl).

Starting materials: methylisothiocyanate, 4-methoxyaniline, 4-chloro-3-oxo-N-(4-chlorophenyl)butane amide Yield: 44% Melting point: 250–253° C. $^1$H NMR (DMSO-d$_6$) δ 3.75 (s, 3H, 3-CH$_3$), 3.80 (s, 3H, OCH$_3$), 4.05 (s, 2H, 4-CH$_2$), 7.01 (s, 1H, 5-vinyl H), 7.08–7.70 (m, 8H, ArH), 11.01 (s, 1H, NH).

[Compound 119]

2-(3-methoxyphenylimino)-3-methyl-4-[N-(4-chlorophenyl)carbamoylmethyl]-1,3-thiazol-4-ine hydrochloride (R1=4-Cl, R$_2$=3-OCH$_3$, R$_3$=CH$_3$, HX=HCl).

Starting materials: methylisothiocyanate, 3-methoxyaniline, 4-chloro-3-oxo-N-(4-chlorophenyl)butane amide Yield: 74% Melting point: 228–231° C. $^1$H NMR (DMSO-d$_6$) δ 3.77 (s, 3H, 3-CH$_3$), 3.78 (s, 3H, OCH$_3$), 4.07 (s, 2H, 4-CH$_2$), 6.96 (s,1H, 5-vinyl H), 7.07–7.70 (m, 8H, ArH), 11.04 (s, 1H, NH).

[Compound 120]

2-(4-phenoxyphenylimino)-3-methyl-4-[N-(4-chlorophenyl)carbamoylmethyl]-1,3-thiazol-4-ine hydrochloride (R1=4-Cl, R$_2$=4-OC$_6$H$_5$, R$_3$=CH$_3$, HX=HCl).

Starting materials: methylisothiocyanate, 4-phenoxyaniline, 4-chloro-3-oxo-N-(4-chlorophenyl)butane amide Yield: 38% Melting point: 238–242° C. $^1$H NMR (DMSO-d$_6$) δ 3.76 (s, 3H, 3-CH$_3$), 4.05 (s, 2H, 4-CH$_2$), 7.03 (s, 1H, 5-vinyl H), 7.10–7.70 (m, 13H, ArH), 10.96 (s, 1H, NH).

[Compound 121]

2-(4-trifluoromethoxyphenylimino)-3-methyl-4-[N-(4-chlorophenyl)carbamoylmethyl]-1,3-thiazol-4-ine hydrochloride (R1=4-Cl, R$_2$=4-OCF$_3$, R$_3$=CH$_3$, HX=HCl).

Starting materials: methylisothiocyanate, 4-trifluoromethoxyaniline, 4-chloro-3-oxo-N-(4-chlorophenyl)butane amide Yield: 20% Melting point: 237–240° C. $^1$H NMR (DMSO-d$_6$) δ 3.75 (s, 3H, 3-CH$_3$), 4,08 (s, 2H, 4-CH$_2$), 6.99 (s, 1H, 5-vinyl H), 7.11–7.89 (m, 8H, ArH), 11.13 (s, 1H, NH).

[Compound 122]

2-(4-chlorophenylimino)-3-methyl-4-[N-(4-chlorophenyl)carbamoylmethyl-1,3-thiazol-]4-ine hydrochloride (R1=4-Cl, R$_2$=4-Cl, R$_3$=CH$_3$, HX=HCl).

Starting materials: methylisothiocyanate, 4-chloroaniline, 4-chloro-3-oxo-N-($^4$-chlorophenyl)butane amide Yield: 90% Melting point: 239–242° C. $^1$H NMR (DMSO-d$_6$) δ 3.76 (s, 3H, 3-CH$_3$), 4.07 (s, 2H, 4-CH$_2$), 7.05 (s, 1H, 5-vinyl H), 7.36–7.70 (m, 8H, ArH), 10.30 (s, 1H, NH).

[Compound 123]

2-(3-isopropoxyphenylimino)-3-methyl-4-[N-(4-chlorophenyl)carbamoylmethyl]-1,3-thiazol-4-ine hydrochloride (R1=4-Cl, R$_2$=3-OCH(CH$_3$)$_2$, R$_3$=CH$_3$, HX=HCl).

Starting materials: methylisothiocyanate, 3-isopropoxyaniline, 4-chloro-3-oxo-N-(4-chlorophenyl)butane amide Yield: 65% Melting point: 201–203° C. $^1$H NMR (DMSO-d$_6$) δ 1.28 (d, 6H, J=6.0 Hz, isopropoxy (CH$_3$)$_2$), 3.78 (s, 3H, 3-CH$_3$), 4.06 (s, 2H, 4-CH$_2$), 4.61 (m, 1H, J=6.0 Hz, isopropoxy CH), 6.93 (s, 1H, 5-vinyl H), 7.01–7.70 (m, 8H, ArH), 10.30 (s, 1H, NH).

[Compound 124]

2-[4-(n-butyl)phenylimino]-3-methyl-4-[N-(4-chlorophenyl)carbamoylmethyl]-1,3-thiazol-4-ine hydrochloride (R1=4-Cl, R$_2$=4-(CH$_2$)$_3$CH$_3$, R$_3$=CH$_3$, HX=HCl)

Starting materials: methylisothiocyanate, 4-(n-butyl) aniline, 4-chloro-3-oxo-N-(4-chlorophenyl)butane amide Yield: 59% Melting point: 239–241° C. $^1$H NMR (DMSO-d$_6$) δ 0.90 (t, 3H, J=7.2 Hz, n-butyl CH$_3$), 1.32 (m, 2H, CH$_2$), 1.57 (m, 2H, CH$_2$), 2.62 (t, 2H, J=7.2 Hz, CH$_2$), 3.78 (s, 3H, 3-CH$_3$), 4.06 (s, 2H, 4-CH$_2$), 7.03 (s, 1H, 5-vinyl H), 7.33–7.70 (m, 8H, ArH), 10.99 (s, 1H, NH).

[Compound 125]

2-(3-nitrophenylimino)-3-methyl-4-[N-(4-chlorophenyl) carbamoylmethyl]-1,3-thiazol-4-ine hydrochloride (R1=4-Cl, R$_2$=3-NO$_2$, R$_3$=CH$_3$, HX=HCl).

Starting materials: methylisothiocyanate, 3-nitroaniline, 4-chloro-3-oxo-N-(4-chlorophenyl)butane amide Yield: 26% Melting point: 228° C. $^1$H NMR (DMSO-d$_6$) δ 3.79 (s, 3H, 3-CH$_3$), 4.04 (s, 2H, 4-CH$_2$), 6.96 (s, 1H, 5-vinyl H), 7.36–8.28 (m, 8H, ArH), 10.83 (s, 1H, NH).

[Compound 126]

2-(3-trifluoromethylphenylimino)-3methyl-4-[N-(4-chlorophenyl)carbamoylmethyl]-1,3-thiazol-4-ine hydrochloride (R1=4-Cl, R$_2$=3-CF$_3$, R$_3$=CH$_3$, HX=HCl).

Starting materials: methylisothiocyanate, 3-trifluoromethylaniline, 4-chloro-3-oxo-N-(4-chlorophenyl)butane amide Yield: 63% Melting point: 204–207° C. $^1$H NMR (DMSO-d$_6$) δ 3.75 (s, 3H, 3-CH$_3$), 4.05 (s, 2H, 4-CH$_2$), 7.00 (s, 1H, 5-vinyl H), 7.36–7.88 (m, 8H, ArH), 10.92 (s, 1H, NH).

[Compound 127]

2-(4-nitrophenylimino)-3-methyl-4-[N-(4-chlorophenyl) carbamoylmethyl]-1,3-thiazol-4-ine hydrochloride (R1=4-Cl, R$_2$=4-NO$_2$, R$_3$=CH$_3$, HX=HCl).

Starting materials: methylisothiocyanate, 4-nitroaniline, 4-chloro-3-oxo-N-(4-chlorophenyl)butane amide Yield: 78% Melting point: 202–205° C. $^1$H NMR (DMSO-d$_6$) δ 3.67 (s, 3H, 3-CH$_3$), 3.99 (s, 2H, 4-CH$_2$), 6.89 (s, 1H, 5-vinyl H), 7.36–8.23 (m, 8H, ArH), 10.82 (s, 1H, NH).

[Compound 128]

2-(4-cyanophenylimino)-3-methyl-4-[N-(4-chlorophenyl) carbamoylmethyl]-1,3-thiazol-4-ine hydrochloride (R1=4-Cl, R$_2$=4-CN, R$_3$=CH$_3$, HX=HCl).

Starting materials: methylisothiocyanate, 4-cyanoaniline, 4-chloro-3-oxo-N-(4-chlorophenyl)butane amide Yield: 75% Melting point: 222–225° C. $^1$H NMR (DMSO-d$_6$) δ 3.71 (s, 3H, 3-CH$_3$), 4.01 (s, 2H, 4-CH$_2$), 6.95 (s, 1H, 5-vinyl H), 7.36–7.92 (m, 8H, ArH), 10.86 (s, 1H, NH).

[Compound 129]

2-(3-fluorophenylimino)-3-methyl-4-[N-(4-chlorophenyl) carbamoylmethyl]-1,3-thiazol-4-ine hydrochloride (R1=4-Cl, R$_2$=3-F, R$_3$=CH$_3$, HX=HCl).

Starting materials: methylisothiocyanate, 3-fluoroaniline, 4-chloro-3-oxo-N-(4-chlorophenyl)butane amide Yield: 47% Melting point: 234–236° C. $^1$H NMR (DMSO-d$_6$) δ 3.76 (s, 3H, 3-CH$_3$), 4.05 (s, 2H, 4-CH$_2$), 7.04 (s, 1H, 5-vinyl H), 7.17–7.69 (m, 8H, ArH), 10.94 (s, 1H, NH).

[Compound 130]

2-(4-bromophenylimino)-3-methyl-4-[N-(4-chlorophenyl) carbamoylmethyl]-1,3-thiazol-4-ine hydrochloride (R1=4-Cl, R$_2$=4-Br, R$_3$=CH$_3$, HX=HCl).

Starting materials: methylisothiocyanate, 4-bromoaniline, 4-chloro-3-oxo-N-(4-chlorophenyl)butane amide Yield: 71% Melting point: 228–235° C. $^1$H NMR (DMSO-d$_6$) δ 3.75 (s, 3H, 3-CH$_3$), 4.05 (s, 2H, 4-CH$_2$), 7.04 (s, 1H, 5-vinyl H), 7.37–7.74 (m, 8H, ArH), 10.34 (s, 1H, NH).

[Compound 131]

2-(2-phenylphenylimino)-3-methyl-4-[N-(4-chlorophenyl) carbamoylmethyl]-1,3-thiazol-4-ine hydrochloride (R1=4-Cl, R$_2$=2-C$_6$H$_5$, R$_3$=CH$_3$, HX=HCl).

Starting materials: methylisothiocyanate, 2-phenylaniline, 4-chloro-3-oxo-N-(4-chlorophenyl)butane amide Yield: 64% Melting point: 238–241° C. $^1$H NMR (DMSO-d$_6$) δ 3.76 (s, 3H, 3-CH$_3$), 4.05 (s, 2H, 4-CH$_2$), 7.03 (s, 1H, 5-vinyl H), 7.07–7.69 (m, 13H, ArH), 10.47 (s, 1H, NH).

[Compound 132]

2-(4-trifluoromethylphenylimino)-3-methyl-4-[N-(4-bromophenyl)carbamoylmethyl]-1,3-thiazol-4-ine hydrochloride (R1=4-Br, R$_2$=4-CF$_3$, R$_3$=CH$_3$, HX=HCl).

Starting materials: methylisothiocyanate, 4-trifluoromethylaniline, 4-chloro-3-oxo-N-(4-bromophenyl)butane amide Yield: 37% Melting point: 220–223° C. $^1$H NMR (DMSO-d$_6$) δ 3.78 (s, 3H, 3-CH$_3$), 4.07 (s. 2H, 4-CH$_2$), 7.05 (s, 1H, 5-vinyl H), 7.49~7.88 (m, 8H, ArH), 10.98 (s, 1H, NH); IR(KBr) 3426 (NH), 1660 (C=O), 1600 (C=C) cm$^{-1}$.

[Compound 133]

2-(2,4-difluorophenylimino)-3-methyl-4-[N-(4-bromophenyl)carbamoylmethyl]-1,3-thiazol-4-ine hydrochloride (R1=4-Br, R$_2$=2-F, 4-F, R$_3$=CH$_3$, HX=HCl).

Starting materials: methylisothiocyanate, 2,4-difluoroaniline, 4-chloro-3-oxo-N-(4-bromophenyl)butane amide Yield: 40% Melting point: 207–209° C. $^1$H NMR (DMSO-d$_6$) δ 3.72 (s, 3H, 3-CH$_3$), 4.03 (s, 2H, 4-CH$_2$), 6.95(s, 1H, 5-vinyl H), 7.22~7.64 (m, 7H, ArH), 10.9 (s, 1H, NH); IR(KBr.) 3434 (NH), 1665 (C=O), 1583 (C=C) cm$^{-1}$.

[Compound 134]

2-(3-chloro-2-fluorophenylimino)-3-methyl-4-[N-(4-bromophenyl)carbamoylmethyl]-1,3-thiazol-4-ine hydrochloride (R1=4-Br, R$_2$=3-Cl, 2-F, R$_3$=CH$_3$, HX=HCl).

Starting materials: methylisothiocyanate, 3-chloro-2-fluoroaniline, 4-chloro-3-oxo-N-(4-bromophenyl)butane amide Yield: 34% Melting point: 217–227° C. $^1$H NMR (DMSO-d$_6$) δ 3.75 (s, 3H, 3-CH$_3$), 4.05 (s, 2H, 4-CH$_2$), 7.02 (s, 1H, 5-vinyl H), 7.50~7.80 (m, 7H, ArH), 10.97 (s, 1H, NH); IR(KBr) 3448 (NH), 1658 (C=O), 1601 (C=C) cm$^{-1}$.

[Compound 135]

2-(2,4-dimethylphenylimino)-3-methyl-4-[N-(4-bromophenyl)carbamoylmethyl]-1,3-thiazol-4-ine hydrochloride (R1=4-Br, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(4-bromophenyl)butane amide Yield: 70% Melting point: 205–207° C. $^1$H NMR (DMSO-d$_6$) δ 2.24 and 2.33 (2s, 6H, 2×ArCH$_3$), 3.80 (s, 3H, 3-CH$_3$), 4.06 (s, 2H, 4-CH$_2$), 6.99 (s, 1H, 5-vinyl H), 7.16~7.67 (m, 7H, ArH), 11.10 (s, 1H, NH); IR(KBr) 3448 (NH), 1680 (C=O), 1590 (C=C) cm$^{-1}$.

[Compound 136]

2-(4-fluorophenylimino)-3-methyl-4-[N-(4-bromophenyl) carbamoylmethyl]-1,3-thiazol-4-ine hydrochloride (R1=4-Br, R$_2$=4-F, R$_3$=CH$_3$, HX=HCl).

Starting materials: methylisothiocyanate, 4-fluoroaniline, 4-chloro-3-oxo-N-(4-bromophenyl)butane amide Yield: 55% Melting point: 230–237° C. $^1$H NMR (DMSO-d$_6$) δ 3.77 (s, 3, 3-CH$_3$), 4.06 (s, 2H, 4-CH$_2$), 7.09 (s, 1H, 5-vinyl H), 7.36~7.66 (m, 8H, ArH), 11.02 (s, 1H, NH); IR(KBr) 3424 (NH), 1661 (C=O), 1584 (C=C) cm$^{-1}$.

[Compound 137]

2-(3-bromophenylimino)-3-methyl-4-[N-(4-bromophenyl) carbamoylmethyl]-1,3-thiazol-4-ine hydrochloride (R1=4-Br, R$_2$=3-Br, R$_3$=CH$_3$, HX=HCl).

Starting materials: methylisothiocyanate, 3-bromoaniline, 4-chloro-3-oxo-N-(4-bromophenyl)butane amide Yield: 34% Melting point: 218–229° C. $^1$H NMR (DMSO-$d_6$) δ 3.73 (s, 3H, 3-$CH_3$), 4.04 (s, 2H, 4-$CH_2$), 6.99 (s, 1H, 5-vinyl H), 7.47~7.72 (m, 8H, ArH), 10.90 (s, 1H, NH); IR(KBr) 3426 (NH), 1660 (C=O), 1599 (C=C) $cm^{-1}$.

[Compound 138]

2-(3,5-dichlorophenylimino)-3-methyl-4-[N-(4-bromophenyl)carbamoylmethyl]-1,3-thiazol-4-ine hydrochloride (R1=4-Br, $R_2$=3-C, 5-Cl, $R_3$=$CH_3$, HX=HCl).

Starting materials: methylisothiocyanate, 3,5-dichloroaniline, 4-chloro-3-oxo-N-(4-bromophenyl)butane amide Yield: 42% Melting point: 227° C. $^1$H NMR (DMSO-$d_6$) δ 3.68 (s, 3H, 3-$CH_3$), 4.01 (s, 2H, 4-$CH_2$), 6.80 (s, 1H, 5-vinyl H), 7.5~7.7 (m, 7H, ArH), 10.9 (s, 1H, NH); IR(KBr) 3424 (NH), 1660 (C=O), 1598 (C=C) $cm^{-1}$.

[Compound 139]

2-(4-trifluoromethoxyphenylimino)-3-methyl-4-[N-(4-bromophenyl)carbamoylmethyl]-1,3-thiazol-4-ine hydrochloride (R1=4-Br, $R_2$=2-$OCF_3$, $R_3$=$CH_3$, HX=HCl).

Starting materials: methylisothiocyanate, 4-trifluoromethoxyaniline, 4-chloro-3-oxo-N-(4-bromophenyl)butane amide Yield: 43% Melting point: 235° C. $^1$H NMR (DMSO-$d_6$) δ 3.78 (s, 3H, 3-$CH_3$), 4.01(s, 2H, 4-$CH_2$), 7.10 (s, 1H, 5-vinyl H), 7.50~7.70 (m, 8H, ArH), 10.99 (s, 1H, NH); IR(KBr) 3449 (NH), 1658 (C=O), 1585 (C=C) $cm^{-1}$.

[Compound 140]

2-(2-chloro-4-fluorophenylimino)-3-methyl-4-[N-(4-bromophenyl)carbamoylmethyl]-1,3-thiazol-4-ine hydrochloride (R1=4-Br, $R_2$=2-Cl, 4-F, $R_3$=$CH_3$, HX=HCl).

Starting materials: methylisothiocyanate, 2-chloro-4-fluoroaniline, 4-chloro-3-oxo-N-(4-bromophenyl)butane amide Yield: 57% Melting point: 218° C. $^1$H NMR (DMSO-$d_6$) δ 3.67 (s, 3H, 3-$CH_3$), 4.00 (s, 2H, 4-$CH_2$), 6.86 (s, 1H, 5-vinyl H), 7.40~7.7 (m, 7H, ArH), 10.93 (s, 1H, NH); IR(KBr) 3426 (NH), 1678 (C=O), 1568 (C=C) $cm^{-1}$.

[Compound 141]

2-(4-phenoxyphenylimino)-3-methyl-4-[N-(4-bromophenyl)carbamoylmethyl]-1,3-thiazol-4-ine hydrochloride (R1=4-Br, $R_2$=4-$OC_6H_5$, $R_3$=$CH_3$, HX=HCl).

Starting materials: methylisothiocyanate, 4-phenoxyaniline, 4-chloro-3-oxo-N-(4-bromophenyl)butane amide Yield: 76% Melting point: 232–235° C. $^1$H NMR (DMSO-$d_6$) δ 3.40 (s, 3H, 3-$CH_3$), 3.76 (s, 2H, 4-$CH_2$), 7.10~7.65 (m, 13H, ArH), 10.90 (s, 1H, NH); IR(KBr) 3424 (NH), 1668 (C=O), 1590 (C=C) $cm^{-1}$.

[Compound 142]

2-(4-bromo-2-methylphenylimino)-3-methyl-4-[N-(4-bromophenyl)carbamoylmethyl]-1,3-thiazol-4-ine hydrochloride (R1=4-Br, $R_2$=4-Br, 2-$CH_3$, $R_3$=$CH_3$, HX=HCl).

Starting materials: methylisothiocyanate, 4-bromo-2-methylaniline, 4-chloro-3-oxo-N-(4-bromophenyl)butane amide Yield: 79% Melting point: 219–221° C. $^1$H NMR (DMSO-$d_6$) δ 2.60 (s, 3H, Ar$CH_3$), 3.75 (s, 3H, 3-$CH_3$), 4.02 (s, 2H, 4-$CH_2$), 6.95 (s, 1H, 5-vinyl H), 7.39~7.68 (m, 7H, ArH), 10.92 (s, 1H, NH); IR(KBr) 3445 (NH), 1680 (C=O), 1574 (C=C) $cm^{-1}$.

[Compound 143]

2-(4-bromophenylimino)-3-methyl-4-[N-(4-bromophenyl)carbamoylmethyl]-1,3-thiazol-4-ine hydrochloride (R1=4-Br, $R_2$=4-Br, $R_3$=$CH_3$, HX=HCl).

Starting materials: methylisothiocyanate, 4-bromoaniline, 4-chloro-3-oxo-N-(4-bromophenyl)butane amide Yield: 41% Melting point: 239° C. $^1$H NMR (DMSO-$d_6$) δ 3.80 (s, 3H, 3-$CH_3$), 4.10 (s, 2H, 4-$CH_2$), 7.08 (s, 1H, 5-vinyl H), 7.50~7.80 (m, 8H, ArH), 11.1(s, 1H, NH); IR(KBr) 3424 (NH), 1662 (C=O),1598 (C=C) $cm^{-1}$.

[Compound 144]

2-(4-nitrophenylimino)-3-methyl-4-[N-(4-bromophenyl)carbamoylmethyl]-1,3-thiazol-4-ine hydrochloride (R1=4-Br, $R_2$=4-$NO_2$, $R_3$=$CH_3$, HX=HCl).

Starting materials: methylisothiocyanate, 4-nitroaniline, 4-chloro-3-oxo-N-(4-bromophenyl)butane amide Yield: 28% Melting point: 214–223° C. $^1$H NMR (DMSO-$d_6$) δ 3.70 (s, 3H, 3-$CH_3$), 3.98 (s, 2H, 4-$CH_2$), 6.89 (s, 1H, 5-vinyl H), 7.49~8.30 (m, 8H, ArH), 10.78 (s, 1H, NH); IR(KBr) 3422 (NH), 1685 (C=O), 1580 (C=C) $cm^{-1}$.

[Compound 145]

2-(2-methoxy-5-methylphenylimino)-3-methyl-4-[N-(4-bromophenyl)carbamoylmethyl]-1,3-thiazol-4-ine hydrochloride (R1=4-Br, $R_2$=2-$OCH_3$, 5-$CH_3$, $R_3$=$CH_3$, HX=HCl).

Starting materials: methylisothiocyanate, 2-methoxy-5-methylaniline, 4-chloro-3-oxo-N-(4-bromophenyl)butane amide Yield: 57% Melting point: 205–208° C. $^1$H NMR (DMSO-$d_6$) δ 2.28 (s, 3H, Ar$CH_3$), 3.76 (s, 3H, 3-$CH_3$), 3.80 (s, 3H, $OCH_3$), 4.07 (s, 2H, 4-$CH_2$), 7.02 (s, 1H, 5-vinyl H), 7.16~7.66 (m, 7H, ArH), 11.07 (s, 1H, NH); IR(KBr) 3424 (NH), 1684 (C=O), 1594 (C=C) $cm^{-1}$.

[Compound 146]

2-(3-fluorophenylimino)-3-methyl-4-[N-(4-bromophenyl)carbamoylmethyl]-1,3-thiazol-4-ine hydrochloride (R1=4-Br, $R_2$=3-F, $R_3$=$CH_3$, HX=HCl).

Starting materials: methylisothiocyanate, 3-fluoroaniline, 4-chloro-3-oxo-N-(4-bromophenyl)butane amide Yield: 49% Melting point: 234–235° C. $^1$H NMR (DMSO-$d_6$) δ 3.80 (s, 3H, 3-$CH_3$), 4.06 (s, 2H, 4-$CH_2$), 7.05 (s, 1H, 5-vinyl H), 7.20~7.60 (m, 8H, ArH), 10.98 (s, 1H, NH); IR(KBr) 3426 (NH), 1662 (C=O), 1586 (C=C) $cm^{-1}$.

[Compound 147]

2-[4-(n-butyl)phenylimino]-3-methyl-4-[N-(4-bromophenyl)carbamoylmethyl]-1,3-thiazol-4-ine hydrochloride (R1=4-Br, $R_2$=4-$(CH_2)_3CH_3$, $R_3$=$CH_3$, HX=HCl).

Starting materials: methylisothiocyanate, 4-(n-butyl)aniline, 4-chloro-3-oxo-N-(4-bromophenyl)butane amide Yield: 46% Melting point: 238–240° C. $^1$H NMR (DMSO-$d_6$) δ 0.90 (t, 3H, butyl $CH_3$), 1.27~1.35 (m, 2H, $CH_2$), 1.55~1.60 (m, 2H, $CH_2$), 2.50~2.65 (m, 2H, $CH_2$), 3.80 (s, 3H, 3-$CH_3$), 4.10 (s, 2H, 4-$CH_2$), 7.05 (s, 1H, 5-vinyl H), 7.33~7.66 (m, 8H, ArH), 11.07 (s, 1H, NH); IR(KBr) 3424 (NH), 1666 (C=O), 1594 (C=C) $cm^{-1}$.

[Compound 148]

2-(2-fluorophenylimino)-3-methyl-4-[N-(4-bromophenyl)carbamoylmethyl]-1,3-thiazol-4-ine hydrochloride (R1=4-Br, $R_2$=2-F, $R_3$=$CH_3$, HX=HCl).

Starting materials: methylisothiocyanate, 2-fluoroaniline, 4-chloro-3-oxo-N-(4-bromophenyl)butane amide Yield: 49% Melting point: 188–192° C. $^1$H NMR (DMSO-$d_6$) δ 3.77 (s, 3H, 3-$CH_3$), 4.06 (s, 2H, 4-$CH_2$), 7.00 (s, 1H, 5-vinyl H), 7.34~7.66 (m, 8H, ArH) 11.03 (s, 1H, NH); IR(KBr) 3426 (NH), 1667 (C=O), 1578 (C=C) $cm^{-1}$.

[Compound 149]

2-(3-chloro-4-fluorophenylimino)-3-methyl-4-[N-(2-fluorophenyl)carbamoylmethyl]-1,3-thiazol-4-ine hydrochloride (R1=2-F, $R_2$=3-Cl, 4-F, $R_3$=$CH_3$, HX=HCl).

Starting materials: methylisothiocyanate, 3-chloro-4-fluoroaniline, 4-chloro-3-oxo-N-(2-fluorophenyl)butane amide Yield: 44% Melting point: 195~201° C. $^1$H NMR (DMSO-d$_6$) δ 3.75 (s, 3H, 3-CH$_3$), 4.09 (s, 2H, 4-CH$_2$) 7.00 (s, 1H, 5-vinyl H), 7.11~7.81 (m, 7H, ArH), 10.32 (s, 1H, NH); IR(KBr) 3426 (NH), 1680 (C=O), 1580 (C=C) cm$^{-1}$.

[Compound 150]
2-(4-chloro-2-fluorophenylimino)-3-methyl-4-[N-(2-fluorophenyl)carbamoylmethyl]-1,3-thiazol-4-ine hydrochloride (R1=2-F, R$_2$=4-Cl, 2-F, R$_3$=CH$_3$, HX=HCl).

Starting materials: methylisothiocyanate, 4-chloro-2-fluoroaniline, 4-chloro-3-oxo-N-(2-fluorophenyl)butane amide Yield: 30% Melting point: 183~186° C. $^1$H NMR (DMSO-d$_6$) δ3.70 (s, 3H, 3-CH$_3$), 4.01 (s, 2H, 4-CH$_2$), 6.77 (s, 1H, 5-vinyl H), 7.16~7.85 (m, 7H, ArH), 10.26 (s, 1H, NH); IR(KBr) 3424 (NH), 1686 (C=O), 1574 (C=C) cm$^{-1}$.

[Compound 151]
2-(4-chloro-2-fluoro-5-isopropoxyphenylimino)-3-methyl-4-[N-(2-fluorophenyl)carbamoylmethyl]-1,3-thiazol-4-ine hydrochloride (R1=2-F, R$_2$=4-Cl, 2-F, 5-OCH(CH$_3$)$_2$, R$_3$=CH$_3$, HX=HCl).

Starting materials: methylisothiocyanate, 4-chloro-2-fluoro-5-isopropoxyaniline, 4-chloro-3-oxo-N-(2-fluorophenyl)butane amide Yield: 46% Melting point: 177~179° C. $^1$H NMR (DMSO-d$_6$) δ 1.25 (d, 6H, isopropoxy (CH$_3$)$_2$), 3.61 (s, 3H, 3-CH$_3$), 4.00 (s. 2H, 4-CH$_2$), 4.70~4.57 (m, 1H, isopropoxy CH), 6.75 (s, 1H, 5-vinyl H), 7.85~7.16 (m, 6H, ArH), 10.24 (s, 1H, NH); IR(KBr) 3446 (NH); 1694 (C=O), 1568 (C=C) cm$^{-1}$.

[Compound 152]
2-(4-bromophenylimino)-3-methyl-4-[N-(2-fluorophenyl)carbamoylmethyl]-1,3-thiazol-4-ine hydrochloride (R1=2-F, R$_2$=4-Br, R$_3$=CH$_3$, HX=HCl).

Starting materials: methylisothiocyanate, 4-bromoaniline, 4-chloro-3-oxo-N-(2-fluorophenyl)butane amide Yield: 31% Melting point: 229~230° C. $^1$H NMR (DMSO-d$_6$) δ 3.76 (s, 3H, 3-CH$_3$), 4.09 (s, 2H, 4-CH$_2$), 7.02 (s, 1H, 5-vinyl H), 7.17~7.80 (m, 8H, ArH), 10.31 (s, 1H, NH); IR(KBr) 3426(NH), 1684(C=O), 1596(C=C) cm$^{-1}$.

[Compound 153]
2-(3-bromophenylimino)-3-methyl-4-[N-(2-fluorophenyl)carbamoylmethyl]-1,3-thiazol-4-ine hydrochloride (R1=2-F, R$_2$=3-Br, R$_3$=CH$_3$, HX=HCl).

Starting materials: methylisothiocyanate, 3-bromoaniline, 4-chloro-3-oxo-N-(2-fluorophenyl)butane amide Yield: 41% Melting point: 169~174° C. $^1$H NMR (DMSO-d$_6$) δ 3.74 (s, 3H, 3-CH$_3$), 4.01 (s, 2H, 4-CH$_2$), 6.89 (s, 1H, 5-vinyl H), 7.85~7.17 (m, 8H, ArH), 10.29 (s, 1H, NH); IR(KBr) 3515 (NH), 1680 (C=O), 1600 (C=C) cm$^{-1}$.

[Compound 154]
2-(2,4-dimethylphenylimino)-3-methyl-4-(N-(4-chlorophenyl)carbamoylmethyl)-1,3-thiazol-4-ine hydrochloride (R1=4-Cl, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(4-chlorophenyl)butane amide Yield: 86% Melting point: 219~221° C. $^1$H NMR (DMSO-d$_6$) δ 2.23 and 2.33 (2s, 6H, ArCH$_3$), 3.76 (s, 3H, 3-CH$_3$), 4.05 (s, 2H, 4-CH$_2$), 6.99 (s, 1H, 5-vinyl H), 7.17~7.73 (m, 7H, ArH), 11.05 (s, 1H, NH); IR(KBr) 3455 (NH), 1682 (C=C), 1582 (C=C) cm$^{-1}$.

[Compound 155]
2-(3-chloro-4-fluorophenylimino)-3-methyl-4-[N-(4-chlorophenyl)carbamoylmethyl]-1,3-thiazol-4-ine hydrochloride (R1=4-Cl, R$_2$=3-Cl, 4-F, R$_3$=CH$_3$, HX=HCl).

Starting materials: methylisothiocyanate, 3-chloro-4-fluoroaniline, 4-chloro-3-oxo-N-(4-chlorophenyl)butane amide Yield: 67% Melting point: 211~213° C. $^1$H NMR (DMSO-d$_6$) δ 3.72 (s, 3H, 3-CH$_3$), 4.09 (s, 2H, 4-CH$_2$), 6.97 (s, 1H, 5-vinyl H), 7.77~7.97 (m, 7H, ArH), 10.89 (s, 1H, NH); IR(KBr) 3445 (NH), 1666 (C=O), 1600 (C=C) cm$^{-1}$.

[Compound 156]
2-(3-bromophenylimino)-3-methyl-4-[N-(4-chlorophenyl)carbamoylmethyl]-1,3-thiazol-4-ine hydrochloride (R1=4-Cl, R$_2$=3-Br, R$_3$=CH$_3$, HX=HCl).

Starting materials: methylisothiocyanate, 3-bromoaniline, 4-chloro-3-oxo-N-(4-chlorophenyl)butane amide Yield: 49% Melting point: 226~229° C. $^1$H NMR (DMSO-d$_6$) δ 3.75 (s, 3H, 3-CH$_3$), 4.05 (s, 2H, 4-CH$_2$), 7.01 (s, 1H, 5-vinyl H), 7.79~7.91 (m, 8H, ArH), 10.92 (s, 1H, NH); IR(KBr) 3435 (NH), 1676 (C=C), 1600 (C=C) cm$^{-1}$.

[Compound 157]
2-(2-methoxy-5-methylphenylimino)-3-methyl-4-[N-(4-chlorophenyl)carbamoylmethyl]-1,3-thiazol-4-ine hydrochloride (R1=4-Cl, R$_2$=2-OCH$_3$, 5-CH$_3$, R$_3$=CH$_3$, HX=HCl).

Starting materials: methylisothiocyanate, 2-methoxy-5-methylaniline, 4-chloro-3-oxo-N-(4-chlorophenyl)butane amide Yield: 59% Melting point: 205~208° C. $^1$H NMR (DMSO-d$_6$) δ 2.98 (s, 3H, ArCH$_3$), 3.87 (s, 3H, 3-CH$_3$), 3.90 (s, 3H, OCH$_3$), 4.17 (s, 2H, 4-CH$_2$), 7.13 (s, 1H, 5-vinyl H), 7.25~7.82 (m, 7H, ArH), 11.19 (s, 1H, NH); IR(KBr) 3415 (NH), 1686 (C=O), 1596 (C=C) cm$^{-1}$.

[Compound 158]
2-(4-chloro-2-fluorophenylimino)-3-methyl-4-[N-(4-chlorophenyl)carbamoylmethyl]-1,3-thiazol-4-ine hydrochloride (R1=4-Cl, R$_2$=4-Cl, 2-F, R$_3$=CH$_3$, HX=HCl).

Starting materials: methylisothiocyanate, 4-chloro-2-fluoroaniline, 4-chloro-3-oxo-N-(4-chlorophenyl)butane amide Yield: 30% Melting point: 211~214° C. $^1$H NMR (DMSO-d$_6$) δ 3.64 (s, 3H, 3-CH$_3$), 3.98 (s, 2H, 4-CH$_2$), 6.81 (s, 1H, 5-vinyl H), 7.69~7.96-(m, 7H, ArH), 10.88 (s, 1H, NH); IR(KBr) 3435 (NH), 1676 (C=O), 1578 (C=C) cm$^{-1}$.

[Compound 159]
2-(2,4-difluorophenylimino)-3-methyl-4-[N-(4-chlorophenyl)carbamoylmethyl]-1,3thiazol-4-ine hydrochloride (R1=4-Cl, R$_2$=2-F, 4-F, R$_3$-CH$_3$, HX=HCl).

Starting materials: methylisothiocyanate, 2,4-difluoroaniline, 4-chloro-3-oxo-N-(4-chlorophenyl)butane amide Yield: 36% Melting point; 205~207° C. $^1$H NMR (DMSO-d$_6$) δ 3.72 (s, 3H, 3-CH$_3$), 4.02 (s, 2H, 4-CH$_2$), 6.92 (s, 1H, 5-vinyl H), 7.30~7.69 (m, 7H, ArH), 10.92 (s, 1H, NH); IR(KBr) 3428 (NH), 1668 (C=O), 1582 (C=C) cm$^{-1}$.

[Compound 160]
2-(2-fluorophenylimino)-3-methyl-4-[N-(4-chlorophenyl)carbamoylmethyl]-1,3-thiazol-4-ine hydrochloride (R1=4-Cl, R$_2$=2-F, R$_3$=CH$_3$, HX=HCl).

Starting materials: methylisothiocyanate, 2-fluoroaniline, 4-chloro-3-oxo-N-(4-chlorophenyl)butane amide Yield: 66% Melting point: 199~204° C. $^1$H NMR (DMSO-d$_6$) δ 3.72 (s, 3H, 3-CH$_3$), 4.02 (s, 2H,-4-CH$_2$), 6.92 (s, 1H, 5-vinyl H), 7.93~7.69 (m, 8H, ArH), 10.89 (s, 1H, NH); IR(KBr) 3427 (NH), 1684 (C=O), 1572 (C=C) cm$^{-1}$.

[Compound 161]
2-(4-chloro-5-isopropoxy-2-fluorophenylimino)-3-methyl-4-[N-(4-chlorophenyl)carbamoylmethyl]-1,3-thiazol-4-ine hydrochloride (R1=4-Cl, R$_2$=4-Cl, 2-F, 5-OCH(CH$_3$)$_2$, R$_3$=CH$_3$, HX=HCl).

Starting materials: methylisothiocyanate, 4-chloro-5-isopropoxy-2-fluoroaniline, 4-chloro-3-oxo-N-(4-chlorophenyl)butane amide Yield: 40% Melting point: 198~204° C. $^1$H NMR (DMSO-$d_6$) δ 1.25 (d, 6H, isopropoxy (CH$_3$)$_2$), 3.66 (s, 3H, 3-CH$_3$), 3.99 (s, 2H, 4-CH$_2$), 4.60~4.65 (m, 1H, isopropoxy CH), 6.81 (s, 1H, 5-vinyl H), 6.83~7.70 (m, 6H, ArH), 10.89 (s, 1H, NH); IR(KBr) 3447 (NH), 1674 (C=O), 1576 (C=C) cm$^{-1}$.

[Compound 162]
2-(4-bromophenylimino)-3-methyl-4-[N-(4-methylphenyl) carbamoylmethyl]-1,3-thiazol-4-ine hydrochloride (R1=4-CH$_3$, R$_2$=4-Br, R$_3$=CH$_3$, HX=HCl).

Starting materials: methylisothiocyanate, 4-bromoaniline, 4-chloro-3-oxo-N-(4-methylphenyl)butane amide Yield: 37% Melting point: 241~248° C. $^1$H NMR (DMSO-$d_6$) δ 2.25 (s, 3H, ArCH$_3$), 3.75 (s, 3H, 3-CH$_3$), 4.00 (s, 2H, 4-CH$_2$), 7.00 (s, 1H, 5-vinyl H), 7.11~7.73 (m, 8H, ArH), 10.58 (s, 1H, NH); IR(KBr) 3426 (NH), 1660 (C=O), 1600 (C=C) cm$^{-1}$.

[Compound 163]
2-(4-fluorophenylimino)-3-methyl-4-[N-(4-methylphenyl) carbamoylmethyl]-1,3-thiazol-4-ine hydrochloride (R1=4-CH$_3$, R$_2$=4-F, R$_3$=CH$_3$, HX=HCl).

Starting materials: methylisothiocyanate, 4-fluoroaniline, 4-chloro-3-oxo-N-(4-methylphenyl)butane amide Yield: 78% Melting point: 246~248° C. $^1$H NMR (DMSO-$d_6$) δ 2.25 (s, 3H, ArCH$_3$), 3.80 (s, 3H, 3-CH$_3$), 4.10 (s, 2H, 4-CH$_2$), 7.10 (s, 1H, 5-vinyl H), 7.11~7.60 (m, 8H, ArH), 10.71 (s, 1H, NH); IR(KBr) 3424 (NH), 1660 (C=O), 1586 (C=C) cm$^{-1}$.

[Compound 164]
2-(4-chlorophenylimino)-3-methyl-4-[N-(4-methylphenyl) carbamoylmethyl]-1,3-thiazol-4-ine hydrochloride (R1=4-CH$_3$, R$_2$=4-Cl, R$_3$=CH$_3$, HX=HCl).

Starting materials: methylisothiocyanate, 4-chloroaniline, 4-chloro-3-oxo-N-(4-methylphenyl)butane amide Yield: 65% Melting point: 248~252° C. $^1$H NMR (DMSO-$d_6$) δ 2.25 (s, 3H, ArCH$_3$), 3.77 (s, 3H, 3-CH$_3$), 4.02 (s, 2H, 4-CH$_2$), 7.02 (s, 1H, 5-vinyl H), 7.11~7.61 (m, 8H, ArH), 10.64 (s, 1H, NH); IR(KBr) 3447 (NH), 1660 (C=O), 1602 (C=C) cm$^{-1}$.

[Compound 165]
2-(2.4-dimethylphenylimino)-3-methyl-4-[N-(4-methylphenyl)carbamoylmethyl]-1,3-thiazol-4-ine hydrochloride (R1=4-CH$_3$, R$_2$=2-CH$_3$, 4-CH$_3$, R$_3$=CH$_3$, HX=HCl).

Starting materials: methylisothiocyanate, 2.4-dimethylaniline, 4-chloro-3-oxo-N-(4-methylphenyl)butane amide Yield: 76% Melting point: 214~216° C. $^1$H NMR (DMSO-$d_6$+CDCl$_3$-1:2) δ 2.23, 2.24 and 2.32 (3s, 9H, 3×ArCH$_3$), 3.90 (s, 3H, 3-CH$_3$), 4.00 (s, 2H, 4-CH$_2$), 6.95 (s, 1H, 5-vinyl H), 6.99~7.52 (m, 7H, ArH) 10.70 (s, 1H, NH); IR(KBr) 3424 (NH), 1680 (C=C), 1580 (C=C) cm$^{-1}$.

[Compound 166]
2-(2-methoxy-5-methylphenylimino)-3-methyl-4-[N-(4-methylphenyl)carbamoylmethyl]-1,3-thiazol-4-ine hydrochloride (R1=4-CH$_3$, R$_2$=2-OCH$_3$, 5-CH$_3$, R$_3$=CH$_3$, HX=HCl).

Starting materials: methylisothiocyanate, 2-methoxy-5-methylaniline, 4-chloro-3-oxo-N-(4-methylphenyl)butane amide Yield: 48% Melting point: 207~210° C. $^1$H NMR (DMSO-$d_6$+CDCl$_3$=1:2) δ 2.33 and 2.35 (2s, 6H, 2×ArCH$_3$), 3.87 (s, 3H, 3-CH$_3$), 3.97 (s, 3H, 2-OCH$_3$), 4.10 (s, 2H, 4-CH$_2$), 7.06 (s, 1H, 5-vinyl H), 7.07~7.63 (m, 7H, ArH), 11.49 (s, 1H, NH); IR(KBr) 3428 (NH), 1680 (C=O), 1598 (C=C) cm$^{-1}$.

[Compound 167]
2-(2-fluorophenylimino)-3-methyl-4-[N-(4-methylphenyl) carbamoylmethyl]-1,3-thiazol-4-ine hydrochloride (R1=4-CH$_3$, R$_2$=2-F, R$_3$=CH$_3$, HX=HCl).

Starting materials: methylisothiocyanate, 2-fluoroaniline, 4-chloro-3-oxo-N-(4-methylphenyl)butane amide Yield: 54% Melting point: 178~180° C. $^1$H NMR (DMSO-$d_6$) δ 2.24 (s, 3H, ArCH$_3$), 3.80 (s, 3H, 3-CH$_3$), 4.10 (s, 2H, 4-CH$_2$), 7.02 (s, 1H, 5-vinyl H), 7.10~7.61 (m, 8H, ArH), 10.76 (s, 1H, NH): IR(KBr) 3445 (NH), 1676 (C=O), 1572 (C=C) cm$^{-1}$.

[Compound 168]
2-(4-chloro-5-isopropoxy-2-fluorophenylimino)-3-methyl-4-[N-(4-methylphenyl)carbamoylmethyl-]-1,3-thiazol-4-ine hydrochloride (R1=4-CH$_3$, R$_2$=4-Cl, 2-F, 5-OCH(CH$_3$)$_2$, R$_3$=CH$_3$, HX=HCl).

Starting materials: methylisothiocyanate, 4-chloro-5-isopropoxy-2-fluoroaniline, 4-chloro-3-oxo-N-(4-methylphenyl)butane amide Yield: 39% Melting point: 195~198° C. $^1$H NMR (DMSO-$d_6$+CDCl$_3$=1:2) δ 1.37 (d, 6H, isopropoxy (CH$_3$)$_2$), 2.31 (s, 3H, ArCH$_3$), 4.01 (s, 3H, 3-CH$_3$), 4.07 (s, 2H, 4-CH$_2$), 4.52~4.56 (m, 1H, isopropoxy CH), 7.08 (s, 1H, 5-vinyl H), 7.10~7.85 (m, 6H, ArH), 10.64 (s, 1H, NH); IR(KBr) 3404 (NH), 1676 (C=O), 1586 (C=C) cm$^{-1}$.

[Compound 169]
2-(4-cyanophenylimino)-3-methyl-4-[N-(4-nitrophenyl) carbamoylmethyl]-1,3-thiazol-4-ine hydrochloride (R1=4-NO$_2$, R$_2$=4-CN, R$_3$=CH$_3$, HX=HCl).

Starting materials: methylisothiocyanate, 4-cyanoaniline, 4-chloro-3-oxo-N-(4-nitrophenyl)butane amide Yield: 37% Melting point: 250~252° C. $^1$H NMR (DMSO-$d_6$) δ 3.69 (s, 3H, 3-CH$_3$), 4.11 (s, 2H, 4-CH$_2$), 6.94 (s, 1H, 5-vinyl H), 7.54~8.26 (s, 8H, ArH), 11.99 (s, 1H, NH);. IR(KBr) 3424 (NH), 1686 (C=O), 1598 (C=C) cm$^{-1}$.

[Compound 170]
2-(2.4-difluorophenylimino)-3-methyl-4-[N-(4-nitrophenyl) carbamoylmethyl]-1,3-thiazol-4-ine hydrochloride (R1=4-NO$_2$, R$_2$=2-F, 4-F, R$_3$=CH$_3$, HX=HCl).

Starting materials: methylisothiocyanate, 2.4-difluoroaniline, 4-chloro-3oxo-N-(4-nitrophenyl)butane amide Yield: 56% Melting point: 245~247° C. $^1$H NMR (DMSO-$d_6$) δ 3.78 (s, 3H, 3-CH$_3$), 4.17 (s, 2H, 4-CH$_2$), 7.10 (s, 1H, 5-vinyl H), 7.45~8.26 (m, 7H, ArH), 11.61 (s, 1H, NH); IR(KBr) 3448 (NH), 1706 (C=O), 1598 (C=C) cm$^{-1}$.

[Compound 171]
2-(4-bromophenylimino)-3-methyl-4-[N-(4-nitrophenyl) carbamoylmethyl]-4-thiazoline hydrochloride (R1=4-NO$_2$, R$_2$=4-Br, R$_3$=CH$_3$, HX=HCl).

Starting materials: methylisothiocyanate, 4-bromoaniline, 4-chloro-3-oxo-N-(4-nitrophenyl)butane amide Yield: 48% Melting point: 240–241° C. $^1$H NMR (DMSO-$d_6$) δ 3.78 (s, 3H, 3-CH$_3$), 4.17 (s, 2H, 4-CH$_2$), 7.10 (s, 1H, 5-vinyl H), 7.45~8.26 (m, 8H, ArH), 11.61 (s, 1H, NH); IR(KBr) 3448 (NH), 1706 (C=O), 1598 (C=C) cm$^{-1}$.

[Compound 172]
2-(4-trifluoromethylphenylimino)-3-methyl-4-[N-(4-nitrophenyl)carbamoylmethyl]-4-thiazoline hydrochloride (R1=4-NO$_2$, R$_2$=4-CF$_3$, R$_3$=CH$_3$, HX=HCl).

Starting materials: methylisothiocyanate, 4-trifluoromethylaniline, 4-chloro-3-oxo-N-(4-nitrophenyl) butane amide Yield: 58% Melting point: 252~254° C. $^1$H NMR (DMSO-$d_6$) δ 3.79 (s, 3H, 3-CH$_3$), 4.15 (s, 2H, 4-CH$_2$), 7.08 (s, 1H, 5-vinyl H), 7.69~8.29 (m, 8H, ArH), 11.53 (s, 1H, NH); IR(KBr) 3430 (NH), 1702 (C=O), 1602 (C=C) cm$^{-1}$.

[Compound 173]
2-(3,5-dichlorophenylimino)-3-methyl-4-[N-(4-nitrophenyl)carbamoylmethyl]-4-thiazoline hydrochloride (R1=4-$NO_2$, $R_2$=3-Cl, 5-Cl $R_3$=$CH_3$, HX=HCl).

Starting materials: methylisothiocyanate, 3,5-dichloroaniline 4-chloro-3-oxo-N-(4-nitrophenyl)butane amide Yield: 37% Melting point: 235~239° C. $^1$H NMR (DMSO-$d_6$) δ 3.69 (s, 3H, 3-$CH_3$), 4.12 (s, 2H, 4-$CH_2$), 6.96 (s, 1H, 5-vinyl H), 7.50~8.25 (m, 8H, ArH), 11.47 (s, 1H, NH); IR(KBr) 3426 (NH), 1692 (C=O), 1594 (C=C) $cm^{-1}$.

[Compound 174]
2-(4-phenoxyphenylimino)-3-methyl-4-[N-(4-nitrophenyl)carbamoylmethyl]-4-thiazoline hydrochloride (R1=4-$NO_2$, $R_2$=2-$OC_6H_5$, $R_3$=$CH_3$, HX=HCl).

Starting materials: methylisothiocyanate, 4-phenoxyaniline, 4-chloro-3-oxo-N-(4-nitrophenyl)butane amide Yield: 55% Melting point: 228~229° C. $^1$H NMR (DMSO-$d_6$+$CDCl_3$=1:2) δ 3.95 (s, 3H, 3-$CH_3$), 4.19 (s, 2H, 4-$CH_2$), 7.04 (s, 1H, 5-vinyl H), 7.06~8.16 (s, 13H, ArH), 11.62 (s, 1H, NH); IR(KBr) 3426 (NH), 1674 (C=O), 1592 (C=C) $cm^{-1}$.

[Compound 175]
2-(2,4-dimethylphenylimino)-3-methyl-4-[N-(4-nitrophenyl)carbamoylmethyl]-4-thiazoline hydrochloride (R1=4-$NO_2$, $R_2$=2-$CH_3$, 4-$CH_3$, $R_3$=$CH_3$, HX=HCl).

Starting materials: methylisothiocyanate, 2,4-dimethylaniline, 4-chloro-3-oxo-N-(4-nitrophenyl)butane amide Yield: 70% Melting point: 204~207° C. $^1$H NMR (DMSO-$d_6$+$CDCl_3$=1:2) δ 2.29 and 2.38 (2s, 6H, Ar$CH_3$), 3.97 (s 3H, 3-$CH_3$), 4.21 (s, 2H, 4-$CH_2$), 7.09 (s, 1H, 5-vinyl H), 7.10~8.18 (m, 7H, ArH) 11.60 (s, 1H, NH); IR(KBr) 3428 (NH), 1704 (C=C), 1594 (C=C) $cm^{-1}$.

[Compound 176]
2-(4-trifluoromethoxyphenylimino)-3-methyl-4-[N-(4-nitrophenyl)carbamoylmethyl]-4-thiazoline hydrochloride (R1=4-$NO_2$, $R_2$=4-$OCF_3$, $R_3$=$CH_3$, HX=HCl).

Starting materials: methylisothiocyanate, 4-trifluoromethoxyaniline, 4-chloro-3-oxo-N-(4-nitrophenyl)butane amide Yield: 49% Melting point: 229~230° C. $^1$H NMR (DMSO-$d_6$+$CDCl_3$=1:2) δ 3.94 (s, 3H, 3-$CH_3$), 4.16 (s, 2H, 4-$CH_2$) 7.15 (s, 1H, 5-vinyl H), 7.94~8.13 (m, 8H, ArH), 11.48 (s, 1H, NH); IR(KBr) 3428 (NH), 1702 (C=O), 1598 (C=C) $cm^{-1}$.

[Compound 177]
2-(4-fluorophenylimino)-3-methyl-4-[N-(4-nitrophenyl)carbamoylmethyl]-4-thiazoline hydrochloride (R1=4-$NO_2$, $R_2$=4-F, $R_3$=$CH_3$, HX=HCl).

Starting materials: methylisothiocyanate, 4-fluoroaniline, 4-chloro-3-oxo-N-(4-nitrophenyl)butane amide Yield: 61% Melting point: 257° C. $^1$H NMR (DMSO-$d_6$) δ 3.79 (s, 3H, 3-$CH_3$), 4.17 (s, 2H, 4-$CH_2$), 7.08 (s, 1H, 5-vinyl H), 7.37~8.26 (m, 8H, ArH), 11.62 (s, 1H, NH); IR(KBr) 3408 (NH), 1708 (C=O), 1598 (C=C) $cm^{-1}$.

[Compound 178]
2-(3-fluorophenylimino)-3-methyl-4-[N-(4-nitrophenyl)carbamoylmethyl]-4-thiazoline hydrochloride (R1=4-$NO_2$, $R_2$=3-F, $R_3$=$CH_3$, HX=HCl).

Starting materials: methylisothiocyanate, 3-fluoroaniline, 4-chloro-3-oxo-N-(4-nitrophenyl)butane amide Yield: 65% Melting point: 224~229° C. $^1$H NMR (DMSO-$d_6$+$CDCl_3$1:2) δ 3.96 (s, 3H, 3-CH3), 4.19 (s, 2H, 4-$CH_2$), 7.08 (s, 1H, 5-vinyl H), 7.10~8.15 (m, 8H, ArH), 11.57 (s, 1H, NH); IR(KBr) 3424 (NH), 1670 (C=O), 1588 (C=C) $cm^{-1}$.

[Compound 179]
2-(4-chlorophenylimino)-3-methyl-4-[N-(4-nitrophenyl)carbamoylmethyl]-4-thiazoline hydrochloride (R1=4-$NO_2$, $R_2$=4-Cl, $R_3$=$CH_3$, HX=HCl).

Starting materials: methylisothiocyanate, 4-chloroaniline, 4-chloro-3-oxo-N-(4-nitrophenyl)butane amide Yield: 73% Melting point: 247° C. $^1$H NMR (DMSO-$d_6$) δ 3.78 (s, 3H, 3-$CH_3$), 4.17 (s, 2H, 4-$CH_2$), 7.09 (s, 1H, 5-vinyl H), 7.53~8.26(m, 8H, ArH), 11.60 (s, 1H, NH); IR(KBr) 3428 (NH), 1708 (C=O), 1596 (C=C) $cm^{-1}$.

[Compound 180]
2-(3-chloro-4-fluorophenylimino)-3-methyl-4-[N-(4-nitrophenyl)carbamoylmethyl]-4-thiazoline hydrochloride (R1=4-$NO_2$, $R_2$=3-Cl, 4-F, $R_3$=$CH_3$, HX=HCl).

Starting materials: methylisothiocyanate, 3-chloro-4-fluoroaniline, 4-chloro-3-oxo-N-(4-nitrophenyl)butane amide Yield: 60% Melting point: 239° C. $^1$H NMR (DMSO-$d_6$) δ 3.75 (s, 3H, 3-$CH_3$), 4.15 (s, 2H, 4-$CH_2$), 7.04 (s, 1H, 5-vinyl H), 7.52~8.26 (m, 7H, ArH), 11.54 (s, 1H, NH); IR(KBr) 3426 (NH), 1696 (C=O), 1592 (C=C) $cm^{-1}$.

[Compound 181]
2-[4-(n-butyl)phenylimino]-3-methyl-4-[N-(4-nitrophenyl)carbamoylmethyl]-4-thiazoline hydrochloride (R1=4-$NO_2$, $R_2$=4-$(CH_2)_3CH_3$, $R_3$—$CH_3$, HX=HCl).

Starting materials: methylisothiocyanate, 4-(n-butyl)aniline, 4-chloro-3-oxo-N-(4-nitrophenyl)butane amide Yield: 60% Melting point: 242° C. $^1$H NMR (DMSO-$d_6$) δ 0.88~0.93 (t, 3H, $CH_3$), 1.27~1.35 (m, 2H, $CH_2$), 1.52~1.60 (m, 2H, $CH_2$), 2.50~2.65 (m, 2H, $CH_2$), 3.78 (s, 3H, 3-$CH_3$), 4.17 (s, 2H, 4-$CH_2$), 7.07 (s, 1H, 5-vinyl H), 7.34~8.26 (m, 8H, ArH), 11.62 (s, 1H, NH),; IR(KBr) 3424 (NH), 1674 (C=O), 1566 (C=C) $cm^{-1}$.

[Compound 182]
2-(2-methoxy-5-methylphenylimino)-3-methyl-4-[N-(4-nitrophenyl)carbamoylmethyl]-4-thiazoline hydrochloride (R1=4-$NO_2$, $R_2$=2-$OCH_3$, 5-$CH_3$, $R_3$=$CH_3$, HX=HCl).

Starting materials: methylisothiocyanate, 2-methoxy-5-methylaniline, 4-chloro-3-oxo-N-(4-nitrophenyl)butane amide Yield: 59% Melting point: 227~229° C. $^1$H NMR (DMSO-$d_6$) δ 2.28 (s, 3H, Ar$CH_3$), 3.78 (s, 3H, 3-$CH_3$), 3.81 (s, 3H, 2-$OCH_3$), 4.17 (s, 2H, 4-$CH_2$), 7.09 (s, 1H, 5-vinyl H), 7.16~8.26 (m, 7H, ArH), 11.69 (s, 1H, NH); IR(KBr) 3426 (NH), 1694 (C=O), 1600 (C=C) $cm^{-1}$.

[Compound 183]
2-(4-chloro-5-isopropoxy-2-fluorophenylimino)-3-methyl-4-[N-(4-nitrophenyl)carbamoylmethyl]-4-thiazoline hydrochloride (R1=4-$NO_2$, $R_2$=4-Cl, 2-F, 5-$OCH(CH_3)_{2_1}$ $R_3$=$CH_3$, HX=HCl).

Starting materials: methylisothiocyanate, 4-chloro-5-isopropoxy-2-fluoroaniline, 4-chloro-3-oxo-N-(4-nitrophenyl)butane amide Yield: 57% Melting point: 225~227° C. $^1$H NMR (DMSO-$d_6$) δ 1.29 (d, 6H, isopropoxy $(CH_3)_2$), 3.67 (s, 3H, 3-$CH_3$), 4.09 (s, 2H, 4-$CH_2$), 4.57~4.68 (m, 1H, CH), 6.88 (s, 1H, 5-vinyl H), 7.31~8.26 (m, 6H, ArH), 11.47 (s, 1H, NH); IR(KBr) 3426 (NH), 1696 (C=O), 1592 (C=C) $cm^{-1}$.

[Compound 184]
2-(2-fluorophenylimino)-3-methyl-4-[N-(4-nitrophenyl)carbamoylmethyl]-4-thiazoline hydrochloride (R1=4-$NO_2$, $R_2$=2-F, $R_3$=$CH_3$, HX=HCl).

Starting materials: methylisothiocyanate, 2-fluoroaniline, 4-chloro-3-oxo-N-(4-nitrophenyl)butane amide Yield: 63% Melting point: 238~239° C. $^1$H NMR (DMSO-$d_6$) δ 3.75 (s, 3H, 3-$CH_3$), 4.14 (s, 2H, 4-$CH_2$), 7.00 (s, 1H, 5-vinyl H), 7.32~8.26 (m, 8H, ArH), 11.53 (s, 1H, NH); IR(KBr) 3446 (NH), 1708 (C=O), 1596 (C=C) $cm^{-1}$.

[Compound 185]
2-(4-chloro-5-isopropoxy-2-fluorophenylimino)-3-methyl-4-[N-(4-bromophenyl)carbamoylmethyl]-1,3-thiazol-4-ine hydrochloride (R1=4-Br, R$_2$=4-Cl, 2-F, 5-OCH(CH$_3$)$_2$, R$_3$=CH$_3$, HX=HCl).

Starting materials: methylisothiocyanate, 4-chloro-5-isopropoxy-2-fluoroaniline, 4-chloro-3-oxo-N-(4-bromophenyl)butane amide Yield: 85% Melting point: 201–205° C. $^1$H NMR (DMSO-d$_6$) δ 1.27 (d, 6H, isopropoxy (CH$_3$)$_2$), 3.67 (s, 3H, 3-CH$_3$), 4.00 (s. 2H, 4-CH$_2$), 4.54~4.65 (m, 1H, CH), 6.87 (s, 1H, 5-vinyl H), 7.32~7.67 (m, 6H, ArH), 10.93 (s, 1H, NH); IR(KBr) 3374 (NH), 1678 (C=O), 1584 (C=C) cm$^{-1}$.

[Compound 186]
2-(2,4-dimethylphenylimino)-3-methyl-4-[N-(4-trifluoromethoxyphenyl)carbamoylmethyl]-1,3-thiazol-4-ine hydrochloride (R1=4-Br, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(4-trifluoromethoxyphenyl)butane amide Yield: 88% Melting point: 203–207° C. $^1$H NMR (DMSO-d$_6$) δ 2.29 and 2.33 (2s, 6H, ArCH$_3$), 3.79 (s, 3H, 3-CH$_3$), 4.10 (s, 2H, 4-CH$_2$), 7.00 (s, 1H, 5-vinyl H), 7.20~7.88 (m, 7H, ArH), 11.2 (s, 1H, NH); IR(KBr) 3424 (NH), 1680 (C=O), 1560 (C=C) cm$^{-1}$.

[Compound 187]
2-(4-bromophenylimino)-3-methyl-4-[N-(4-trifluoromethoxyphenyl)carbamoylmethyl]-1,3-thiazol-4-ine hydrochloride (R1=4-OCF$_3$, R$_2$=4-Br, R$_3$=CH$_3$, HX=HCl).

Starting materials: methylisothiocyanate, 4-bromoaniline, 4-chloro-3-oxo-N-(4-trifluoromethoxyphenyl)butane amide Yield: 39% Melting point: 205–208° C. $^1$H NMR (DMSO-d$_6$) δ 3.78 (s, 3H, 3-CH$_3$), 4.10 (s, 2H, 4-CH$_2$), 7.06 (s, 1H, 5-vinyl H), 7.32~7.80 (m, 8H, ArH), 11.09 (s, 1H, NH); IR(KBr) 3426 (NH), 1681 (C=O), 1592 (C=C) cm$^{-1}$.

[Compound 188]
2-(3-chloro-4-fluorophenylimino)-3-methyl-4-[N-(4-trifluoromethoxyphenyl)carbamoylmethyl]-1,3-thiazol-4-ine hydrochloride (R1=4-OCF$_3$, R$_2$=3-Cl, 4-F, R$_3$=CH$_3$, HX=HCl).

Starting materials: methylisothiocyanate, 3-chloro-4-fluoroaniline, 4-chloro-3-oxo-N-(4-trifluoromethoxyphenyl)butane amide Yield: 38% Melting point: 217–218° C. $^1$H NMR (DMSO-d$_6$) δ 3.80 (s, 3H, 3-CH$_3$), 4.05 (s. 2H, 4-CH$_2$), 6.99 (s, 1H, 5-vinyl H), 7.32~7.77 (m, 7H, ArH), 10.99 (s, 1H, NH); IR(KBr) 3426 (NH), 1659 (C=O), 1563 (C=C) cm$^{-1}$.

[Compound 189]
2-(3-fluorophenylimino)-3-methyl-4-[N-(4-trifluoromethoxyphenyl)carbamoylmethyl]-1,3-thiazol-4-ine hydrochloride (R1=4-OCF$_3$, R$_2$=3-F, R$_3$=CH$_3$, HX=HCl).

Starting materials: methylisothiocyanate, 3-fluoroaniline, 4-chloro-3-oxo-N-(4-trifluoromethoxyphenyl)butane amide Yield: 42% Melting point: 225–227° C. $^1$H NMR (DMSO-d$_6$) δ 3.79 (s, 3H, 3-CH$_3$), 4.08 (s. 2H, 4-CH$_2$), 7.08 (s, 1H, 5-vinyl H), 7.20~7.80 (m, 7H, ArH), 11.09 (s, 1H, NH); IR(KBr) 3424 (NH), 1658 (C=O), 1582 (C=C) cm$^{-1}$.

[Compound 1901]
2-(4-trifluoromethylphenylimino)-3-methyl-4-[N-(4-trifluoromethoxyphenyl)carbamoylmethyl]-1,3-thiazol-4-ine hydrochloride (R1=4-OCF$_3$, R$_2$=4-OCF$_3$, R$_3$=CH$_3$, HX=HCl).

Starting materials: methylisothiocyanate, 4-trifluoromethylaniline, 4-chloro-3-oxo-N-(4-trifluoromethoxyphenyl)butane amide Yield: 38% Melting point: 217–219° C. $^1$H NMR (DMSO-d$_6$) δ 3.78 (s, 3H, 3-CH$_3$), 4.08 (s. 2H, 4-CH2), 7.05 (s, 1H, 5-vinyl H), 7.32~7.88 (m, 8H, ArH), 11.03 (s, 1H, NH); IR(KBr) 3424 (NH), 1687 (C=O), 1589 (C=C) cm$^{-1}$.

[Compound 191]
2-(3-bromophenylimino)-3-methyl-4-[N-(4-trifluoromethoxyphenyl)carbamoylmethyl]-1,3-thiazol-4-ine hydrochloride (R1=4-OCF$_3$, R$_2$=3-Br, R$_3$=CH$_3$, HX=HCl).

Starting materials: methylisothiocyanate, 3-bromoaniline, 4-chloro-3-oxo-N-(4-trifluoromethoxyphenyl)butane amide Yield: 57% Melting point: 220–224° C. $^1$H NMR (DMSO-d$_6$) δ 4.40 (s, 3H, 3-CH$_3$), 4.75 (s. 2H, 4-CH$_2$), 7.65 (s, 1H, 5-vinyl H), 8.07~8.50 (m, 8H, ArH), 11.55 (s, 1H, NH); IR(KBr) 3448 (NH), 1656 (C=O), 1555 (C=C) cm$^{-1}$.

[Compound 192]
2-(2,4-difluorophenylimino)-3-methyl-4-[N-(4-trifluoromethoxyphenyl)carbamoylmethyl]-1,3-thiazol-4-ine hydrochloride (R1=4-OCF$_3$, R$_2$=2-F, 4-F, R$_3$=CH$_3$, HX=HCl).

Starting materials: methylisothiocyanate, 2,4-difluoroaniline, 4-chloro-3-oxo-N-(4-trifluoromethoxyphenyl)butane amide Yield: 58% Melting point: 205–209° C. $^1$H NMR (DMSO-d$_6$) δ 3.79 (s, 3H, 3-CH$_3$), 4.09 (s. 2H, 4-CH$_2$), 6.90 (s, 1H, 5-vinyl H), 7.23~7.78 (m, 7H, ArH), 11.02 (s, 1H, NH); IR(KBr) 3424 (NH), 1676 (C=O), 1582 (C=C) cm$^{-1}$.

[Compound 193]
2-(2-methoxy-5-methylphenylimino)-3-methyl-4-[N-(4-trifluoromethoxyphenyl)carbamoylmethyl]-1,3-thiazol-4-ine hydrochloride (R1=4-OCF$_3$, R$_2$=2-OCH$_3$, 5-CH$_3$, R$_3$=CH$_3$, HX=HCl).

Starting materials: methylisothiocyanate, 2-methoxy-5-methylaniline, 4-chloro-3-oxo-N-(4-trifluoromethoxyphenyl)butane amide Yield: 76% Melting point: 199–204° C. $^1$H NMR (DMSO-d$_6$) δ 2.28 (s, 3H, ArCH$_3$), 3.76 (s, 3H, 3-CH$_3$), 3.80 (s, 3H, 2-OCH$_3$), 4.07 (s. 2H, 4-CH$_2$), 7.03 (s, 1H, 5-vinyl H), 7.20~7.80 (m, 7H, ArH), 11.12 (s, 1H, NH); IR(KBr) 3400 (NH), 1686 (C=O), 1583 (C=C) cm$^{-1}$.

[Compound 194]
2-(4-chloro-5-isopropoxy-2-fluorophenylimino)-3-methyl-4-[N-(4-trifluoromethoxyphenyl)carbamoylmethyl]-1,3-thiazol-4-ine hydrochloride (R1=4-OCF$_3$, R$_2$=4-Cl, 2-F, 5-OCH(CH$_3$)$_2$, R$_3$=CH$_3$, HX=HCl).

Starting materials: methylisothiocyanate, 4-chloro-5-isopropoxy-2-fluoroaniline, 4-chloro-3-oxo-N-(4-trifluoromethoxyphenyl)butane amide Yield: 50% Melting point: 200–203° C. $^1$H NMR (CDCl,) δ 1.28 (d, 6H, isopropoxy (CH$_3$)$_2$), 4.20 (s. 2H, 4-CH$_2$), 4.30 (s, 3H, 3-CH$_3$), 4.44~4.52 (m, 1H, CH), 6.83 (s, 1H, 5-vinyl H), 7.10~7.84 (m, 6H, ArH), 10.86 (s, 1H, NH); IR(KBr) 3424 (NH), 1682 (C=O), 1592 (C=C) cm$^{-1}$.

[Compound 195]
2-(4-chloro-2-fluorophenylimino)-3-methyl-4-[N-(4-trifluoromethoxyphenyl)carbamoylmethyl]-1,3-thiazol-4-ine hydrochloride (R1=4-OCF$_3$, R$_2$=4-Cl, 2-F, R$_3$=CH$_3$, HX=HCl).

Starting materials: methylisothiocyanate, 4-chloro-2-fluoroaniline, 4-chloro-3-oxo-N-(4-trifluoromethoxyphenyl)butane amide Yield: 98% Melting point: 201–208° C. $^1$H NMR (DMSO-d$_6$) δ 3.70 (s, 3H, 3-CH$_3$), 4.00 (s. 2H, 4-CH$_2$), 6.84 (s, 1H, 5-vinyl H), 7.32~7.77 (m, 7H, ArH), 10.98 (s, 1H, NH); IR(KBr) 3424 (NH), 1686 (C=O), 1564 (C=C) cm$^{-1}$.

[Compound 196]
2-(2,4-dimethylphenylimino)-3-methyl-4-[N-(4-methoxyphenyl)carbamoylmethyl]-1,3-thiazol-4-ine hydrochloride (R1=4-OCH$_3$, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(4-methoxyphenyl) butane amide Yield: 76% Melting point: 170–174° C. $^1$H NMR (DMSO-d$_6$) δ 2.30 and 2.33 (2s, 6H, 2×ArCH$_3$), 3.72 (s, 3H, 3-CH$_3$), 3.81 (s, 3H, 4-OCH$_3$) 4.00 (s, 2H, 4-CH$_2$), 6.98 (s, 1H, 5-vinyl H), 6.88~7.58 (m, 7H, ArH), 10.69 (s, 1H, NH); IR(KBr) 3448 (NH), 1664 (C=O), 1582 (C=C) cm$^{-1}$.

[Compound 1971]
2-[4-(n-butyl)phenylimino]-3-methyl-4-[N-(4-methoxyphenyl)carbamoylmethyl]-1,3-thiazol-4-ine hydrochloride (R1=4-OCH$_3$, R$_2$=4-(CH$_2$)$_3$CH$_3$, R$_3$=CH$_3$, HX=HCl).

Starting materials: methylisothiocyanate, 4-(n-butyl)aniline, 4-chloro-3oxo-N-(4-methoxyphenyl)butane amide Yield: 60% Melting point: 230–232° C. $^1$H NMR (DMSO-d$_6$) δ 0.91 (t, 3H, butyl CH$_3$), 1.28~1.95 (m, 2H, CH$_2$), 1.53~1.60 (m, 2H, CH$_2$), 2.59~2.65 (m, 2H, CH$_2$), 3.71 (s, 3H, 4-OCH$_3$), 3.78 (s, 3H, 3-CH$_3$), 4.00 (s, 2H, 4-CH$_2$), 6.98 (s, 1H, 5-vinyl H), 6.88~7.57 (m, 8H, ArH), 10.60 (s, 1H, NH); IR(KBr) 3426 (NH), 1658 (C=O), 1600 (C=C) cm$^{-1}$.

[Compound 198]
2-(2-methoxy-5-methylphenylimino)-3-methyl-4-[N-(4-methoxyphenyl)carbamoylmethyl]-1,3-thiazol-4-ine hydrochloride (R1=4-OCH$_3$, R$_2$=2-OCH$_3$, 5-CH$_3$, R$_3$=CH$_3$, HX=HCl).

Starting materials: methylisothiocyanate, 2-methoxy-5-methylaniline, 4-chloro-3-oxo-N-(4-methoxyphenyl)butane amide Yield: 44% Melting point: 180–184° C. $^1$H NMR (DMSO-d$_6$) δ 2.28 (s, 3H, ArCH$_3$), 3.72 (s, 3H, 3-CH$_3$), 3.78 (s, 3H, 4-OCH$_3$), 3.81 (s, 3H, 2-OCH$_3$) 4.02(s, 2H, 4-CH$_2$), 7.01 (s, 1H, 5-vinyl H), 6.88~7.58 (m, 7H, ArH), 10.70 (s, 1H, NH); FT-IR(KBr) 3448 (NH), 1690 (C=O), 1574 (C=C) cm$^{-1}$.

[Compound 199]
2-(2,4-dimethylphenylimino)-3-methyl-4-[N-(4-phenoxyphenyl)carbamoylmethyl]-1,3-thiazol-4-ine hydrochloride (R1=4-OC$_6$H$_5$, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(4-phenoxyphenyl)butane amide Yield: 73% Melting point: 184–187° C. $^1$H NMR (DMSO-d$_6$) δ 2.24 and 2.33 (2s, 6H, 2×ArCH$_3$), 3.81 (s, 3H, 3-CH$_3$), 4.00-(s, 2H, 4-CH$_2$), 6.95 (s, 1H, 5-vinyl H), 6.98~7.70 (m, 12H, ArH), 10.90 (s, 1H, NH); IR(KBr) 3426 (NH), 1670 (C=O), 1578 (C=C) cm$^{-1}$.

[Compound 200]
2-(2-methoxy-5-methyl phenylimino)-3-methyl-4-[N-(4-phenoxyphenyl)carbamoylmethyl]-1,3-thiazol-4-ine hydrochloride (R1=4-OC$_6$H$_5$, R$_2$=2-OCH3, 5-CH$_3$, R$_3$=CH$_3$, HX=HCl).

Starting materials: methylisothiocyanate, 2-methoxy-5-methylaniline, 4-chloro-3-oxo-N-(4-phenoxyphenyl)butane amide Yield: 53% Melting point: 198–203° C. $^1$H NMR (DMSO-d$_6$) δ 2.28 (s, 3H, ArCH$_3$), 3.77 (s, 3H, 2-OCH$_3$), 3.80 (s, 3H, 3-CH$_3$), 4.05 (s, 2H, 4-CH$_2$), 6.95 (s, 1H, 5-vinyl H), 6.98~7.68 (m, 12H, ArH), 10.7 (s, 1H, NH); IR(KBr) 3428 (NH), 1684 (C=O), 1598 (C=C) cm$^{-1}$.

[Compound 201]
2-(3-bromophenylimino)-3-methyl-4-[N-(4-methoxyphenyl)carbamoylmethyl]-1,3-thiazol-4-ine hydrochloride (R1=4-OCH$_3$, R$_2$=3-Br, R$_3$=CH$_3$, HX=HCl).

Starting materials: methylisothiocyanate, 3-bromoaniline, 4-chloro-3-oxo-N-(4-methoxyphenyl)butane amide Yield: 50% Melting point: 223–225° C. $^1$H NMR (DMSO-d$_6$) δ 3.72 (s, 3H, 3-CH$_3$), 3.75 (s, 3H, 4-OCH$_3$), 3.99 (s, 2H, 4-CH$_2$), 6.99 (s, 1H, 5-vinyl H), 6.88~7.80 (m, 8H, ArH), 10.55 (s, 1H, NH); IR(KBr) 3426 (NH), 1658 (C=O), 1562 (C=C) cm$^{-1}$.

[Compound 202]
2-(3-chloro-4-fluorophenylimino)-3-methyl-4-[N-(4-methoxyphenyl)carbamoylmethyl]-1,3-thiazol-4-ine hydrochloride (R1=4-OCH$_3$, R$_2$=3-Cl, 4-F, R$_3$=CH$_3$, HX=HCl).

Starting materials: methylisothiocyanate, 3-chloro-4-fluoroaniline, 4-chloro-3-oxo-N-(4-methoxyphenyl)butane amide Yield: 37% Melting point: 224–231° C. $^1$H NMR (DMSO-d$_6$) δ 3.72 (s, 3H, 3-CH$_3$), 3.72 (s, 3H, 4-OCH$_3$), 3.97 (s, 2H, 4-CH$_2$), 6.95 (s, 1H, 5-vinyl H), 6.87~7.76 (m, 7H, ArH), 10.51 (s, 1H, NH); IR(KBr) 3448 (NH), 1656 (C=O), 1581 (C=C) cm$^{-1}$.

[Compound 203]
2-(3-fluorophenylimino)-3-methyl-4-[N-(4-methoxyphenyl)carbamoylmethyl]-1,3-thiazol-4-ine hydrochloride (R1=4-OCH$_3$, R$_2$=3-F, R$_3$=CH$_3$, HX=HCl).

Starting materials: methylisothiocyanate, 3-fluoroaniline, 4-chloro-3-oxo-N-(4-methoxyphenyl)butane amide Yield: 35% Melting point: 228–232° C. $^1$H NMR (DMSO-d$_6$) δ 3.72 (s, 3H, 3-CH$_3$), 3.76 (s, 3H, 4-OCH$_3$), 3.99 (s, 2H, 4-CH$_2$), 7.01 (s, 1H, 5-vinyl H), 6.88~7.55 (m, 8H, ArH), 10.55 (s, 1H, NH); IR(KBr) 3448 (NH), 1656 (C=O), 1582 (C=C) cm$^{-1}$.

[Compound 204]
2-(2-fluorophenylimino)-3-methyl-4-[N-(4-methoxyphenyl)carbamoylmethyl]-1,3-thiazol-4-ine hydrochloride (R1=4-OCH$_3$, R$_2$=2-F, R$_3$=CH$_3$, HX=HCl).

Starting materials: methylisothiocyanate, 2-fluoroaniline, 4-chloro-3-oxo-N-(4-methoxyphenyl)butane amide Yield: 68% Melting point: 190–195° C. $^1$H NMR (DMSO-d$_6$) δ 3.72 (s, 3H, 3-CH$_3$), 3.73 (s, 3H, 4-OCH$_3$), 3.96 (s, 2H, 4-CH$_2$), 6.91 (s, 1H, 5-vinyl H), 6.88~7.57 (m, 8H, ArH), 10.52 (s, 1H, NH); IR(KBr) 3448 (NH), 1670 (C=O), 1592 (C=C) cm$^{-1}$.

[Compound 205]
2-(4-trifluoromethylphenylimino)-3-methyl-4-[N-(4-methoxyphenyl)carbamoylmethyl]-1,3-thiazol-4-ine hydrochloride (R1=4-OCH$_3$, R$_2$=4-CF$_3$, R$_3$=CH$_3$, HX=HCl).

Starting materials: methylisothiocyanate, 4-trifluoromethylaniline, 4-chloro-3-oxo-N-(4-methoxyphenyl)butane amide Yield: 39% Melting point: 226–232° C. $^1$H NMR (DMSO-d$_6$) δ 3.72 (s, 3H, 3-CH$_3$), 3.77 (s, 3H, 4-OCH$_3$), 4.00 (s, 2H, 4-CH$_2$), 7.01 (s, 1H, 5-vinyl H), 6.88~7.88 (m, 8H, ArH), 10.56 (s, 1H, NH); IR(KBr) 3448 NH), 1656 C=O), 1592 C=C) cm$^{-1}$.

[Compound 206]
2-(2,4-difluorophenylimino)-3-methyl-4-[N-(4-methoxyphenyl)carbamoylmethyl]-1,3-thiazol-4-ine hydrochloride (R1=4-OCH$_3$, R$_2$=2-F, 4-F, R$_3$=CH$_3$, HX=HCl).

Starting materials: methylisothiocyanate, 2,4-difluoroaniline, 4-chloro-3-oxo-N-(4-methoxyphenyl) butane amide Yield: 49% Melting point: 178–182° C. $^1$H NMR (DMSO-d$_6$) δ 3.72 (s, 3H, 3-CH$_3$), 3.72 (s, 3H, 4-OCH$_3$), 3.97 (s, 2H, 4-CH$_2$), 6.92 (s, 1H, 5-vinyl H), 6.88~7.63 (m, 8H, ArH), 10.55 (s, 1H, NH); IR(KBr) 3446 (NH), 1650 (C=O), 1580 (C=C) cm$^{-1}$.

[Compound 207]
2-(4-chloro-2-fluorophenylimino)-3-methyl-4-[N-(4-methoxyphenyl)carbamoylmethyl]-1,3-thiazol-4-ine hydrochloride (R$_1$=4-OCH$_3$, R$_2$=4-Cl, 2-F, R$_3$=CH$_3$, HX=HCl).

Starting materials: methylisothiocyanate, 4-chloro-2-fluoroaniline, 4-chloro-3-oxo-N-(4-methoxyphenyl)butane amide Yield: 37% Melting point: 201–205° C. $^1$H NMR (DMSO-d$_6$) δ 3.69 (s, 3H, 4-OCH$_3$), 3.72 (s, 3H, 3-CH$_3$), 3.95 (s, 2H, 4-CH$_2$), 6.86 (s, 1H, 5-vinyl H), 6.88~7.7 (m, 7H, ArH); IR(KBr) 3448 (NH), 1668 (C=O), 1560 (C=C) cm$^{-1}$.

[Compound 208]
2-(4-chloro-5-isopropoxy-2-fluorophenylimino)-3-methyl-4-[N-(4-methoxyphenyl)carbamoylmethyl]-1,3-thiazol-4-ine hydrochloride (R1=4-OCH$_3$, R$_2$=4-Cl, 2-F, 5-OCH(CH$_3$)$_2$, R$_3$=CH$_3$, HX=HCl).

Starting materials: methylisothiocyanate, 4-chloro-5-isopropoxy-2-fluoroaniline, 4-chloro-3-oxo-N-(4-methoxyphenyl)butane amide Yield: 34% Melting point: 212–216° C. $^1$H NMR (DMSO-d$_6$) δ1.28 (d, 6H, isopropoxy (CH$_3$)$_2$), 3.65 (s, 3H, 4-OCH$_3$), 3.72 (s, 3H, 3-CH$_3$), 3.92 (s, 2H, 4-CH$_2$), 4.56~4.60 (m, 1H, CH), 6.79 (s, 1H, 5-vinyl H), 6.88~7.50 (m, 6H, ArH), 10.48 (s, 1H, NH); IR(KBr) 3424 (NH), 1654 (C=O), 1575 (C=C) cm$^{-1}$.

[Compound 209]
2-(4-trifluoromethoxyphenylimino)-3-methyl-4-[N-(4-methoxyphenyl)carbamoylmethyl]-1,3-thiazol-4-ine hydrochloride (R1=4-OCH$_3$, R$_2$=4-OCF$_3$, R$_3$=CH$_3$, HX=HCl).

Starting materials: methylisothiocyanate, 4-trifluoromethoxyaniline, 4-chloro-3-oxo-N-(4-methoxyphenyl)butane amide.

Yield: 24% Melting point: 232–236° C. $^1$H NMR (DMSO-d$_6$) δ 3.72 (s, 3H, 3-CH$_3$), 3.78 (s, 3H, 4-OCH$_3$), 4.00 (s, 2H, 4-CH$_2$), 7.01 (s, 1H, 5-vinyl H), 6.88~7.65 (m, 8H, ArH), 10.57 (s, 1H, NH); IR(KBr) 3448 (NH), 1656 (C=O), 1580 (C=C) cm$^{-1}$.

[Compound 210]
2-(3-fluorophenylimino)-3-methyl-4-[N-(4-cyanophenyl)carbamoylmethyl]4-thiazoline hydrochloride (R1=4-CN, R$_2$=3-F, R$_3$=CH$_3$, HX=HCl).

Starting materials: methylisothiocyanate, 3-fluoroaniline, 4-chloro-3-oxo-N-(4-cyanophenyl)butane amide Yield: 59% Melting point: 216~219° C. $^1$H NMR (DMSO-d$_6$) δ 3.78 (s, 3H, 3-CH$_3$), 4.14 (s, 2H, 4-CH$_2$), 7.09 (s, 1H, 5-vinyl H), 7.22~7.88 (m, 8H, ArH), 11.39 (s, 1H, NH); IR(KBr) 3428 (NH), 1664 (C=O), 1600 (C=C) cm$^{-1}$.

[Compound 211]
2-(4-fluorophenylimino)-3-methyl-4-[N-(4-cyanophenyl)carbamoylmethyl]-4-thiazoline hydrochloride (R1=4-CN, R$_2$=4-F, R$_3$=CH$_3$, HX=HCl).

Starting materials: methylisothiocyanate, 4-fluoroaniline, 4-chloro-3-oxo-N-(4-cyanophenyl)butane amide Yield: 57% Melting point: 239~240° C. $^1$H NMR (DMSO-d$_6$) δ 3.78 (s, 3H, 3-CH$_3$), 4.20 (s, 2H, 4-CH$_2$), 7.07 (s, 1H, 5-vinyl H), 7.37~7.88 (m, 8H, ArH), 11.44 (s, 1H, NH); IR(KBr) 3428 (NH), 1668 (C=O), 1596 (C=C) cm$^{-1}$.

[Compound 212]
2-(2-fluorophenylimino)-3-methyl-4-[N-(4-cyanophenyl)carbamoylmethyl]-4-thiazoline hydrochloride (R1=4-CN, R$_2$=2-F, R$_3$=CH$_3$, HX=HCl).

Starting materials: methylisothiocyanate, 2-fluoroaniline, 4-chloro-3-oxo-N-(4-cyanophenyl)butane amide Yield: 60% Melting point: 214~219° C. $^1$H NMR (DMSO-d$_6$) δ 3.75 (s, 3H, 3-CH$_3$), 4.11 (s, 2H, 4-CH$_2$), 7.00 (s, 1H, 5-vinyl H), 7.35~7.88 (m, 8H, ArH), 11.37 (s, 1H, NH); IR(KBr) 3435 (NH), 1704 (C=O), 1598 (C=C) cm$^{-1}$.

[Compound 213]
2-(4-cyanophenylimino)-3-methyl-4-[N-(4-cyanophenyl)carbamoylmethyl]-4-thiazoline hydrochloride (R1=4-CN, R$_2$=4-CN, R$_3$=CH$_3$, HX=HCl).

Starting materials: methylisothiocyanate, 4-cyanoaniline, 4-chloro-3-oxo-N-(4-cyanophenyl)butane amide Yield: 35% Melting point: 238° C. $^1$H NMR (DMSO-d$_6$) δ 3.72 (s, 3H, 3-CH$_3$), 4.10 (s, 2H, 4-CH$_2$), 7.00 (s, 1H, 5-vinyl H), 7.59~7.94 (m, 8H, ArH), 11.30 (s, 1H, NH); IR(KBr) 3426 (NH), 1672 (C=O), 1598 (C=C) cm$^{-1}$.

[Compound 214]
2-(4-bromophenylimino)-3-methyl-4-[N-(4-cyanophenyl)carbamoylmethyl]-4-thiazoline hydrochloride (R1=4-CN, R$_2$=4-Br, R$_3$=CH$_3$, HX=HCl).

Starting materials: methylisothiocyanate, 4-bromoaniline, 4-chloro-3-oxo-N-(4-cyanophenyl)butane amide Yield: 49% Melting point: 239° C. $^1$H NMR (DMSO-d$_6$) δ 3.77 (s, 3H, 3-CH$_3$), 4.14 (s, 2H, 4-CH$_2$), 7.08 (s, 1H, 5-vinyl H), 7.45~7.88 (m, 8H, ArH), 11.40 (s, 1H, NH); IR(KBr) 3426 (NH), 1702 (C=O), 1598 (C=C) cm$^{-1}$.

[Compound 215]
2-(4-trifluoromethoxyphenylimino)-3-methyl-4-[N-(4-cyanophenyl)carbamoylmethyl]-4-thiazoline hydrochloride (R1=4-CN, R$_2$=4-OCF$_3$, R$_3$=CH$_3$, HX=HCl).

Starting materials: methylisothiocyanate, 4-trifluoromethoxyaniline, 4chloro-3-oxo-N-(4-cyanophenyl)butane amide Yield: 54% Melting point: 196~199° C. $^1$H NMR (DMSO-d$_6$) δ 3.76 (s, 3H, 3-CH$_3$), 4.12 (s, 2H, 4-CH$_2$), 7.05 (s, 1H, 5-vinyl H), 7.52~7.87 (m, 8H, ArH), 11.91 (s, 1H, NH); IR(KBr) 3428 (NH), 1684 (C=O), 1600 (C=C) cm$^{-1}$.

[Compound 216]
2-(4-chlorophenylimino)-3-methyl-4-[N-(4-cyanophenyl)carbamoylmethyl]-4-thiazoline hydrochloride (R1=4-CN, R$_2$=4-Cl, R$_3$=CH$_3$, HX=HCl).

Starting materials: methylisothiocyanate, 4-chloroaniline, 4-chloro-3-oxo-N-(4-cyanophenyl)butane amide Yield: 48% Melting point: 245~246° C. $^1$H NMR (DMSO-d$_6$) δ 3.77 (s, 3H, 3-CH$_3$), 4.20 (s, 2H, 4-CH$_2$), 7.08 (s, 1H, 5-vinyl H), 7.53~7.88 (m, 8H, ArH), 11.49 (s, 1H, NH); IR(KBr) 3436 (NH), 1702 (C=O), 1564 (C=C) cm$^{-1}$.

[Compound 217]
2-(3.5-dichlorophenylimino)-3-methyl-4-[N-(4-cyanophenyl)carbamoylmethyl]-4-thiazoline hydrochloride (R1=4-CN, R$_2$=2-Cl, 4-Cl, R$_3$=CH$_3$, HX=HCl).

Starting materials: methylisothiocyanate, 3.5-dichloroaniline, 4-chloro-3-oxo-N-(4-cyanophenyl)butane amide Yield: 38% Melting point: 249~250° C. $^1$H NMR (DMSO-d$_6$) δ 3.68 (s, 3H, 3-CH$_3$), 4.09 (s, 2H, 4-CH$_2$), 6.98 (s, 1H, 5-vinyl H), 7.50~7.86 (m, 7H, ArH), 11.27 (s, 1H, NH); IR(KBr) 3436 (NH), 1688 (C=O), 1598 (C=C) cm$^{-1}$.

[Compound 218]
2-(4-phenoxyphenylimino)-3-methyl-4-[N-(4-cyanophenyl)carbamoylmethyl]-4-thiazoline hydrochloride (R1=4-CN, R$_2$=OC$_6$H$_5$, R$_3$=CH$_3$, HX=HCl).

Starting materials: methylisothiocyanate, 4-phenoxyaniline, 4-chloro-3-oxo-N-(4-cyanophenyl)butane amide Yield: 56% Melting point: 213~216° C. $^1$H NMR (DMSO-d$_6$) δ 3.77 (s, 3H, 3-CH$_3$), 4.13 (s, 2H, 4-CH$_2$), 7.06 (s, 1H, 5-vinyl H), 7.08~7.88 (m, 13H, ArH), 11.40 (s, 1H, NH); IR(KBr) 3424 (NH), 1690 (C=O), 1596 (C=C) cm$^{-1}$.

[Compound 219]
2-(2,4-dimethylphenylimino)-3-methyl-4-[N-(4-cyanophenyl)carbamoylmethyl]-4-thiazoline hydrochloride (R1=4-CN, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(4-cyanophenyl)butane amide Yield: 79% Melting point: 216~221° C. $^1$H NMR (DMSO-d$_6$) δ 2.29 and 2.33 (2s, 6H, 2×ArCH$_3$), 3.79 (s, 3H, 3-CH$_3$), 4.12 (s, 2H, 4-CH$_2$), 7.02 (s, 1H, 5-vinyl H), 7.10~7.89 (m, 7H, ArH) 11.49 (s, 1H, NH); IR(KBr) 3424 (NH), 1702 (C=C), 1598 (C=C) cm$^{-1}$.

[Compound 220]

2-(3-chloro-4-fluorophenylimino)-3-methyl-4-[N-(4-cyanophenyl)carbamoylmethyl]-4-thiazoline hydrochloride (R1=4-CN, R$_2$=3-Cl, 4-F, R$_3$=CH$_3$, HX=HCl).

Starting materials: methylisothiocyanate, 3-chloro-4-fluoroaniline, 4-chloro-3-oxo-N-(4-cyanophenyl)butane amide Yield: 50% Melting point: 221~225° C. $^1$H NMR (DMSO-d$_6$) δ 3.72 (s, 3H, 3-CH$_3$), 4.11 (s, 2H, 4-CH$_2$), 7.02 (s, 1H, 5-vinyl H), 7.50~7.87 (m, 7H, ArH), 11.31 (s, 1H, NH); IR(KBr) 3426 (NH), 1686 (C=O), 1600 (C=C) cm$^{-1}$.

[Compound 221]

2-[4-(n-butyl)phenylimino]-3-methyl-4-[N-(4-cyanophenyl)carbamoylmethyl]-4-thiazoline hydrochloride (R1=4-CN, R$_2$=4-(CH$_2$)$_3$CH$_3$, R$_3$=CH$_3$, HX=HCl).

Starting materials: methylisothiocyanate, 4-(n-butyl)aniline, 4-chloro-3-oxo-N-(4-cyanophenyl)butane amide Yield: 42% Melting point: 245~248° C. $^1$H NMR (DMSO-d$_6$) δ 0.90 (t, 3H, butyl CH$_3$), 1.28~1.35 (m, 2H, CH$_2$), 1.52~1.60 (m, 2H, CH$_2$), 2.49~2.65 (m, 2H, CH$_2$), 3.77 (s, 3H, 3-CH$_3$), 4.13 (s, 2H, 4-CH$_2$), 7.06 (s, 1H, 5-vinyl H), 7.34~7.88 (m, 8H, ArH), 11.40 (s, 1H, NH); IR(KBr) 3426 (NH), 1672 (C=O), 1596 (C=C) cm$^{-1}$.

[Compound 222]

2-(3-bromophenylimino)-3-methyl-4-[N-(4-cyanophenyl)carbamoylmethyl]-4-thiazoline hydrochloride (R1=4-CN, R$_2$=3-Br, R$_3$=CH$_3$, HX=HCl).

Starting materials: methylisothiocyanate, 3-bromoaniline, 4-chloro-3-oxo-N-(4-cyanophenyl)butane amide Yield: 36% Melting point: 234~238° C. $^1$H NMR (DMSO-d$_6$) δ 3.75 (s, 3H, 3-CH$_3$), 4.12 (s, 2H, 4-CH$_2$), 7.05 (s, 1H, 5-vinyl H), 7.45~7.84 (m, 8H, ArH), 11.34 (s, 1H, NH); IR(KBr) 3428 (NH), 1692 (C=O), 1596 (C=C) cm$^{-1}$.

[Compound 223]

2-(4-chloro-2-fluorophenylimino)-3-methyl-4-[N-(4-cyanophenyl)carbamoylmethyl]-4-thiazoline hydrochloride (R1=4-CN, R$_2$=4-Cl, 2-F, R$_3$=CH$_3$, HX=HCl).

Starting materials: methylisothiocyanate, 4-chloro-2-fluoroaniline, 4-chloro-3-oxo-N-(4-cyanophenyl)butane amide Yield: 33% Melting point: 217~222° C. $^1$H NMR (DMSO-d$_6$) δ 3.66 (s, 3H, 3-CH$_3$), 4.06 (s, 2H, 4-CH$_2$), 6.86 (s, 1H, 5-vinyl H), 7.39~7.87 (m, 7H, ArH), 11.29 (s, 1H, NH); IR(KBr) 3436 (NH), 1704 (C=O), 1598 (C=C) cm$^{-1}$.

[Compound 224]

2-(2-methoxy-5-methyl phenylimino)-3-methyl-4-[N-(4-cyanophenyl)carbamoylmethyl]-4-thiazoline hydrochloride (R1=4-CN, R$_2$=2-OCH$_3$, 5-CH$_3$, R$_3$=CH$_3$, HX=HCl).

Starting materials: methylisothiocyanate, 2-methoxy-5-methylaniline, 4-chloro-3-oxo-N-(4-cyanophenyl)butane amide Yield: 83% Melting point: 217~219° C. $^1$H NMR (DMSO-d$_6$) δ 2.28 (s, 3H, ArCH$_3$), 3.75 (s, 3H, 3-CH$_3$), 3.79 (s, 3H, 2-OCH$_3$), 4.13 (s, 2H, 4-CH$_2$), 7.10 (s, 1H, 5-vinyl H), 7.16~7.88 (m, 7H, ArH) 11.41 (s, 1H, NH); IR(KBr) 3426 (NH), 1704 (C=O), 1596 (C=C) cm$^{-1}$.

[Compound 225]

2-(2,4-difluorophenylimino)-3-methyl-4-[N-(4-cyanophenyl)carbamoylmethyl]-4-thiazoline hydrochloride (R1=4-CN, R$_2$=2-F, 4-F, R$_3$=CH$_3$, HX=HCl).

Starting materials: methylisothiocyanate, 2.4-difluoroaniline, 4-chloro-3-oxo-N-(4-cyanophenyl)butane amide Yield: 39% Melting point: 239~240° C. $^1$H NMR (DMSO-d$_6$) δ 3.72 (s, 3H, 3-CH$_3$), 4.09 (s, 2H, 4-CH$_2$), 6.97 (s, 1H, 5-vinyl H), 7.24~7.87 (m, 7H, ArH), 11.32 (s, 1H, NH); IR(KBr) 3435 (NH), 1702 (C=O), 1600 (C=C) cm$^{-1}$.

[Compound 226]

2-(4-chloro-5-isopropoxy-2-fluorophenylimino)-3-methyl-4-[N-(4-cyanophenyl)carbamoylmethyl]-4-thiazoline hydrochloride (R1=4-NO$_2$, R$_2$=4-Cl, 2-F, 5-OCH(CH$_3$)$_2$, R$_3$=CH$_3$, HX=HCl).

Starting materials: methylisothiocyanate, 4-chloro-5-isopropoxy-2-fluoroaniline, 4-chloro-3-oxo-N-(4-cyanophenyl)butane amide Yield: 85% Melting point: 231~234° C. $^1$H NMR (DMSO-d$_6$) δ 1.27 (d, 6H, isopropoxy (CH$_3$)$_2$), 3.70 (s, 3H, 3-CH$_3$), 4.09 (s, 2H, 4-CH$_2$), 4.54~4.66 (m, 1H, CH), 6.93 (s, 1H, 5-vinyl H), 7.38~7.87 (m, 6H, ArH), 11.37 (s, 1H, NH); IR(KBr) 3426 (NH), 1702 (C=O), 1598 (C=C) cm$^{-1}$.

[Compound 227]

2-(2,4-dimethylphenylimino)-3-methyl-4-[N-(3-chloro-4-methylphenyl)carbamoylmethyl]-4-thiazoline hydrochloride (R1=4-NO$_2$, R$_2$=2-CH$_3$, 4-CH$_3$, R$_3$=CH$_3$, HX=HCl).

Starting materials: methylisothiocyanate, 2,4-dimethylaniline, 4-chloro-3-oxo-N-(3-chloro-4-methylphenyl)butane amide Yield: 88% Melting point: 194–196° C. $^1$H NMR (DMSO-d$_6$+CDCl$_3$ =1:2) δ 2.23, 2.27 and 2.32 (3s, 9H, 3×ArCH$_3$), 3.81 (s, 3H, 3-CH$_3$), 4.06 (s, 2H, 4-CH$_2$), 7.01 (s, 1H, 5-vinyl H), 7.16~7.87 (m, 6H, ArH) 11.13 (s, 1H, NH); IR(KBr) 3$_3$ (NH), 1682 (C=C), 1578 (C=C) cm$^{-1}$.

[Compound 228]

2-(4-cyanophenylimino)-3-methyl-4-[N-(3-chloro-4-methylphenyl)carbamoylmethyl]-4-thiazoline hydrochloride (R1=3-Cl, 4-CH$_3$, R$_2$=4-CN, R$_3$=CH$_3$, HX=HCl).

Starting materials: methylisothiocyanate, 4-cyanoaniline, 4-chloro-3-oxo-N-(3-chloro-4-methylphenyl)butane amide Yield: 64% Melting point: 230~234° C. $^1$H NMR (DMSO-d$_6$) δ 2.43 (s, 3H, ArCH$_3$), 3.74 (s, 3H, 3-CH$_3$), 4.06 (s, 2H, 4-CH$_2$), 7.03 (s, 1H, 5-vinyl H), 7.18~7.97 (m, 7H, ArH), 10.87 (s, 1H, NH); IR(KBr) 3436 (NH), 1662 (C=O), 1602 (C=C) cm$^{-1}$.

[Compound 229]

2-(4-bromophenylimino)-3-methyl-4-[N-(3-chloro-4-methylphenyl)carbamoylmethyl]-4-thiazoline hydrochloride (R1=3-Cl, 4-CH$_3$, R$_2$=4-Br, R$_3$=CH$_3$, HX=HCl).

Starting materials: methylisothiocyanate, 4-bromoaniline, 4-chloro-3-oxo-N-(3-chloro-4-methylphenyl)butane amide Yield: 58% Melting point: 252~254° C. $^1$H NMR (DMSO-d$_6$) δ 2;27 (s, 3H, ArCH$_3$), 3.77 (s, 3H, 3-CH$_3$), 4.06 (s, 2H, 4-CH$_2$), 7.05 (s, 1H, 5-vinyl H), 7.27~7.85 (m, 7H, ArH), 10.99 (s, 1H, NH); IR(KBr) 3426 (NH), 1668 (C=O), 1604 (C=C) cm$^{-1}$.

[Compound 230]

2-(3,5-dichlorophenylimino)-3-methyl-4-[N-(3-chloro-4-methylphenyl)carbamoylmethyl]-4-thiazoline hydrochloride (R1=3-Cl, 4-CH$_3$, R$_2$=3-Cl, 5-Cl, R$_3$=CH$_3$, HX=HCl).

Starting materials: methylisothiocyanate, 3,5-dichloroaniline, 4-chloro-3-oxo-N-(3-chloro-4-methylphenyl)butane amide Yield: 63% Melting point: 216~221° C. $^1$H NMR (DMSO-d$_6$) δ 2.27 (s, 3H, ArCH$_3$) 3.69 (s, 3H, 3-CH$_3$), 4.02 (s, 2H, 4-CH$_2$), 6.94 (s, 1H, 5-vinyl H), 7.27~7.90 (m, 6H, ArH), 10.90 (s, 1H, NH); R(KBr) 3424 (NH), 1666 (C=O), 1598 (C=C) cm$^{-1}$.

[Compound 231]

2-(4-trifluoromethoxyphenylimino)-3-methyl-4-[N-(3-chloro-4-methylphenyl)carbamoylmethyl]-4-thiazoline hydrochloride (R1=3-Cl, 4-CH$_3$, R$_2$=4-OCF$_3$, R$_3$=CH$_3$, HX=HCl).

Starting materials: methylisothiocyanate, 4-trifluoromethoxyaniline, 4-chloro-3-oxo-N-(3-chloro-4-methylphenyl)butane amide Yield: 58% Melting point: 236~240° C. $^1$H NMR (DMSO-$d_6$) δ 2.27 (s, 3H, ArCH$_3$) 3.78 (s, 3H, 3-CH$_3$), 4.06 (s, 2H, 4-CH$_2$), 7.10 (s, 1H, 5-vinyl H), 7.28~7.85 (m, 7H, ArH), 10.95 (s, 1H, NH); IR(KBr) 3436 (NH), 1664 (C=O), 1606 (C=C) cm$^{-1}$.

[Compound 232]
2-(2.4-difluorophenylimino)-3-methyl-4-[N-(3-chloro-4-methylphenyl)carbamoylmethyl]-4-thiazoline hydrochloride (R1=3-Cl, 4-CH$_3$, R$_2$=2-F, 4-F, R$_3$=CH$_3$, HX=HCl).

Starting materials: methylisothiocyanate, 2.4-difluoroaniline, 4-chloro-3-oxo-N-(3-chloro-4-methylphenyl)butane amide Yield: 69% Melting point: 217~220° C. $^1$H NMR (DMSO-$d_6$) δ 2.27 (s, 3H, CH$_3$) 3.72 (s, 3H, 3-CH$_3$), 4.02 (s, 2H, 4-CH$_2$), 6.93 (s, 1H, 5-vinyl H), 7.23~7.84 (m, 6H, ArH), 10.94 (s, 1H, NH); IR(KBr) 3426 (NH), 1676 (C=O), 1582 (C=C) cm$^{-1}$.

[Compound 233]
2-(4-chlorophenylimino)-3-methyl-4-[N-(3-chloro-4-methylphenyl)carbamoylmethyl]-4-thiazoline hydrochloride (R1=3-Cl, 4-CH$_3$, R$_2$=4-Cl, R$_3$=CH$_3$, HX=HCl).

Starting materials: methylisothiocyanate, 4-chloroaniline, 4-chloro-3-oxo-N-(3-chloro-4-methylphenyl)butane amide Yield: 68% Melting point: 244~245° C. $^1$H NMR (DMSO-$d_6$) δ 2.27 (s, 3H, ArCH$_3$) 3.79 (s, 3H, 3-CH$_3$), 4.06 (s, 2H, 4-CH$_2$), 7.06 (s, 1H, 5-vinyl H), 7.27~7.84 (m, 7H, ArH), 11.01 (s, 1H, NH); IR(KBr) 3426 (NH), 1668 (C=O), 1604(C=C) cm$^{-1}$.

[Compound 234]
2-[4-(n-butyl)phenylimino]-3-methyl-4-(N-[3-chloro-4-methylphenyl)carbamoylmethyl]-4-thiazoline hydrochloride (R1=3-Cl, 4-CH$_3$, R$_2$=4-(CH$_2$)$_3$CH$_3$, R$_3$=CH$_3$, HX=HCl).

Starting materials: methylisothiocyanate, 4-(n-butyl)aniline, 4-chloro-3-oxo-N-(3-chloro-4-methylphenyl)butane amide Yield: 77% Melting point: 234~236° C. $^1$H NMR (DMSO-$d_6$) δ 0.90 (t, 3H, butyl CH$_3$), 1.27~1.34 (m, 2H$_1$, CH$_2$), 1.52~1.60 (m, 2H, CH$_2$), 2.27 (s, 3H, ArCH$_3$) 2.60~2.65 (m, 2H, CH$_2$), 3.78 (s, 3H, 3-CH$_3$), 4.06 (s, 2H, 4-CH$_2$), 7.04 (s, 1H, 5-vinyl H), 7.28~7.86 (m, 7H, ArH), 11.04 (s, 1H, NH); IR(KBr) 3426 (NH), 1664 (C=O), 1604 (C=C) cm$^{-1}$.

[Compound 235]
2-(2-fluorophenylimino)-3-methyl-4-[N-(3-chloro-4-methylphenyl)carbamoylmethyl]-4-thiazoline hydrochloride (R1=3-Cl, 4-CH$_3$, R$_2$=2-F, R$_3$=CH$_3$, HX=HCl).

Starting materials: methylisothiocyanate, 2-fluoroaniline, 4-chloro-3-oxo-N-(3-chloro-4-methylphenyl)butane amide Yield: 51% Melting point: 196~199° C. $^1$H NMR (DMSO-$d_6$) δ 2.25 (s, 3H, ArCH,) 3.74 (s, 3H, 3-CH$_3$), 4.03 (s, 2H, 4-CH$_2$), 6.96 (s, 1H, 5-vinyl H), 7.28~7.85 (m, 7H, ArH), 10.94 (s, 1H, NH); IR(KBr) 3426 (NH), 1678 (C=O), 1582 (C=C) cm$^{-1}$.

[Compound 236]
2-(3-fluorophenylimino)-3-methyl-4-[N-(3-chloro-4-methylphenyl)carbamoylmethyl]-1,3-thiazol-4-ine hydrochloride (R1=3-Cl, 4-CH$_3$, R$_2$=3-F, R$_3$=CH$_3$, HX=HCl).

Starting materials: methylisothiocyanate, 3-fluoroaniline, 4-chloro-3-oxo-N-(3-chloro-4-methylphenyl)butane amide Yield: 65% Melting point: 228° C. $^1$H NMR(DMSO-$d_6$) δ 2.28 (s, 3H, ArCH$_3$), 3.78 (s, 3H, 3-CH$_3$), 4.07 (s, 2H, 4-CH$_2$), 7.06 (s, 1H, 5-vinyl H), 7.22~7.85 (m, 7H, ArH), 10.97 (s, 1H, NH); IR(KBr) 3428(NH), 1671 (C=O), 1604 (C=C) cm$^{-1}$.

[Compound 237]
2-(4-fluorophenylimino)-3-methyl-4-[N-(3-chloro-4-methylphenyl)carbamoylmethyl]-1,3-thiazol-4-ine hydrochloride (R1=3-Cl, 4-CH$_3$, R$_2$=4-F, R$_3$=CH$_3$, HX=HCl).

Starting materials: methylisothiocyanate, 4-fluoroaniline, 4-chloro-3-oxo-N-(3-chloro-4-methylphenyl)butane amide Yield: 89% Melting point: 239~242° C. $^1$H NMR(DMSO-$d_6$) δ 2.27 (s, 3H, ArCH$_3$), 3.78 (s, 3H, 3-CH$_3$), 4.07 (s, 2H, 4-CH$_2$), 7.05 (s, 1H, 5-vinyl H), 7.28~7.86 (m, 7H, ArH), 11.02 (s, 1H, NH); IR(KBr) 3426(NH), 1668(C=O), 1582 (C=C) cm$^{-1}$.

[Compound 238]
2-(3-chloro-4-fluorophenylimino)-3-methyl-4-[N-(3-chloro-4-methylphenyl)carbamoylmethyl]-1,3-thiazol-4-ine hydrochloride (R1=3-Cl, 4-CH$_3$, R$_2$=3-Cl, 4-F, R$_3$=CH$_3$, HX=HCl).

Starting materials: methylisothiocyanate, 3-chloro-4-fluoroaniline, 4-chloro-3-oxo-N-(3-chloro-4-methylphenyl) butane amide Yield: 58% Melting point: 229~231° C. $^1$H NMR(DMSO-$d_6$) δ 2.27 (s, 3H, ArCH$_3$), 3.75(s, 3H, 3-CH$_3$), 4.05 (s, 2H, 4-CH$_2$), 7.01 (s, 1H, 5-vinyl H), 7.28~7.84 (m, 6H, ArH), 10.95 (s, 1H, NH); IR(KBr) 3426(NH), 1666(C=O), 1602 (C=C) cm$^{-1}$.

[Compound 239]
2-(2-methoxy-5-methylphenylimino)-3-methyl-4-[N-(3-chloro-4-methylphenyl)carbamoylmethyl]-1,3-thiazol-4-ine hydrochloride (R1=3-Cl, 4-CH$_3$, R$_2$=2-OCH$_3$, 5-CH$_3$, R$_3$=CH$_3$, HX=HCl).

Starting materials: methylisothiocyanate, 2-methoxy-5-methylaniline, 4-chloro-3-oxo-N-(3-chloro-4-methylphenyl)butane amide Yield: 40% Melting point: 190~195° C. $^1$H NMR(DMSO-$d_6$) δ 2.27 and 2.28 (2s, 6H, 2×ArCH$_3$), 3.76 (s, 3H, 3-CH$_3$), 3.81 (s, 3H, 2-OCH$_3$), 4.01 (s, 2H, 4-CH$_2$), 7.02 (s, 1H, 5-vinyl H), 7.17~7.86 (m, 6H, ArH), 11.05 (s, 1H, NH); IR(KBr) 3426(NH), 1650 (C=O), 1600(C=C) cm$^{-1}$.

[Compound 240]
3-methyl-2-(4-phenoxyphenylimino)-4-[N-(3-chloro-4-methylphenyl)carbamoylmethyl]-1,3-thiazol-4-ine hydrochloride (R1=3-Cl, 4-CH$_3$, R$_2$=4-OC$_6$H$_5$, R$_3$=CH$_3$, HX=HCl).

Starting materials: methylisothiocyanate, 4-phenoxyaniline, 4-chloro-3-oxo-N-(3-chloro-4-methylphenyl)butane amide Yield: 79% Melting point: 237~243° C. $^1$H NMR(DMSO-$d_6$) δ 2.27 (s, 3H, ArCH$_3$), 3.78 (s, 3H, 3-CH$_3$), 4.06 (s, 2H, 4-CH$_2$), 7.04 (s, 1H, 5-vinyl H), 7.08~7.86 (m, 12H, ArH), 11.01 (s, 1H, NH); IR(KBr) 3426(NH), 1666(C=O), 1604 (C=C) cm$^{-1}$.

[Compound 241]
2-(4-chloro-2-fluorophenylimino)-3-methyl-4-[N-(4-phenoxyphenyl)carbamoylmethyl]-1,3-thiazol-4-ine hydrochloride (R1=4-OC$_8$H$_5$, R$_2$=4-Cl, 2-F, R$_3$=CH$_3$, HX=HCl).

Starting materials: methylisothiocyanate, 4-chloro-2-fluoroaniline, 4-chloro-3-oxo-N-(4-phenoxyphenyl)butane amide Yield: 55% Melting point: 208–210° C. $^1$H NMR (DMSO-$d_6$) δ 3.63 (s, 3H, 3-CH$_3$), 3.99 (s, 2H, 4-CH$_2$), 6.76 (s, 1H, 5-vinyl H), 6.95~7.68 (m, 12H, ArH), 10.65 (s, 1H, NH); IR(KBr) 3443 (NH), 1664 (C=O), 1560 (C=C) cm$^{-1}$.

[Compound 242]
2-(4-fluorophenylimino)-3-methyl-4-[N-(4-phenoxyphenyl) carbamoylmethyl]-1,3-thiazol-4-ine hydrochloride (R1=4-OC$_6$H$_5$, R$_2$=4-F, R$_3$=CH$_3$, HX=HCl).

Starting materials: methylisothiocyanate, 4-fluoroaniline, 4-chloro-3-oxo-N-(4-phenoxyphenyl)butane amide Yield: 42% Melting point: 234–238° C. ¹H NMR (DMSO-d₆) δ 3.75 (s, 3H, 3-CH₃), 4.02 (s, 2H, 4-CH₂), 6.96 (s, 1H, 5-vinyl H), 6.96~7.67 (m, 13H, ArH), 10.71 (s, 1H, NH); IR(KBr) 3446 (NH), 1672 (C=O), 1580 (C=C) cm⁻¹.

[Compound 243]

2-(3-fluorophenylimino)-3-methyl-4-[N-(4-phenoxyphenyl)carbamoylmethyl]-1,3-thiazol-4-ine hydrochloride (R1=4-OC₆H₅, R₂=3-F, R₃=CH₃, HX=HCl).

Starting materials: methylisothiocyanate, 3-fluoroaniline, 4-chloro-3-oxo-N-(4-phenoxyphenyl)butane amide Yield: 49% Melting point: 214–217° C. ¹H NMR (DMSO-d₆) δ 3.79 (s, 3H, 3-CH₃), 3.05 (s, 2H, 4-CH₂), 6.95 (s, 1H, 5-vinyl H), 6.95~7.69 (m, 13H, ArH), 10.82 (s, 1H, NH); IR(KBr) 3448 (NH), 1686 (C=O), 1556 (C=C) cm⁻¹.

[Compound 244]

2-(2,4-difluorophenylimino)-3-methyl-4-[N-(4-phenoxyphenyl)carbamoylmethyl]-1,3-thiazol-4-ine hydrochloride (R1=4-OC₆H₅, R₂=2-F, 4-F, R₃=CH₃, HX=HCl).

Starting materials: methylisothiocyanate, 2,4-difluoroaniline, 4-chloro-3-oxo-N-(4-phenoxyphenyl)butane amide Yield: 43% Melting point: 202–205° C. ¹H NMR (DMSO-d₆) δ 3.75 (s, 3H, 3-CH₃), 4.01 (s, 2H, 4-CH₂), 6.95 (s, 1H, 5-vinyl H), 6.95~7.68 (m, 12H, ArH), 10.81 (s, 1H, NH); IR(KBr) 3422 (NH), 1664 (C=O), 1560 (C=C) cm⁻¹.

[Compound 245]

2-(2-fluorophenylimino)-3-methyl-4-[N-(4-phenoxyphenyl)carbamoylmethyl]-1,3-thiazol-4-ine hydrochloride (R1=4-OC₆H₅, R₂=2-F, R₃=CH₃, HX=HCl).

Starting materials: methylisothiocyanate, 2-fluoroaniline, 4-chloro-3-oxo-N-(4-phenoxyphenyl)butane amide Yield: 43% Melting point: 187–191° C. ¹H NMR (DMSO-d₆) δ 3.77 (s, 3H, 3-CH₃), 4.03 (s, 2H, 4-CH₂), 6.95 (s, 1H, 5-vinyl H), 6.92~7.68 (m, 13H, ArH), 10.82 (s, 1H, NH); IR(KBr) 3400 (NH), 1668 (C=O), 1560 (C=C) cm⁻¹.

[Compound 246]

2-(3-bromophenylimino)-3-methyl-4-[N-(4-phenoxyphenyl)carbamoylmethyl]-1,3-thiazol-4-ine hydrochloride (R1=4-OC₆H₅, R₂=3-Br, R₃=CH₃, HX=HCl), Starting materials: methylisothiocyanate, 3-bromoaniline, 4-chloro-3-oxo-N-(4-phenoxyphenyl)butane amide Yield: 40% Melting point: 196–201° C. ¹H NMR (DMSO-d₆) δ 3.79 (s, 3H, 3-CH₃), 4.05 (s, 2H, 4-CH₂), 6.95 (s, 1H, 5-vinyl H), 6.98~7.77 (m, 13H, ArH), 10.84 (s, 1H, NH); IR(KBr) 3444 (NH), 1671 (C=O), 1560 (C=C) cm⁻¹.

[Compound 247]

2-(3-chloro-4-fluorophenylimino)-3-methyl-4-[N-(4-phenoxyphenyl)carbamoylmethyl]-1,3-thiazol-4-ine hydrochloride (R1=4-OC₆H₅, R₂=3-Cl, 4-F, R₃=CH₃, HX=HCl).

Starting materials: methylisothiocyanate, 3-chloro-4-fluoroaniline, 4-chloro-3-oxo-N-(4-phenoxyphenyl)butane amide Yield: 37% Melting point: 221–225° C. ¹H NMR (DMSO-d₆) δ 3.95 (s, 3H, 3-CH₃), 4.03 (s, 2H, 4-CH₂), 6.95 (s, 1H, 5-vinyl H), 6.95~7.79 (m, 12H, ArH), 10.65 (s, 1H, NH); IR(KBr) 3448 (NH), 1672 (C=O), 1578 (C=C) cm⁻¹.

[Compound 248]

2-(3,5-dichlorophenylimino)-3-methyl-4-[N-(4-phenoxyphenyl)carbamoylmethyl]-1,3-thiazol-4-ine hydrochloride (R1=4-OC₈H₅, R₂=3-Cl, 5-Cl, R₃=CH₃, HX=HCl).

Starting materials: methylisothiocyanate, 3,5-dichloroaniline, 4-chloro-3-oxo-N-(4-phenoxyphenyl)butane amide Yield: 20% Melting point: 219–223° C. ¹H NMR (DMSO-d₆) δ 3.70 (s, 3H, 3-CH₃), 4.00 (s, 2H, 4-CH₂), 6.92 (s, 1H, 5-vinyl H), 6.95~7.67 (m, 12H, ArH), 10.72 (s, 1H, NH); IR(KBr) 3446 (NH), 1668 (C=O), 1560 (C=C) cm⁻¹.

[Compound 249]

2-(4-chlorophenylimino)-3-methyl-4-[N-(4-phenoxyphenyl)carbamoylmethyl]-1,3-thiazol-4-ine hydrochloride (R1=4-OC₆H₅, R₂=4-Cl, R₃=CH₃, HX=HCl).

Starting materials: methylisothiocyanate, 4-chloroaniline, 4-chloro-3-oxo-N-(4-phenoxyphenyl)butane amide Yield: 47% Melting point: 242–246° C. ¹H NMR (DMSO-d₆) δ 3.79 (s, 3H, 3-CH₃), 4.05 (s, 2H, 4-CH₂), 6.95 (s, 1H, 5-vinyl H), 6.97~7.69 (m, 13H, ArH), 10.89 (s, 1H, NH); IR(KBr) 3440 (NH), 1655 (C=O), 1559 (C=C) cm⁻¹.

[Compound 250]

2-[4-(n-butyl)phenylimino]-3-methyl-4-[N-(4-phenoxyphenyl)carbamoylmethyl]-1,3-thiazol-4-ine hydrochloride (R1=4-OC₆H₅, R₂=4-(CH₂)₃CH₃, R₃=CH₃, HX=HCl).

Starting materials: methylisothiocyanate, 4-(n-butyl)aniline, 4-chloro-3-oxo-N-(4-phenoxyphenyl)butane amide Yield: 66% Melting point: 231–235° C. ¹H NMR (DMSO-d₆) δ 0.90 (t, 3H, butyl CH₃), 1.27~1.95 (m, 2H, CH₂), 1.53~1.60 (m, 2H, CH₂), 2.59~2.65 (m, 2H, CH₂), 3.78 (s, 3H, 3-CH₃), 4.10 (s, 2H, 4-CH₂), 6.95 (s, 1H, 5-vinyl H), 6.97~7.68 (m, 13H, ArH), 10.80 (s, 1H, NH); IR(KBr) 3424 (NH), 1665 (C=O), 1560 (C=C) cm⁻¹.

[Compound 251]

2-(4-trifluoromethoxyphenylimino)-3-methyl-4-[N-(4-phenoxyphenyl)carbamoylmethyl]-1,3-thiazol-4-ine hydrochloride (R1=4-OC₆H₅, R₂=4-OCF₃, R₃=CH₃, HX=HCl).

Starting materials: methylisothiocyanate, 4-trifluoromethoxyaniline, 4-chloro-3-oxo-N-(4-phenoxyphenyl)butane amide Yield: 41% Melting point: 236–240° C. ¹H NMR (DMSO-d₆) δ 3.79 (s, 3H, 3-CH₃), 4.04 (s, 2H, 4-CH₂), 6.95 (s, 1H, 5-vinyl H), 6.98~7.68 (m, 13H, ArH), 10.81 (s, 1H, NH); IR(KBr) 3422 (NH), 1656 (C=O), 1560 (C=C) cm⁻¹.

[Compound 252]

2-(4-bromophenylimino)-3-methyl-4-[N-(4-phenoxyphenyl)carbamoylmethyl]-1,3-thiazol-4-ine hydrochloride (R1=4-OC₆H₅, R₂=4-Br, R₃=CH₃, HX=HCl).

Starting materials: methylisothiocyanate, 4-bromoaniline, 4-chloro-3-oxo-N-(4-phenoxyphenyl)butane amide Yield: 38% Melting point: 243–247° C. ¹H NMR (DMSO-d₆) δ 3.78 (s, 3H, 3-CH₃), 4.04 (s, 2H, 4-CH₂), 6.95 (s, 1H, 5-vinyl H), 6.98~7.80 (m, 13H, ArH), 10.80 (s, 1H, NH); IR(KBr) 3428 (NH), 1668 (C=O), 1598 (C=C) cm⁻¹.

[Compound 253]

2-(4-chloro-5-7isopropoxy-2-fluorophenylimino)-3-methyl-4-[N-(4-phenoxyphenyl)carbamoyl]-1,3-thiazol-4-ine hydrochloride (R1=4-OC₆H₅, R₂=4-Cl, 2-F, 5-OCH(CH₃)₂, R₃=CH₃, HX=HCl).

Starting materials: methylisothiocyanate, 4-chloro-5-isopropoxy-2-fluoroaniline, 4-chloro-3-oxo-N-(4-phenoxyphenyl)butane amide Yield: 25% Melting point: 211–217° C. ¹H NMR (DMSO-d₆) δ 1.29 (d, 6H, isopropoxy (CH₃)₂), 3.65 (s, 3H, 3-CH₃), 3.95 (s, 2H, 4-CH₂), 4.56~4.60 (m, 1H, CH), 6.80 (s, 1H, 5-vinyl H), 6.95~7.70 (m, 11H, ArH), 10.69 (s, 1H, NH); IR(KBr) 3430(NH), 1684 (C=O), 1560 (C=C) cm⁻¹.

[Compound 254]

2-(4-cyanophenylimino)-3-methyl-4-[N-(4-phenoxyphenyl)carbamoylmethyl]-1,3-thiazol-4-ine hydrochloride (R1=4-OC₈H₅, R₂=4-CN, R₃=CH₃, HX=HCl).

Starting materials: methylisothiocyanate, 4-cyanoaniline, 4-chloro-3-oxo-N-(4-phenoxyphenyl)butane amide Yield: 19% Melting point: 208–212° C. ¹H NMR (DMSO-d₆) δ 3.69 (s, 3H, 3-CH₃), 3.98 (s, 2H, 4-CH₂), 6.95

(s, 1H, 5-vinyl H), 6.90~7.92 (m, 13H, ArH), 10.66 (s, 1H, NH); IR(KBr) 3446 (NH), 1668 (C=O), 1550 (C=C) cm$^{-1}$.

[Compound 255]

2-(4-phenoxyphenylimino)-3-methyl-4-[N-(4-phenoxyphenyl)carbamoylmethyl]-1,3-thiazol-4-ine hydrochloride (R1=4-OC$_6$H$_5$, R$_2$=4-OC$_6$H$_5$, R$_3$=CH$_3$, HX=HCl).

Starting materials: methylisothiocyanate, 4-phenoxyaniline, 4-chloro-3-oxo-N-(4-phenoxyphenyl)butane amide Yield: 52% Melting point: 232–237° C. $^1$H NMR (DMSO-d$_6$) δ 3.79 (s, 3H, 3-CH$_3$), 4.04 (s, 2H, 4-CH$_2$), 6.95 (s, 1H, 5-vinyl H), 6.98~7.69 (m, 18H, ArH), 10.89 (s, 1H, NH); IR(KBr) 3448 (NH), 1654 (C=O), 1560 (C=C) cm$^{-1}$.

[Compound 256]

2-(4-trifluoromethylphenylimino)-3-methyl-4-[N-(4-phenoxyphenyl)carbamoylmethyl]-1,3-thiazol-4-ine hydrochloride (R1=4-OC$_8$H$_5$, R$_2$=4-CF$_3$, R$_3$=CH$_3$, HX=HCl).

Starting materials: methylisothiocyanate, 4-trifluoromethylaniline, 4-chloro-3-oxo-N-(4-phenoxyphenyl)butane amide Yield: 28% Melting point: 231–234° C. $^1$H NMR (DMSO-d$_6$) δ 3.63 (s, 3H, 3-CH$_3$), 3.99 (s, 2H, 4-CH$_2$), 6.95 (s, 1H, 5-vinyl H), 6.90~7.92 (m, 13H, ArH), 10.66 (s, 1H, NH); IR(KBr) 3446 (NH), 1668 (C=O), 1550 (C=C) cm$^{-1}$.

[Compound 257]

2-(4chloro-2-fluoro-5-isopropoxyphenylimino)-3-methyl-4-[N-(3-chloro-4-methylphenyl)carbamoylmethyl]-1,3-thiazol-4-ine hydrochloride (R1=3-Cl, 4-CH$_3$, R$_2$=4-Cl, 2-F, 5-OCH(CH$_3$)$_2$, R$_3$=CH$_3$, HX=HCl).

Starting materials: methylisothiocyanate, 4-chloro-2-fluoro-5-isopropoxyaniline, 4-chloro-3-oxo-N-(3-chloro-4-methylphenyl)butane amide Yield: 62% Melting point: 157~161° C. $^1$H NMR(DMSO-d$_6$) δ 1.28 (d, 6H, J=6.0 Hz, (CH$_3$)$_2$), 2.27 (s, 3H, ArCH$_3$), 3.63 (s, 3H, 3-CH$_3$), 3.97 (s, 2H, 4-CH$_2$), 4.54~4.62 (m, 1H, J=6.0 Hz, CH), 6.80 (s, 1H, 5-vinyl H), 7.28~7.84 (m, 5H, ArH), 10.84 (s, 1H, NH); IR(KBr), 3422(NH), 1582(C=O), 1536 (C=C) cm$^{-1}$.

[Compound 258]

2-(2,4-difluorophenylimino)-3-cyclopropyl-4-[N-(4-bromophenyl)carbamoylmethyl]-1,3-thiazol-4-ine hydrochloride (R1=4-Br, R$_2$=2-F, 4-F, R$_3$=cyclopropyl, HX=HCl).

Starting materials: cyclopropylisothiocyanate, 2,4-difluoroaniline, 4-chloro-3-oxo-N-(4-bromophenyl)butane amide Yield: 50% Melting point: 194–196° C. $^1$H NMR (DMSO-d$_6$) δ 1.17–1.89 (m, 4H, cyclopropyl CH$_2$), 2.48 (m 1H, cyclopropyl CH), 4.09 (s, 2H, 4-CH$_2$), 6.93 (s, 1H, 5-vinyl H), 7.06~7.87 (m, 7H, ArH), 10.90 (s, 1H, NH).

[Compound 259]

2-(4-phenoxyphenylimino)-3-cyclopropyl-4-[N-(4-bromophenyl)carbamoylmethyl]-1,3-thiazol-4-ine hydrochloride (R1=4-Br, R$_2$=4-OC$_6$H$_5$, R$_3$=cyclopropyl, HX=HCl).

Starting materials: cyclopropylisothiocyanate, 4-phenoxyaniline, 4-chloro-3-oxo-N-(4-bromophenyl)butane amide Yield: 74% Melting point: 199–215° C. (decomposition) $^1$H NMR (DMSO-d$_6$), δ 1.25–1.39 (m, 4H, Cyclopropyl (CH$_2$)$_2$), 2.50 (m 1H, Cyclopropyl CH), 4.08 (s, 2H, 4-CH$_2$), 6.95 (s, 1H, 5-vinyl H), 7.07~7.66 (m, 13H, ArH), 10.95 (s, 1H, NH); IR(KBr)3424 (NH), 1670(C=O), 1592 (C=C) cm$^{-1}$.

[Compound 260]

2-(4-cyanophenylimino)-3-cyclopropyl-4-[N-(4-bromophenyl)carbamoylmethyl]-1,3-thiazol-4-ine hydrochloride (R1=4-Br, R$_2$=4-CN, R$_3$=cyclopropyl, HX=HCl).

Starting materials: cyclopropylisothiocyanate, 4-cyanoaniline, 4-chloro-3-oxo-N-(4-bromophenyl)butane amide Yield: 13% Melting point: 231–245° C. $^1$H NMR (DMSO-d$_6$), δ 1.03–1.72 (m, 4H, Cyclopropyl (CH$_2$)$_2$), 1.35 (m 1H, Cyclopropyl CH), 4.08 (s, 2H, 4-CH$_2$), 6.89 (s, 1H, 5-vinyl H), 7.07~7.66 (m, 13H, ArH), 10.95 (s, 1H, NH); 3424 (NH), 1604 (C=O) cm$^{-1}$.

[Compound 261]

2-(3-fluorophenylimino)-3-cyclopropyl-4-[N-(4-bromophenyl)carbamoylmethyl]-1,3-thiazol-4-ine hydrochloride (R1=4-Br, R$_2$=3-F, R$_3$=cyclopropyl, HX=HCl).

Starting materials: cyclopropylisothiocyanate, 3-fluoroaniline, 4-chloro-3-oxo-N-(4-bromophenyl)butane amide Yield: 71% Melting point: 242–245° C. $^1$H NMR (DMSO-d$_6$), δ 1.12–1.31 (m, 4H, Cyclopropyl (CH$_2$)$_2$), 2.49–2.50 (m, 1H, Cyclopropyl CH), 4.11 (s, 2H, 4-CH$_2$), 7.01 (s, 1H, 5-vinyl H), 7.22~7.67 (m, 8H, ArH), 11.07 (s, 1H, NH); IR(KBr) 3424 (NH), 1672 (C=O), 1606 (C=C) cm$^{-1}$.

[Compound 262]

2-phenylimino-3-cyclopropyl-4-[N-(4-bromophenyl)carbamoylmethyl]-1,3-thiazol-4-ine hydrochloride (R1=4-Br, R$_2$=H, R$_3$=cyclopropyl, HX=HCl).

Starting materials: cyclopropylisothiocyanate, aniline, 4-chloro-3-oxo-N-(4-bromophenyl)butane amide Yield: 86% Melting point: 231–236° C. $^1$H NMR (DMSO-d$_6$), δ 1.20–1.32 (m, 4H, Cyclopropyl (CH$_2$)$_2$), 2.50 (m 1H, Cyclopropyl CH), 4.11 (s, 2H, 4-CH$_2$), 6.97 (s, 1H, 5-vinyl H), 7.41~7.67 (m, 9H, ArH), 11.09 (s, 1H, NH); IR(KBr) 3424 (NH), 1672 (C=O), 1602 (C=C) cm$^{-1}$.

[Compound 263]

2-(2,4-dimethylphenylimino)-3-cyclopropyl-4-[N-(4-bromophenyl)carbamoylmethyl]-1,3-thiazol-4-ine hydrochloride (R1=4-Br, R$_2$=2,4-(CH$_3$)$_2$, R$_3$=cyclopropyl, HX=HCl).

Starting materials: cyclopropylisothiocyanate, 2,4-dimethylaniline, 4-chloro-3-oxo-N-(4-bromophenyl)butane amide Yield: 76% Melting point: 218–221° C. $^1$H NMR (DMSO-d$_6$) δ 1.21–1.33 (m, 4H, Cyclopropyl (CH$_2$)$_2$), 2.23 and 2.33 (2s, 6H, 2,4-(CH$_3$)$_2$), 3.15–3.16 (m 1H, Cyclopropyl CH), 4.50 (s, 2H, 4-CH$_2$), 6.91 (s, 1H, 5-vinyl H), 7.17~7.68 (m, 7H, ArH), 11.2 (s, 1H, NH); IR(KBr), 1672 (C=O), 1589 (C=C) cm$^{-1}$.

[Compound 264]

2-(3-trifluoromethylphenylimino)-3-isopropyl-4-(N-phenylcarbamoylmethyl)-1,3-thiazol-4-ine hydrobromide (R1=H, R$_2$=3-CF$_3$, R$_3$=CH(CH$_3$)$_2$, HX=HBr).

Starting materials: isopropylisothiocyanate, 3-trifluoromethylaniline, 4-bromo-3-oxo-N-phenylbutane amide Yield: 20% Melting point: 136–142 $^1$H NMR (DMSO-d$_6$) δ 3.32 (s, 3H, 3-CH$_3$), 4.37 (s, 2H, 4-CH$_2$), 6.08 (s, 1H, 5-vinyl H), 7.07~7.80 (m, 9H, 2ArH), 10.20 (s, 1H, NH).

[Compound 269]

2-(2-methyl-4-chlorophenylimino)-3-methyl-4-(N-phenylcarbamoylmethyl)-1,3-thiazol-4-ine hydrobromide (R1=H, R$_2$=2-CH$_3$, 4-Cl, R$_3$=CH$_3$, HX=HBr).

Starting materials: methylisothiocyanate, 4-chloro-o-methylaniline, gamma-bromoacetoacetanilide Yield: 82% Melting point: 230–232° C. $^1$H NMR (60 MHz, CDCl$_3$+DMSO-d$_6$) δ 2.30 (s, 3H, CH$_3$), 4.00 (s, 3H, 3-CH$_3$), 4.13 (s, 2H, 4-CH$_2$), 7.13 (s, 1H, 5-vinyl CH), 7.10–7.94 (m, 8H, ArH), 10.12 (br. s, 1H, NH).

[Compound 270]
2-(2,4-dimethylphenylimino)-3-methyl-(N-phenylcarbamoylmethyl)-1,3-thiazol-4-ine hydrobromide (R1=H, R$_2$=2-CH$_3$, 4-CH$_3$, R$_3$=CH$_3$HX=HBr).

Starting materials: methylisothiocyanate, 2,4-dimethylaniline, gamma-bromoacetoaetanilide Yield: 91% Melting point: 182–184° C. $^1$H NMR (60 MHz, CDCl$_3$+DMSO-d$_6$) δ 2.20 and 2.28 (2s, 6H, (CH$_3$)$_2$, 4.20 (s, 3H, 3-CH$_3$), 4.22 (s, 2H, 4-CH$_2$), 7.07 (s, 1H, 5-vinyl CH) 7.27–8.11 (m, 4H, ArH and NH).

[Compound 271]
2-(3-cyanophenylimino)-3-methyl-4-(N-phenylcarbamoylmethyl)-1,3-thiazol-4-ine hydrobromide (R1=H, R$_2$=3-CN, R$_3$=CH$_3$, HX=HBr).

Starting materials: methylisothiocyanate, m-cyanoaniline, gamma-bromoacetoacetanilide Yield: 31% Melting point: 227° C. $^1$H NMR (60 MHz, CDCl$_3$+DMSO-d$_6$) δ 2.52 (s, 2H, 4-CH$_2$), 3.71 (s, 3H, 3-CH$_3$), 3.99 (s, 1H, 5-vinyl CH), 6.96–7.48 (m, 9H, 2ArH), 10.34 (br. s, 1H, NH).

[Compound 272]
2-(2,4-difluorophenylimino)-3-methyl-4-(N-(4-fluoro)-phenylcarbamoylmethyl)-1,3-thiazol-4-ine hydrobromide (R1=4-F, R$_2$=2-F, 4-F, R$_3$=CH$_3$, HX=HBr).

Starting materials: methylisothiocyanate, 2,4-difluoroaniline, 4-bromo-3-oxo-N-(4-fluorophenyl)butane amide Yield: 54% Melting point: 231–232° C. $^1$H NMR (60 MHz, CDCl$_3$+DMSO-d$_6$) δ 2.31 (s, 2H, 4-CH$_2$), 2.60 (s, 3H, 3-CH$_3$), 3.93 (s, 1H, 5-vinyl CH), 6.90–7.80 (m, 7H, 2ArH), 9.86 (br. s, 1H, NH).

[Compound 273]
2-(4-toluylimino)-3-methyl-4-(N-phenylcarbamoylmethyl)-1,3-thiazol-4-ine hydrobromide (R$_1$=H, R$_2$=4-CH$_3$, R$_3$=CH$_3$), HX=HBr).

Starting materials: methylisothiocyanate, 4-toluidine, gamma-bromoacetoacetanilide Yield: 68.4% Melting point: 247° C. $^1$H NMR (DMSO-d$_6$) δ 2.36 (s, 3H, Ar—CH$_3$), 3.71 (m, 3H, N—CH$_3$), 4.04 (s, 2H, CH$_2$), 7.04 (s, 5-vinyl CH), 7.06–7.63 (m, 9H, Ar—H), 10.44 (br. s, 1H, NH); IR(KBr) 3106 (NH), 1666 (C=O), 1602 (C=C) cm$^{-1}$.

[Compound 274]
2-(o-toluylimino)-3-methyl-4-(N-phenylcarbamoylmethyl)-1,3-thiazol-4-ine hydrobromide (R$_1$=H, R$_2$=2-CH$_3$, R$_3$=CH$_3$, HX=HBr).

Starting materials: methylisothiocyanate, o-toluidine, gamma-bromoacetoacetanilide Yield: 88.9% Melting point: 179–181° C. $^1$H NMR (DMSO-d$_6$) δ 2.28 (s, 3H, Ar—CH$_3$), 3.74 (s, 3H, 3-CH$_3$), 4.03 (s, 2H, 4-CH$_2$), 7.00 (s, 5-vinyl CH), 7.06–7.64 (m, 9H, Ar—H), 10.45 br. s, 1H, NH); IR(KBr) 3086(NH), 1676 (C=O), 1601(C=C) cm$^{-1}$.

[Compound 275]
2-(m-toluylimino)-3-methyl-4-(N-phenylcarbamoylmethyl)-1,3-thiazol-4-ine hydrobromide (R$_1$=H, R$_2$=3-CH$_3$, R$_3$=CH$_3$, HX=HBr).

Starting materials: methylisothiocyanate, m-toluidine, gamma-bromoacetoacetanilide Yield: 92.7% Melting point: 194–195° C. $^1$H NMR (DMSO-d$_6$) δ 2.37 (s, 3H, Ar—CH$_3$), 3.72 (s, 3H, 3-CH$_3$), 4.04 (s, 2H, 4-CH$_2$), 7.05 (s, 5-vinyl CH), 7.08–7.63 (m, 9H, Ar—H), 10.45 (br. s, 1H, NH); IR(KBr) 3289, 3136(NH), 1671(C=O), 1601(C=C) cm$^{-1}$.

[Compound 276]
2-(4-fluorophenylimino)-3-methyl-4-(N-phenylcarbamoylmethyl)-1,3-thiazol-4-ine hydrobromide (R1=H, R$_2$=4-F, R$_3$=CH$_3$, HX=HBr).

Starting materials: methylisothiocyanate, 4-fluoroaniline, gamma-bromoacetoacetanilide Yield: 93.8% Melting point: 238° C. $^1$H NMR (DMSO-d$_6$) δ 3.74 (s, 3H, 3-CH$_3$), 4.06 (s, 2H, 4-CH$_2$), 7.08 (s, 1H, 4-vinyl CH), 7.11–7.65 (m, 9H, Ar—H), 10.49 (br. s, 1H, NH); IR(KBr) 3236, 3136(NH), 1666(C=O), 1586(C=C) cm$^{-1}$.

[Compound 277]
2-(2-fluorophenylimino)-3-methyl-4-(N-phenylcarbamoylmethyl)-1,3-thiazol-4-ine hydrobromide (R1=H, R$_2$=2-F, R$_3$=CH$_3$HX=HBr).

Starting materials: methylisothiocyanate, o-fluoroaniline, gamma-bromoacetoacetanilide Yield: 95.9% Melting point: 192–194° C. $^1$H NMR (DMSO-d$_6$) δ 3.75 (s, 3H, 3-CH$_3$), 4.06 (s, 2H, 4-CH$_2$), 6.99 (s, 1H, 5-vinyl CH), 7.09–7.63 (m, 9H, Ar—H), 10.44 (br. s, 1H, NH); IR (KBr) 3136(NH), 1686(C=O), 1601(C=C) cm$^{-1}$.

[Compound 278]
2-(4-fluorophenylimino)-3-methyl-4-(N-phenylcarbamoylmethyl)-1,3-thiazol-4-ine hydrobromide (R1=H, R$_2$=3-F, R$_3$=CH$_3$, HX=HBr).

Starting materials: methylisothiocyanate, 4-fluoroaniline, gamma-bromoacetoacetanilide Yield: 94.7% Melting point: 215–216° C. $^1$H NMR (DMSO-d$_6$) δ 3.74 (s, 3H, 3-CH$_3$), 4.06 (s, 2H, 4-CH$_2$), 7.08 (s, 1H, 5-vinyl CH), 7.09–7.64 (m, 9H, Ar—H), 10.48 (br. s, 1H, NH); IR(KBr) 3109(NH), 1681(C=O), 1606(C=C) cm$^{-1}$.

[Compound 279]
2-(2-methoxyphenylimino)-3-methyl-4-(N-phenylcarbamoylmethyl)-1,3-thiazol-4-ine hydrobromide (R1=H, R$_2$=2-OCH$_3$ R$_3$=CH$_3$HX=HBr).

Starting materials: methylisothiocyanate, o-methoxyaniline, gamma-bromoacetoacetanilide Yield: 96.1% Melting point: 208–210° C. $^1$H NMR (DMSO-d$_6$) δ 3.73 (s, 3H, 3-CH$_3$), 3.86 (s, 3H, Ar—OCH$_3$), 4.04 (s, 2H, 4-CH$_2$), 7.04 (s, 1H, 5-vinyl CH), 7.06–7.64 (m, 9H, Ar—H), 10.46 (s, 1H, NH); IR(KBr) 3246, 3136(NH), 1681(C=O), 1626(C=C) cm$^{-1}$.

[Compound 280]
2-(4-methoxyphenylimino)-3-methyl-4-(N-phenylcarbamoylmethyl)-1,3-thiazol-4-ine hydrobromide (R$_1$=H, R$_2$=4-OCH$_3$, R$_3$=CH$_3$, HX=HBr).

Starting materials: methylisothiocyanate, 4-methoxyaniline, gamma-bromoacetoacetanilide Yield: 99% Melting point: 112° C. $^1$H NMR (DMSO-d$_6$) δ 3.61 (s, 3H, 3-CH$_3$), 3.78 (s, 3H, Ar—OCH$_3$), 4.02 (s, 2H, 4-CH$_2$), 7.07 (s, 1H, 5-vinyl CH), 7.09–7.76 (m, 9H, Ar—H), 10.23 (br. s, 1H, NH); IR(KBr) 3186, 3126(NH), 1686(C=O), 1606(C=C) cm$^{-1}$.

[Compound 281]
2-(2-phenylphenylimino)-3-methyl-4-(N-phenylcarbamoylmethyl)-1,3-thiazol-4-ine hydrobromide (R1=H, R$_2$=2-C$_6$H$_6$, R$_3$=CH$_3$HX=HBr).

Starting materials: methylisothiocyanate, o-phenylaniline, gamma-bromoacetoacetanilide Yield: 86% Melting point: 209–211° C. $^1$H NMR (DMSO-d$_6$) δ 3.61 (s, 3H, 3-CH$_3$), 3.95 (s, 2H, 4-CH$_2$), 6.90 (s, 1H, 5-vinyl CH), 7.07–7.61 (m, 14H, Ar—H), 10.42 (br. s, 1H, NH); IR(KBr) 3256, 3186(NH), 1705(C=O), 1596 (C=C) cm$^{-1}$.

[Compound 282]
2-(4-phenylphenylimino)-3-methyl-4-(N-phenylcarbamoylmethyl)-1,3-thiazol-4-ine hydrobromide (R1=H R$_2$=4-C$_6$H$_5$, R$_3$=CH$_3$, HX=HBr).

Starting materials: methylisothiocyanate, 4-phenylaniline, gamma-bromoacetoacetanilide Yield: 90.2% Melting point: 254° C. $^1$H NMR (DMSO-$d_6$) δ 3.77 (s, 3H, 3-CH$_3$), 4.07 (s, 2H, 4-CH$_2$), 7.09 (s, 1H, 5-vinyl CH), 7.11–7.88 (m, 14H, Ar—H), 10.47 (br. s, 1H, NH); IR(KBr) 3256, 3186(NH), 1676(C=O), 1606(C=C) cm$^{-1}$.

[Compound 283]

2-(4-chlorophenylimino)-3-methyl-4-(N-phenylcarbamoylmethyl)-1,3-thiazol-4-ine hydrobromide (R$_1$=H, R$_2$=4-Cl, R$_3$=CH$_3$, HX=HBr).

Starting materials: methylisothiocyanate, 4-chloroaniline, gamma-bromoacetoacetanilide Yield: 92.7% Melting point: 247° C. $^1$H NMR (DMSO-$d_6$) δ 3.72 (s, 3H, 3-CH$_3$), 4.04 (s, 2H, 4-CH$_2$), 7.06 (s, 1H, 4-vinyl CH), 7.08–7.63 (m, 9H, Ar—H), 10.45 (s, 1H, NH), IR(KBr) 3186, 3126(NH), 1681(C=O), 1606(C=C) cm$^{-1}$.

[Compound 284]

2-(3-chlorophenylimino)-3-methyl-4-(N-phenylcarbamoylmethyl)-1,3-thiazol-4-ine hydrobromide (R$_1$=H, R$_2$=3-Cl R$_3$=CH$_3$HX=HBr).

Starting materials: methylisothiocyanate, m-chloroaniline, gamma-bromoacetoacetanilide Yield: 92.7% Melting point: 210° C. $^1$H NMR (DMSO-$d_6$) δ 3.76 (s, 3H, 3-CH$_3$), 4.08 (s, 2H, 4-CH$_2$), 7.07 (s, 1H, 4-vinyl CH), 7.10–7.74 (m, 9H, Ar—H), 10.50 (br. s, 1H, NH); IR(KBr) 3247, 3186(NH), 1676(C=O), 1606(C=C) cm$^{-1}$.

[Compound 285]

2-(2-chlorophenylimino)-3-methyl-4-(N-phenylcarbamoylmethyl)-1,3-thiazol-4-ine hydrobromide (R1=H, R$_2$=2-Cl, R$_3$=CH$_3$, HX=HBr).

Starting materials: methylisothiocyanate, o-chloroaniline, gamma-bromoacetoacetanilide Yield: 89.3% Melting point: 188–190° C. $^1$H NMR (DMSO-$d_6$) δ 3.78 (s, 3H, 3-CH$_3$), 4.09 (s, 2H, 4-CH$_2$), 7.05 (s, 1H, 5-vinyl CH), 7.07–7.78 (m, 9H, Ar—H), 10.46 (br. s, 1H, NH); IR(KBr) 3136, 3106(NH), 1691(C=O), 1601 (C=C) cm$^{-1}$

[Compound 286]

2-(4-ethylphenylimino)-3-methyl-4-(N-phenylcarbamoylmethyl)-1,3-thiazol-4-ine hydrobromide (R1=H, R$_2$=4-CH$_2$CH$_3$, R$_3$=CH$_3$, HX=HBr).

Starting materials: methylisothiocyanate, 4-ethylaniline, gamma-bromoacetoacetanilide Yield: 99% Melting point: 119° C. (decomposition); $^1$H NMR (DMSO-$d_6$) δ 1.21 (t, 3H, CH$_3$), 2.65 (q, 2H, CH$_2$), 3.73 (s, 3H, 3-CH$_3$), 4.05 (s, 2H, 4-CH$_2$), 7.06 (s, 1H, 5-vinyl CH), 7.08–7.64 (m, 9H, Ar—H), 10.47 (br. s, 1H, NH); IR(KBr) 3176, 3116(NH), 1676(C=O), 1606(C=C) cm$^{-1}$.

[Compound 287]

2-(4-bromophenylimino)-3-methyl-4-(N-phenylcarbamoylmethyl)-1,3-thiazol-4-ine hydrobromide (R1=H, R$_2$=4-Br R$_3$=CH$_3$, HX=HBr).

Starting materials: methylisothiocyanate, 4-bromoaniline, gamma-bromoacetoacetanilide Yield: 98.7% Melting point: 225–227° C. (decomposition); $^1$H NMR (DMSO-$d_6$) δ 3.69 (s, 3H, 3-CH$_3$), 4.02 (s, 2H, 4-CH$_2$), 7.02 (s, 1H, 5-vinyl CH), 7.08–7.75 (m, 9H, Ar—H), 10.42 (br. s, 1H, NH); IR(KBr) 3186, 3124(NH), 1681(C=O), 1601(C=C) cm$^{-1}$.

[Compound 288]

2-(3-methylmercaptophenylimino)-3-methyl-4-(N-phenylcarbamoylmethyl)-1,3-thiazol-4-ine hydrobromide (R$_1$=H, R$_2$=3-SCH$_3$, R$_3$=CH$_3$, HX=HBr).

Starting materials: methylisothiocyanate, m-methylmercaptoaniline, gamma-bromoacetoacetanilide Yield: 93.2% Melting point: 119–200° C. (decomposition); $^1$H NMR (DMSO-$d_6$) δ 2.51 (s, 3H, S—CH$_3$), 3.73 (s, 3H, 3-CH$_3$), 4.05 (s, 2H, 4-CH$_2$) 7.06 (s, 1H, 5-vinyl CH), 7.08–7.64 (m, 9H, Ar—H), 10.46 (br. s, 1H, NH); IR(KBr) 3245, 3196(NH), 1676(C=O), 1601 (C=C) cm$^{-1}$.

[Compound 289]

2-(3-nitrophenylimino)-3-methyl-4-(N-phenylcarbamoylmethyl)-1,3-thiazol-4-ine hydrobromide (R$_1$=H, R$_2$=3-NO$_2$, R$_3$=CH$_3$, HX=HBr).

Starting materials: methylisothiocyanate, m-nitroaniline, gamma-bromoacetoacetanilide Yield: 94.6% Melting point: 232° C. $^1$H NMR (300 MHz) (DMSO-$d_6$) δ 2.48 (s, 3H, 3-CH$_3$), 3.92 (s, 2H, 4-CH$_2$) 6.76 (s, 1H, 5-vinyl CH), 7.03–8.13 (m, 9H, Ar—H), 10.31 (br. s, 1H, NH); IR(KBr) 3246, 3186(NH), 1686(C=O), 1601 (C=C) cm$^{-1}$.

[Compound 290]

2-(4-isopropoxyphenylimino)-3-methyl-4-(N-phenylcarbamoylmethyl)-1,3-thiazol-4-ine hydrobromide (R1=H R$_2$=4-OCH(CH$_3$)$_2$, R$_3$=CH$_3$, HX=HBr).

Starting materials: methylisothiocyanate, 4-isopropoxyaniline, gamma-bromoacetoacetanilide Yield: 99% Melting point: 119° C. (decomposition); $^1$H NMR (DMSO-$d_6$) δ 1.28 and 1.30 (2s, 6H, (CH$_3$)$_3$, 3.71 (s, 3H, 3-CH$_3$), 4.04 (s, 2H, 4-CH$_2$), 4.66 (m, 1H, isopropoxy-CH), 7.02 (s, 1H, 5-vinyl CH), 7.06–7.64 (m, 9H, Ar—H), 10.46 (br. s, 1H, NH); IR(KBr) 3186, 3126(NH), 1681 (C=O), 1631(C=C) cm$^{-1}$.

[Compound 291]

2-(3-isopropoxyphenylimino)-3-methyl-4-(N-phenylcarbamoylmethyl)-1,3-thiazol-4-ine hydrobromide (R1=H, R$_2$=3-OCH(CH$_3$)$_2$, R$_3$=CH$_3$, HX=HBr).

Starting materials: methylisothiocyanate, m-isopropoxyaniline, gamma-bromoacetoacetanilide Yield: 92.6% Melting point: 178–180° C. $^1$H NMR (DMSO-$d_6$) δ 1.28 and 1.30 (2s, 6H, (CH$_3$)$_3$), 3.75 (s, 3H, 3-CH$_3$), 4.07 (s, 2H, 4-CH$_2$), 4.62 (m, 1H, isopropoxy CH), 6.94 (s, 1H, 5-vinyl CH), 7.03–7.65 (m, 9H, Ar—H), 10.43 (br. s. 1H, NH); IR(KBr) 3186, 3066(NH), 1681(C=O), 1601(C=C) cm$^{-1}$.

[Compound 292]

2-(4-nitrophenylimino)-3-methyl-4-(N-phenylcarbamoylmethyl)-1,3-thiazol-4-ine hydrobromide (R1=H, R$_2$=4-NO$_2$, R$_3$=CH$_3$, HX=HBr).

Starting materials: methylisothiocyanate, 4-nitroaniline, gamma-bromoacetoacetanilide Yield: 41.87% Melting point: 156° C. $^1$H NMR (300 MHz) (DMSO-$d_6$) δ 2.45 (s, 3H, 3-CH$_3$), 3.88 (s, 2H, 4-CH$_2$) 6.79 (s, 1H, 5-vinyl CH), 7.07–8.34 (m, 9H, Ar—H), 10.21 (br. s, 1H, NH); IR (KBr) 3166(NH), 1676(C=O), 1623(C=C) cm$^{-1}$.

[Compound 293]

2-(4-(tert-butyl)phenylimino)-3-methyl-4-(N-phenylcarbamoylmethyl)-1,3-thiazol-4-ine hydrobromide (R1=H, R$_2$=4-(t-Bu), R$_3$=CH$_3$HX=HBr).

Starting materials: methylisothiocyanate, 4-(tert-butyl) aniline, gamma-bromoacetoacetanilide Yield: 88.3% Melting point: 232–234° C. $^1$H NMR (DMSO-$d_6$) δ 1.31 (s, 9H, tert-buthyl), 3.75 (s, 3H, 3-CH$_3$), 4.07 (s, 2H, 4-CH$_2$), 7.08 (s, 1H, 5-vinyl CH), 7.30–7.65 (m, 9H, Ar—H), 10.50 (br. s, 1H, NH); IR(KBr) 3187, 3126 (NH), 1681(C=O), 1596(C=C) cm$^{-1}$.

[Compound 294]

2-(o-(tert-butyl)phenylimino)-3-methyl-4-(N-phenylcarbamoylmethyl)-1,3-thiazol-4-ine hydrobromide (R1=H, R$_2$=2-(t-Bu), R$_3$=CH$_3$, HX=HBr).

Starting materials: methylisothiocyanate, o-(tert-butyl) aniline, gamma-bromoaetoacetanilide Yield: 95.7% Melting point: 239–241° C. $^1$H NMR (DMSO-d$_6$) δ 1.36 (s, 9H, (CH$_3$)$_3$, 3.89 (s, 3H, 3-CH$_3$), 4.11 (s, 2H, 4-CH$_2$), 7.01 (s, 1H, 5-vinyl CH), 7.06–7.72 (m, 9H, Ar—H), 10.16 (br. s, 1H, NH); IR(KBr) 3206, 3126(NH), 1686(C=O), 1601(C=C) cm$^{-1}$.

[Compound 295]

2-(o-isopropylphenylimino)-3-methyl-4-(N-phenylcarbamoylmethyl)-1,3-thiazol-4-ine hydrobromide (R1=H, R$_2$=2-CH(CH$_3$)$_2$, R$_3$=CH$_3$, HX=HBr).

Starting materials: methylisothiocyanate, o-isopropylaniline, gamma-bromoacetoacetanilide Yield: 90.3% Melting point: 214–215° C. $^1$H NMR (DMSO-d$_6$) δ 1.17 and 1.20 (2s, 6H, (CH$_3$)$_2$, 3.14 (m, 1H, isopropyl CH), 3.77 (s, 3H, 3-CH$_3$), 4.04 (s, 2H, 4-CH$_2$), 7.00 (s, 1H, 5-vinyl CH), 7.06–7.66 (m, 9H, Ar—H), 10.50 (br. s, 1H, NH); IR (KBr) 3227, 3186(NH), 1686(C=O), 1606(C=C) cm$^{-1}$.

[Compound 2961]

2-(m-isopropylphenylimino)-3-methyl-4-(N-phenylcarbamoylmethyl)-1,3-thiazol-4-ine hydrobromide (R1=H , R$_2$=3-CH(CH$_3$)$_2$, R$_3$=CH$_3$, HX=HBr).

Starting materials: methylisothiocyanate, m-isopropylaniline, gamma-bromoacetoacetanilide Yield: 90.8% Melting point: 213–215° C. $^1$H NMR (DMSO-d$_6$) δ 1.21 and 1.23 (2s, 6H, (CH$_3$)$_2$, 2.95 (m, 1H, isopropyl CH), 3.76 (s, 3H, 3-CH$_3$), 4.08 (s, 2H, 4-CH$_2$), 7.05 (s, 1H, 5-vinyl CH), 7.07–7.66 (m, 9H, Ar—H), 10.51 (br. s, 1H, NH); IR(KBr) 3246, 3196(NH), 1691(C=O), 1611(C=C) cm$^{-1}$.

[Compound 297]

2-(4-isopropylphenylimino)-3-methyl-4-(N-phenylcarbamoylmethyl)-1,3-thiazol-4-ine hydrobromide (R1=H , R$_2$=4-CH(CH$_3$)$_2$, R$_3$=CH$_3$, HX=HBr).

Starting materials: methylisothiocyanate, 4-isopropylaniline, gamma-bromoacetoacetanilide Yield: 93.2% Melting point: 241–242° C. $^1$H NMR (DMSO-d$_6$) δ 1.21 and 1.24 (2s, 6H, (CH$_3$)$_2$, 2.96 (m, 1H, CH), 3.75 (s, 3H, 3-CH$_3$), 4.06 (s, 2H, 4-CH$_2$), 7.07 (s, 1H, 5-vinyl CH), 7.08–7.65 (m, 9H, Ar—H), 10.49 (br. s, 1H, NH); IR(KBr) 3196, 3116(NH), 1676(C=O), 1591(C=C) cm$^{-1}$.

[Compound 298]

2-(4-(n-butyl)phenylimino)-3-methyl-4-(N-phenylcarbamoylmethyl)-1,3-thiazol-4-ine hydrobromide (R1=H, R$_2$=4-(n-Bu), R$_3$=CH$_3$, HX=HBr).

Starting materials: methylisothiocyanate, (4-(n-butyl) aniline, gamma-bromoacetoacetanilide Yield: 94.2% Melting point: 216–218° C. $^1$H NMR (DMSO-d$_6$) δ 0.90 (t, 3H, CH$_3$), 1.28–1.35 (m, 2H, CH$_2$), 1.55–1.63 (m, 2H, CH$_2$), 2.61–2.66 (m, 2H, CH$_2$) 3.74 (s, 3H, 3-CH$_3$), 4.05 (s, 2H, CH$_2$), 7.05 (s, 1H, 5-vinyl CH), 7.08–7.64 (m, 9H, Ar—H), 10.47 (br. s, 1H, NH); IR (KBr) 3196, 3136(NH), 1671(C=O), 1606(C=C) cm$^{-1}$.

[Compound 299]

2-(3-phenoxyphenylimino)-3-methyl-4-(N-phenylcarbamoylmethyl)-1,3-thiazol-4-ine hydrobromide (R1=H, R$_2$=3-OC$_6$H$_5$, R$_3$=CH$_3$, HX=HBr).

Starting materials: methylisothiocyanate, 3-phenoxyaniline, gamma-bromoacetoacetanilide Yield: 88.3% Melting point: 212–214° C. $^1$H NMR (DMSO-d$_6$) δ 3.71 (s, 3H, 3-CH$_3$), 4.05 (s, 2H, 4-CH$_2$), 7.04 (s, 1H, 5-vinyl CH), 7.06–7.64 (m, 14H, Ar—H), 10.47 (br. s, 1H, NH). IR (KBr) 3196, 3136(NH), 1671(C=O), 1606 (C=C) cm$^{-1}$.

[Compound 300]

2-(2-phenoxyphenylimino)-3-methyl-4-(N-phenylcarbamoylmethyl)-1,3-thiazol-4-ine hydrobromide (R1=H , R$_2$=2-OC$_6$H$_5$, R$_3$=CH$_3$, HX=HBr).

Starting materials: methylisothiocyanate, 2-phenoxyaniline, gamma-bromoacetoacetanilide Yield: 18.1% Melting point: 218° C. $^1$H NMR (DMSO-d$_6$) δ 3.72 (s, 3H, 3-CH$_3$), 4.04 (s, 2H, 4-CH$_2$), 7.06 (s, 1H, 5-vinyl CH), 7.08–7.63 (m, 14H, Ar—H), 10.45 (br. s, 1H, NH). IR(KBr) 3375(NH), 1626(C=O), 1576(C=C) cm$^{-1}$.

[Compound 301]

2-(3-cyanophenylimino)-3-methyl-4-(N-phenylcarbamoylmethyl)-1,3-thiazol-4-ine hydrobromide (R1=H, R$_2$=3-CN, R$_3$=CH$_3$, HX=HBr).

Starting materials: methylisothiocyanate, 3-cyanoaniline, gamma-bromoacetoacetanilide Yield: 88% Melting point: 237° C. $^1$H NMR (DMSO-d$_6$) δ 3.36 (s, 3H, 3-CH$_3$), 3.79 (s, 2H, 4-CH$_2$), 7.05 (s, 1H, 5-vinyl CH), 7.06–7.76 (m, 9H, Ar—H), 10.34 (br. s, 1H, NH). IR (KBr) 3246, 3196(NH), 1686(C=O), 1611(C=C) cm$^{-1}$.

[Compound 302]

2-(4-cyanophenylimino)-3-methyl-4-(N-phenylcarbamoylmethyl)-1,3-thiazol-4-ine hydrobromide (R1=H , R$_2$=4-CN. R$_3$=CH$_3$, HX=HBr).

Starting materials: methylisothiocyanate, 4-cyanoaniline, gamma-bromoacetoacetanilide Yield: 93.7% Melting point: 199–200° C. $^1$H NMR (DMSO-d$_6$) δ 3.38 (s, 3H, 3-CH$_3$), 3.77 (s, 2H, CH$_2$), 7.04 (s, 1H, 5-vinyl CH), 7.07–7.74 (m, 9H, Ar—H), 10.23 (br. s, 1H, NH). IR(KBr) 3335(NH), 1676(C=O), 1536(C=C) cm$^{-1}$.

[Compound 303]

2-(3-isopropoxyphenylimino)-3-methyl-4-[N-(4-chlorophenyl)carbamoylmethyl]-1,3-thiazol-4-ine hydrobromide (R1=4-Cl, R$_2$=3-OCH(CH$_3$)$_2$, R$_3$=CH$_3$, HX=HBr).

Starting materials: methylisothiocyanate, 3-isopropoxyaniline, 4-bromo-3-oxo-N-(4-chlorophenyl) butane amide Yield: 67% Melting point: 226° C. $^1$H NMR (CDCl$_3$+ DMSO-d$_6$) δ 1.26 (d, 3H, J=5.85 Hz, (CH$_3$)$_2$), 3.70 (s, 3H, 3-CH$_3$), 3.91 (s, 2H, 4-CH$_2$), 4.53 (m, 1H, J=5.85 Hz, isopropoxy CH), 6.91 (s, 1H, 5-vinyl CH), 6.78–7.47 (m, 8H, ArH), 10.09 (br. s, 1H, NH). IR(KBr) 3250(NH), 1670(C=O), 1512(C=C) cm$^{-1}$.

[Compound 304]

2-(4-ethylphenylimino)-3-methyl-4-[N-(4-chlorophenyl) carbamoylmethyl]-1,3-thiazol-4-ine hydrobromide (R1=4-Cl, R$_2$=4-CH$_2$CH$_3$, R$_3$=CH$_3$, HX=HBr).

Starting materials: methylisothiocyanate, 4-ethylaniline, 4-bromo-3-oxo-N-(4-chlorophenyl)butane amide Yield: 54% Melting point: 202° C. $^1$H NMR (CDCl$_3$+ DMSO-d$_6$) δ 1.21 (t, 3H, J=7.5 Hz, ethyl CH$_3$), 2.65 (q, 2H, J=7.5 Hz, ethyl CH$_2$), 3.69 (s, 3H, 3-CH$_3$), 3.95 (s, 2H, 4-CH$_2$), 7.00 (s, 1H, 5-vinyl CH), 6.82–7.50 (m, 8H, ArH), 10.20 (br. s, 1H, NH). IR(KBr) 3258(NH), 1670(C=O), 1570(C=C) cm$^{-1}$.

[Compound 305]

2-phenylimino-3-methyl-4-[N-(4-chlorophenyl) carbamoylmethyl]-1,3-thiazol-4-ine hydrobromide (R1=4-Cl, R$_2$=H, R$_3$=CH$_3$, HX=HBr).

Starting materials: methylisothiocyanate, aniline, 4-bromo-3-oxo-N-(4-chlorophenyl)butane amide Yield: 15% Melting point: 226° C. $^1$H NMR (CDCl$_3$+ DMDO-d$_6$) δ 3.70 (s, 3H, 3-CH$_3$), 3.92 (s, 2H, 4-CH$_2$), 6.98 (s, 1H, 5-vinyl ic CH), 6.78–7.49 (m, 9H, ArH), 10.14 (br. s, 1H NH); IR(KBr) 3264(NH), 1672(C=O), 1512(C=C) cm$^{-1}$.

[Compound 306]

2-phenylimino-3-methyl-4-[N-(4-methoxyphenyl) carbamoylmethyl]-1,3-thiazol-4-ine hydrobromide (R1=4-OCH$_3$, R$_2$=H R$_3$=CH$_3$, HX=HBr).

Starting materials: methylisothiocyanate, aniline, 4-bromo-3-oxo-N-(4-methoxyphenyl)butane amide Yield: 99% Melting point: 230° C. $^1$H NMR (CDCl$_3$+DMDO-d$_6$) δ 3.72(s, 3H, 3-CH$_3$), 3.95 (s, 2H, 4-CH$_2$), 7.02 (s, 1H, 5-vinyl CH), 7.26–7.61 (m, 9H, ArH), 10.45(br.s, 1H, NH); IR(KBr) 3180(NH), 1624 (C=O), 1540 (C=C) cm$^{-1}$.

[Compound 307]
2-(4-methoxyphenylimino)-3-methyl-4-[N-(4-methoxyphenyl)carbamoylmethyl]-1,3-thiazol-4-ine hydrobromide (R1=4-OCH$_3$, R$_2$=4-OCH$_3$, R$_3$=CH$_3$, HX=HBr).

Starting materials: methylisothiocyanate, 4-methoxyaniline, 4-bromo-3-oxo-N-(4-methoxyphenyl)butane amide Yield: 18% Melting point: 250° C. $^1$H NMR (CDCl$_3$+DMDO-d$_6$) δ 3.75 (s, 3H, 3-CH$_3$), 3.27 (s, 3H, OCH$_3$), 3.79(s, 3H, OCH$_3$), 3.98 (s, 2H, 4-CH$_2$), 6.98 (s, 1H, 5-vinyl CH), 7.01–7.62 (m, 8H, ArH), 10.48 (br.s, 1H, NH); IR(KBr) 3042 (NH), 1666 (C=O), 1594 (C=C) cm$^{-1}$.

[Compound 308]
2-(4-methoxyphenylimino)-3-methyl-4-[N-(4-chlorophenyl)carbamoylmethyl]-1,3-thiazol-4-ine hydrobromide (R1=4-Cl, R$_2$=4-OCH$_3$, R$_3$=CH$_3$, HX=HBr).

Starting materials: methylisothiocyanate, 4-methoxyaniline, 4-bromo-3-oxo-N-(4-methoxyphenyl)butane amide Yield: 87% Melting point: 240° C. $^1$H NMR (CDCl$_3$+DMDO-d$_6$) δ 3.70 (s, 3H, 3-CH$_3$), 3.76 (s, 3H, OCH$_3$), 3.91 (s, 2H, 4-CH$_2$), 6.94 (s, 1H, 5-vinyl CH), 6.76–7.48 (m, 8H, ArH), 10.16(br.s, 1H, NH); IR(KBr) 3248 (NH), 1664 (C=O), 1512 (C=C) cm$^{-1}$.

[Compound 309]
2-(4-methylphenylimino)-3-methyl-4-[N-(4-methoxyphenyl)carbamoylmethyl]-1,3-thiazol-4-ine hydrobromide (R1=4-OCH$_3$, R$_2$=4-CH$_3$, R$_3$=CH$_3$, HX=HBr).

Starting materials: methylisothiocyanate, 4-methylaniline, 4-bromo-3-oxo-N-(4-methoxyphenyl)butane amide Yield: 100% Melting point: 241° C. $^1$H NMR (CDCl$_3$+DMDO-d$_6$) δ 2.35 (s, 3H, 4-CH$_3$), 3.30 (s, 3H, 3-CH$_3$), 3.73 (s, 3H, 4-OCH$_3$), 3.96 (s, 2H, 4-CH$_2$), 6.98 (s, 1H, 5-vinyl CH), 7.21–7.59 (m, 8H, ArH), 10.12 (br.s, 1H, NH); IR(KBr) 3044 (NH), 1668 (C=O), 1578 (C=C) cm$^{-1}$.

[Compound 310]
2-(2-methylphenylimino)-3-methyl-4-[N-(4-chlorophenyl)carbamoylmethyl]1,3-thiazol-4-ine hydrobromide (R1=4-Cl, R$_2$=2-CH$_3$, R$_3$=CH$_3$, HX=HBr).

Starting materials: methylisothiocyanate, 2-methylaniline, 4-bromo-3-oxo-N-(4-methoxyphenyl)butane amide Yield: 33% Melting point: 217° C. $^1$H NMR (CDCl$_3$+DMDO-d$_6$) δ 2.25 (s, 3H, o-CH$_3$), 3.70 (s, 3H, 3-CH$_3$), 3.90(s, 2H, 4-CH$_2$), 6.91 (s, 1H, 5-vinyl CH), 6.76–7.47 (m, 8H, ArH), 10.12 (br.s, 1H, NH); IR(KBr) 3192 (NH), 1658 (C=O), 1512 (C=C) cm$^{-1}$.

[Compound 311]
2-(2-methoxyphenylimino)-3-methyl-4-[N-(4-methoxyphenyl)carbamoylmethyl]-1,3-thiazol-4-ine hydrobromide (R1=4-OCH$_3$, R$_2$=2-OCH$_3$, R$_3$=CH$_3$, HX=HBr).

Starting materials: methylisothiocyanate, 2-methoxyaniline, 4-bromo-3-oxo-N-(4-methoxyphenyl)butane amide Yield: 94% Melting point: 257° C. $^1$H NMR (CDCl$_3$+DMDO-d$_6$) δ 3.34 (s, 3H, 3-CH$_3$), 3.74 (s, 3H, OCH$_3$), 3.84 (s, 3H, OCH$_3$), 3.97 (s, 2H, 4-CH$_2$), 6.99 (s, 1H, 5-vinyl CH), 7.18–7.61 (m, 8H, ArH), 10.45(br.s,1H, NH); IR(KBr) 3180 (NH), 1686 (C=O), 1598 (C=C) cm$^{-1}$.

[Compound 312]
2-(2-methylphenylimino)-3-methyl-4-[N-(4-methoxyphenyl)carbamoylmethyl]-1,3-thiazol-4-ine hydrobromide (R1=4-OCH$_3$, R$_2$=2-CH$_3$, R$_3$=CH$_3$, HX=HBr).

Starting materials: methylisothiocyanate, 2-methylaniline, 4-bromo-3-oxo-N-(4-methoxyphenyl)butane amide Yield: 25% Melting point: 247° C. $^1$H NMR (CDCl$_3$+DMDO-d$_6$) δ 2.05 (s, 3H, o-CH$_3$), 2.95 (s, 3H, 3-CH$_3$), 3.35 (s, 3H, 4-OCH$_3$), 3.74 (s, 2H, 4-CH$_2$), 7.18 (s, 1H, 5-vinyl CH), 7.21–7.62 (m, 8H, ArH), 9.81 (br.s, 1H, NH); IR(KBr) 3174 (NH), 1660 (C=O), 1594 (C=C) cm$^{-1}$.

[Compound 313]
2-(4-isopropoxyphenylimino)-3-methyl-4-[N-(4-methoxyphenyl)carbamoylmethyl]-1,3-thiazol-4-ine hydrobromide (R1=4-OCH$_3$, R$_2$=4-OCH(CH$_3$)$_2$, R$_3$=CH$_3$, HX=HBr).

Starting materials: methylisothiocyanate, 4-isopropoxyaniline, 4-bromo-3-oxo-N-(4-methoxyphenyl)butane amide Yield: 90% Melting point: 247° C. $^1$H NMR (CDCl$_3$+DMDO-d$_6$) δ 1.29 (d, 6H, J=6.00 Hz, (CH$_3$)$_2$), 3.74 (s, 3H, 3-CH$_3$), 3.98 (s, 2H, 4-CH$_2$), 4.57 (m, 1H, J=6.00 Hz, CH), 6.98 (s, 1H, 5-vinyl CH), 6.95–7.61 (m, 8H, ArH), 10.48 (br.s, 1H, NH); IR(KBr) 3182 (NH), 1684(C=O), 1628 (C=C) cm$^{-1}$.

[Compound 314]
2-(4-isopropoxyphenylimino)-3-methyl-4-[N-(4-chlorophenyl)carbamoylmethyl]-1,3-thiazol-4-ine hydrobromide (R1=4-Cl, R$_2$=4-OCH(CH$_3$)$_2$, R$_3$=CH$_3$, HX=HBr).

Starting materials: methylisothiocyanate, 4-isopropoxyaniline, 4-bromo-3-oxo-N-(4-chlorophenyl)butane amide Yield: 23% Melting point: 229° C. $^1$H NMR (CDCl$_3$+DMDO-d$_6$) δ 1.29(d, 6H, J=5.5 Hz, (CH$_3$)$_2$), 3.70 (s, 3H, 3-CH$_3$), 3.90 (s, 2H, 4-CH$_2$), 4.58 (m, 1H, J=5.5 Hz, CH), 6.95 (s, 1H, 5-vinyl CH), 6.78–7.48 (m, 8H, ArH), 10.13 (br.s, 1H, NH); IR(KBr) 3060 (NH), 1666 (C=O), 1510 (C=C) cm$^{-1}$.

[Compound 315]
2-(4-fluorophenylimino)-3-methyl-4-[N-(4-methoxyphenyl)carbamoylmethyl]-1,3-thiazol-4-ine hydrobromide (R1=4-OCH$_3$, R$_2$=4-F, R$_3$=CH$_3$, HX=HBr).

Starting materials: methylisothiocyanate, 4-fluoroaniline, 4-bromo-3-oxo-N-(4-methoxyphenyl)butane amide Yield: 35% Melting point: 240° C. $^1$H NMR (CDCl$_3$+DMDO-d$_6$) δ 3.35 (s, 3H, 3-CH$_3$), 3.70 (s, 3H, 4-OCH$_3$), 3.97 (s, 2H, 4-CH$_2$), 6.99 (s, 1H, 5-vinyl CH), 7.25–7.60 (m, 8H, ArH), 10.12 (br.s, 1H, NH); IR(KBr) 3424 (NH), 1670 (C=O), 1508 (C=C) cm$^{-1}$.

[Compound 316]
2-(4-fluorophenylimino)-3-methyl-4-[N-(4-chlorophenyl)carbamoylmethyl]-1,3-thiazol-4-ine hydrobromide (R1=4-Cl, R$_2$=4-F, R$_3$=CH$_3$, HX=HBr).

Starting materials: methylisothiocyanate, 4-fluoroaniline, 4-bromo-3-oxo-N-(4-chlorophenyl)butane amide Yield: 91% Melting point: 234° C. $^1$H NMR (CDCl$_3$+DMDO-d$_6$) δ 3.71 (s, 3H, 3-CH$_3$), 3.93 (s, 2H, 4-CH$_2$), 6.98 (s, 1H, 5-vinyl CH), 6.81–7.51 (m, 8H, ArH), 10.17 (br.s, 1H, NH); IR(KBr) 3120 (NH), 1666 (C=O), 1512 (C=C) cm$^{-1}$.

[Compound 317]
2-(4-bromophenylimino)-3-methyl-4-[N-(4-chlorophenyl)carbamoylmethyl]-1,3-thiazol-4-ine hydrobromide (R1=4-Cl, R$_2$=4-Br, R$_3$=CH$_3$HX=HBr).

Starting materials: methylisothiocyanate, 4-bromoaniline, 4-bromo-3-oxo-N-(4-chlorophenyl)butane amide Yield: 74% Melting point: 229° C. $^1$H NMR (CDCl$_3$+DMDO-d$_6$) δ 3.71 (s, 3H, 3-CH$_3$), 3.73 (s, 3H, OCH$_3$), 3.96 (s, 2H, 4-CH$_2$), 7.05 (s, 1H, 5-vinyl CH), 6.82–7.69 (m, 8H, ArH), 10.22 (br.s, 1H, NH); IR(KBr) 3060 (NH), 1656 (C=O), 1510 (C=C) cm$^{-1}$.

[Compound 318]
2-(4-bromophenylimino)-3-methyl-4-[N-(4-methoxyphenyl)carbamoylmethyl]-1,3-thiazol-4-ine hydrobromide (R1=4-OCH$_3$, R$_2$=4-Br, R$_3$=CH$_3$, HX=HBr).

Starting materials: methylisothiocyanate, 4-bromoaniline, 4-bromo-3-oxo-N-(4-methoxyphenyl)butane amide Yield: 92% Melting point: 230° C. $^1$H NMR (CDCl$_3$+DMDO-d$_6$) δ 3.71 (s, 3H, 3-CH$_3$), 3.73 (s, 3H, OCH$_3$), 3.96 (s, 2H, 4-CH$_2$), 7.05 (s, 1H, 5-vinyl CH), 6.82–7.69 (m, 8H, ArH), 10.12 (br.s, 1H, NH); IR(KBr) 3060 (NH), 1656 (C=O), 1510 (C=C) cm$^{-1}$.

[Compound 319]
2-(4-phenoxyphenylimino)-3-methyl-4-[N-(4-chlorophenyl)carbamoylmethyl]-1,3-thiazol-4-ine hydrobromide (R1=4-Cl, R$_2$=4-OC6H$_5$, R$_3$=CH$_3$, HX=HBr).

Starting materials: methylisothiocyanate, 4-phenoxyaniline, 4-bromo-3-oxo-N-(4-chlorophenyl) butane amide Yield: 89% Melting point: 229° C. $^1$H NMR (CDCl$_3$+DMDO-d$_6$) δ 3.71 (s, 3H, 3-CH$_3$), 3.94 (s, 2H, 4-CH$_2$), 7.01 (s, 1H, 5-vinyl CH), 6.80–7.50 (m, 13H, ArH), 10.19 (br.s, 1H, NH); IR(KBr) 3180 (NH), 1670 (CO), 1510 (C=C) cm$^{-1}$.

[Compound 320]
2-(4-phenoxyphenylimino)-3-methyl-4-[N-(4-methoxyphenyl)carbamoylmethyl]-1,3-thiazol-4-ine hydrobromide (R1+4-OCH$_3$, R$_2$=4-OC$_8$H$_5$, R$_3$=CH$_3$, HX=HBr).

Starting materials: methylisothiocyanate, 4-phenoxyaniline, 4-bromo-3-oxo-N-(4-methoxyphenyl) butane amide Yield: 90% Melting point: 228° C. $^1$H NMR (CDCl$_3$+DMDO-d$_6$) δ 3.71 (s, 3H, 3-CH$_3$), 3.76 (s, 3H, OCH$_3$), 3.97 (s, 2H, 4-CH$_2$), 7.04 (s, 1H, 5-vinyl CH), 6.81–7.52 (m, 13H, ArH), 10.24 (br.s, 1H, NH); IR(KBr) 3064 (NH), 1658 (C=O), 1510 (C=C) cm$^{-1}$.

[Compound 321]
2-(2,4,6-trimethylphenylimino)-3-methyl-4-N-phenylcarbamoyl methyl-1,3-thiazol-4-ine hydrobromide (R1=H, R$_2$=2,4,6-tri Me, R$_3$=CH$_3$, HX=HBr).

Starting materials: methylisothiocyanate, 2,4,6-trimethylaniline, 4-bromoacetoacetanilide Yield: 93% Melting point: 243° C. $^1$H NMR (CDCl$_3$+DMDO-d$_6$) δ 2.17 (s, 9H, (CH$_3$)$_3$), 3.80 (s, 3H, 3-CH$_3$), 3.98 (s, 2H, 4-CH$_2$), 6.96 (s, 1H, 5-vinyl CH), 7.01–7.59 (m, 7H, ArH), 10.34 (br.s, 1H, NH); IR(KBr) 3032 (NH), 1692 (C=O), 1582 (C=C) cm$^{-1}$.

[Compound 322]
2-(4-cyanophenylimino)-3-methyl-4-[N-(4-chlorophenyl)carbamoylmethyl]-1,3-thiazol-4-ine hydrobromide (R1+4-Cl, R$_2$=4-CN, R$_3$=CH$_3$, HX=HBr).

Starting materials: methylisothiocyanate, 4-cyanoaniline, 4-bromo-3-oxo-N-(4-chlorophenyl)butane amide Yield: 80% Melting point: 241° C. $^1$H NMR (CDCl$_3$+DMDO-d$_6$) δ 3.65 (s, 3H, 3-CH$_3$), 3.92 (s, 2H, 4-CH$_2$), 6.84 (s, 1H, 5-vinyl CH), 7.24–7.80 (m, 8H, ArH), 10.40 (br.s, 1H, NH); IR(KBr) 3048 (NH), 1694 (C=O), 1542 (C=C) cm$^{-1}$.

[Compound 323]
2-(4-cyanophenylimino)-3-methyl-4-[N-(4-methoxyphenyl)carbamoylmethyl]-1,3-thiazol-4-ine hydrobromide (R1+4-OCH$_3$, R$_2$=4-CN, R$_3$=CH$_3$, HX=HBr).

Starting materials: methylisothiocyanate, 4-cyanoaniline, 4-bromo-3-oxo-N-(4-methoxyphenyl)butane amide Yield: 88% Melting point: 213–215° C. $^1$H NMR (CDCl$_3$+DMDO-d$_6$) δ 3.70 (s, 3H, 3-CH$_3$), 3.74 (s, 3H, OCH$_3$), 3.92 (s, 2H, 4-CH$_2$), 6.97 (s, 1H, 5-vinyl CH), 6.77–7.80 (m, 8H, ArH), 10.14 (br.s, 1H, NH); IR(KBr) 3448 (NH), 1658 (C=O), 1558 (C=C) cm$^{-1}$.

[Compound 324]
2-(4-cyanophenylimino)-3-methyl-4-[N-(2-methylphenyl)carbamoylmethyl]1,3-thiazol-4-ine hydrobromide (R1=2-CH$_3$, R$_2$=4-CN, R$_3$=CH$_3$, HX=HBr).

Starting materials: methylisothiocyanate, 4-cyanoaniline, 4-bromo-3-oxo-N-(2-methylphenyl)butane amide Yield: 72% Melting point: 127° C. $^1$H NMR (CDCl$_3$+DMDO-d$_6$) δ 2.21 (s, 3H, o-CH$_3$), 3.66 (s, 3H, N—CH$_3$), 3.90 (s, 2H, 4-CH$_2$), 6.76 (s, 1H, 5-vinyl CH), 6.99–7.74 (m, 8H, ArH), 9.59 (br.s, 1H, NH); IR(KBr) 3536(NH), 1658 (C=O), 1558(C=C) cm$^{-1}$.

[Compound 325]
2-(3,4-dichlorophenylimino)-3-methyl-4-N-phenylcarbamoylmethyl-1,3-thiazol-4-ine hydrobromide (R1=H, R$_2$=3,4-di Cl, R$_3$=CH$_3$, HX=HBr).

Starting materials: methylisothiocyanate, 3,4-dichloroaniline, 4-bromoacetoacetanilide Yield: 87% Melting point: 248° C. $^1$H NMR (CDCl$_3$+DMDO-d$_6$) δ 3.65 (s, 3H, 3-CH$_3$), 3.91 (s, 2H, 4-CH$_2$), 6.85 (s, 1H, 5-vinyl CH), 6.99–7.57 (m, 8H, ArH), 10.40 (br.s, 1H, NH); IR(KBr) 3448 (NH), 1658 (C=O), 1572 (C=C) cm$^{-1}$.

[Compound 326]
2-(4-butyl(t-)phenylimino)-3-methyl-4-[N-(4-methoxyphenyl)carbamoylmethyl]-1,3-thiazol-4-ine hydrobromide (R1=4-OCH$_3$, R$_2$=4-(t-Bu), R$_3$=CH$_3$, HX=HBr).

Starting materials: methylisothiocyanate, 4-butyl(t-)aniline, 4-bromo-3-oxo-N-(4-methoxyphenyl)butane amide Yield: 83% Melting point: 210° C. $^1$H NMR (CDCl$_3$+DMDO-d$_6$) δ 1.22 (s, 9H, (CH$_3$)$_3$), 3.68 (s, 3H, 3-CH$_3$), 3.93 (s, 2H, 4-CH$_2$), 7.10 (s, 1H, 5-vinyl CH), 6.70–7.53 (m. 8H, ArH), 10.17 (br.s, 1H, NH); IR(KBr) 3450 (NH), 1666 (C=O), 1564 (C=C) cm$^{-1}$.

[Compound 327]
2-(4-butyl(t-)phenylimino)-3-methyl-4-[N-(2-methoxyphenyl)carbamoylmethyl]-1,3-thiazol-4-ine hydrobromide (R1+2-OCH$_3$, R$_2$=4-(t-Bu) R$_3$=CH$_3$, HX=HBr).

Starting materials: methylisothiocyanate, 4-butyl(t-)aniline, 4-bromo-3-oxo-N-(2-methoxyphenyl)butane amide Yield: 65% Melting point: 212° C. $^1$H NMR (CDCl$_3$+DMDO-d$_6$) δ 1.30 (s, 9H, t-Bu), 1.98 (s, 3H, o-CH$_3$), 3.26 (s, 3H, 3-CH$_3$), 3.56 (s, 2H, 4-CH$_2$), 7.12 (s, 1H, 5-vinyl CH), 7.00–7.62 (m, 8H, ArH), 9.10 (br.s, 1H, NH); IR(KBr) 3426(NH), 1688(C=O), 1630(C=C) cm$^{-1}$.

[Compound 328]
2-(3-methylphenylimino)-3-methyl-4-[N-(4-methoxyphenyl)carbamoylmethyl]-1,3-thiazol-4-ine hydrobromide (R1+4-OCH$_3$, R$_2$=3-CH$_3$, R$_3$=CH$_3$, HX=HBr).

Starting materials; methylisothiocyanate, 3-methylaniline, 4-bromo-3-oxo-N-(4-methoxyphenyl) butane amide Yield: 20% Melting point: 214° C. $^1$H NMR (CDCl$_3$+DMDO-d$_6$) δ 2.35 (s, 3H, m-CH$_3$), 3.70 (s, 3H, 3-CH$_3$), 3.72 (s, 3H, 4-OCH$_3$), 3.90 (s, 2H, 4-CH$_2$), 6.96 (s, 1H, 5-vinyl CH), 6.78–7.47 (m, 8H, ArH), 8.06 (br.s, 1H, NH). IR(KBr) 3448 (NH), 1672 (C=O), 1574 (C=C) cm$^{-1}$.

Elimination of hydrogen chloride or hydrogen bromide from 2-phenyliminothiazoline hydrogen chloride or hydrobromide: General experimental method After adding 2-(4-cyanophenylimino)-3-methyl-4-[N-(4-chlorophenyl) carbamoylmethyl]-1,3-thiazol-4-ine chloride (50.8 mg, 0.121 mmol) in sodium hydroxide (50.8 mg, 0.145 mmol)solubilized in methanol (12 mL) and reacted for 20 min, the product was filtered. The excess solvent was removed by evaporating at a reduced pressure. The product was dissolved again in dichloromethane and washed once with cold water. The organic layer was dried with anhydrous magnesium sulfate, filtered and evaporated under reduced pressure to obtain white powder (29.6 mg).

[Compound 329]
2-(4-cyanophenylimino)-3-methyl-4-[N-(4-chlorophenyl) carbamoylmethyl]-1,3-thiazol-4-ine($R_1$=4-Cl, $R_2$=4-CN, $R_3$=$CH_3$).
Yield: 64% Melting point: 210–212° C. $^1$H NMR (CDCl$_3$) δ 4.19 (s, 3H, 3-CH$_3$), 4.25 (s, 2H, 4-CH$_2$), 6.84 (s, 1H, 5-vinyl H), 7.21~7.74 (m, 8H, ArH).

[Compound 330]
2-(4-cyanophenylimino)-3-methyl-4-[N-(4-methoxyphenyl) carbamoylmethyl]-1,3-thiazol-4-ine ($R_1$=4-CH$_3$, $R_2$=4-CN, $R_3$=CH$_3$).
Yield: 72% Melting point: 225–226° C. $^1$H NMR (CDCl$_3$) δ 3.70 (s, 3H, 4-OCH$_3$), 4.00 (s, 3H, 3-CH$_3$), 4.06 (s, 2H, 4-CH$_2$), 6.63 (s, 1H, 5-vinyl H), 6.72~7.66 (m, 8H, ArH).

[Compound 331]
2-(2,4-difluorophenylimino)-3-methyl-4-[N-phenylcarbamoylmethyl]-1,3-thiazol-4-ine($R_1$=H, $R_2$=2,4-F$_2$, $R_3$=CH$_3$).
Yield: 71% Melting point: 214–215° C. $^1$H NMR (CDCl$_3$) δ 3.69 (s, 3H, 3-CH$_3$), 3.76 (s, 2H, 4-CH$_2$), 6.18 (s, 1H, 5-vinyl H), 6.79~7.56 (m, 8H, ArH), 11.05 (s, 1H, NH).

[Compound 332]
2-(2,4-difluorophenylimino)-3-methyl-4-[N-(4-methylphenyl)carbamoylmethyl]-1,3-thiazol-4-ine ($R_1$=4-CH$_3$, $R_2$=2,4-F$_2$, $R_3$=CH$_3$).
Yield: 59% Melting point: 183–184° C. $^1$H NMR (CDCl$_3$) δ 2.24 (s, 3H, 4-CH$_3$), 3.70 (s, 3H, 3-CH$_3$), 3.76 (s, 2H, 4-CH$_2$), 6.20 (s, 1H, 5-vinyl H), 6.79~7.50 (m, 8H, ArH), 10.93 (s, 1H, NH).

[Compound 333]
2-(2-fluoro-4-chloro-5-isopropoxyphenylimino)-3-methyl-4-[N-(3-methylphenyl)carbamoylmethyl]-1,3-thiazol-4-ine ($R_1$=H, $R_2$=2-F, 4-Cl, 5-OCH(CH$_3$)$_2$, $R_3$=CH$_3$).
Yield: 63% Melting point: 172–173° C. $^1$H NMR (CDCl$_3$) δ 1.37~1.39 (2s, 6H, (CH$_3$)$_2$), 4.33~4.53 (m, 1H, 4-OCH(CH$_3$)$_2$), 6.60 (s, 1H, 5-vinyl H), 7.04~7.62 (m, 6H, ArH), 9.80 (s, 1H, NH).

[Compound 334]
2-[4-(n-butyl)phenylimino]-3-methyl-4-[N-(4-methoxyphenyl)carbamoylmethyl]-1,3-thiazol-4-ine ($R_1$=4-OCH$_3$, $R_2$=(CH$_2$)$_3$CH$_3$, $R_3$=CH$_3$).
Yield: 67% Melting point: 141–142° C. $^1$H NMR (CDCl$_3$) δ 0.92~0.97 (m, 3H, butyl CH$_3$), 1.33~1.41 (m, 2H, CH2), 1.55~1.63 (m, 2H, CH2), 2.58~2.68 (m, 2H, CH2), 3.79 (s, 3H, 3-CH$_3$), 4.28 (s, 2H, 4-CH$_2$), 6.26 (s, 1H, 5-vinyl H), 6.77~7.67 (m, 8H, ArH).

[Compound 335]
2-(3-bromophenylimino)-3-methyl-4-[N-(methoxyphenyl) carbamoylmethyl]-1,3-thiazol-4-ine($R_1$=4-OCH$_3$, $R_2$=3-Br, $R_3$=CH$_3$).
Yield: 70% Melting point: 173–174° C. $^1$H NMR (CDCl$_3$) δ 3.79 (s, 3H, 3-CH$_3$), 3.90 (s, 3H, 4-OCH$_3$), 4.31 (s, 2H, 4-CH$_2$), 6.42 (s, 1H, 5-vinyl H), 7.67~7.71 (m, 7H, ArH), 10.99 (s, 1H, NH).

[Compound 336]
2-(3-chloro-4-fluorophenylimino)-3-methyl-4-[N-(methoxyphenyl)carbamoylmethyl]-1,3-thiazol-4-ine ($R_1$=4-OCH$_3$, $R_2$=3-Br, $R_3$=CH$_3$).
Yield: 73% Melting point: 165–166° C. $^1$H NMR (CDCl$_3$) δ 3.77 (s, 3H, 3-CH$_3$), 3.82 (s, 3H, OCH$_3$), 4.33 (s, 2H, 4-CH$_2$), 6.78~7.65 (m, 7H, ArH), 10.99 (s, 1H, NH).

[Compound 337]
2-(3-fluorophenylimino)-3-methyl-4-[N-(methoxyphenyl) carbamoylmethyl]-1,3-thiazol-4-ine ($R_1$=4-OCH$_3$, $R_2$=3-F, $R_3$=CH$_3$).
Yield: 72% Melting point: 182–184° C. $^1$H NMR (CDCl$_3$) δ 3.46 (s, 3H, 3-CH$_3$), 3.61 (s, 2H, 4-CH$_2$), 3.82 (s, 3H, 4-OCH$_3$), 5.93 (s, 1H, 5-vinyl H), 6.76~7.42 (m, 8H, ArH), 10.49 (s, 1H, NH).

[Compound 338]
2-(2-fluorophenylimino)-3-methyl-4-[N-(methoxyphenyl) carbamoylmethyl]-1,3-thiazol-4-ine ($R_1$=4-OCH$_3$, $R_2$=3-F, $R_3$=CH$_3$).
Yield: 69% Melting point: 183–185° C. $^1$H NMR (CDCl$_3$) δ 3.50 (s, 3H, 3-CH$_3$), 3.61 (s, 2H, 4-CH$_2$), 3.82 9s, 3H, 4-OCH$_3$), 5.94 (s, 1H, 5-vinyl H), 6.89~7.42 (m, 8H, ArH), 10.44 (s, 1H, NH).

[Compound 339]
2-(3-trifluoromethoxyphenylimino)-3-methyl-4-[N-methoxyphenyl)carbamoylmethyl]-1,3-thiazol-4-ine ($R_1$=4-OCH$_3$, $R_2$=3-OCF$_3$, $R_3$=CH$_3$).
Yield: 74% Melting point: 180–183° C. $^1$H NMR (CDCl$_3$) δ 43.48 (s, 3H, 3-CH$_3$), 3.61 (s, 2H, 4-CH$_2$), 3.82 (s, 3H, 4-OCH$_3$), 5.95 (s, 1H, 5-vinyl H), 6.88~7.60 (m, 8H, ArH), 10.71 (s, 1H, NH).

[Compound 340]
2-(2,4-difluorophenylimino)-3-methyl-4-[N-(methoxyphenyl)carbamoylmethyl]-1,3-thiazol-4-ine ($R_1$=4-OCH$_3$, $R_2$=2,4-F$_2$, $R_3$=CH$_3$).
Yield: 74% Melting point: 200–202° C. $^1$H NMR (CDCl$_3$) δ 3.49 (s, 3H, 3-CH$_3$), 3.60 (s, 2H, 4-CH$_2$), 3.82 (s, 3H, 4-OCH$_3$), 5.95 (s, 1H, 5-vinyl H), 6.86~7.42 (m, 8H, ArH), (s, 1H, NH).

[Compound 341]
2-(4-cyanophenylimino)-3-methyl-4-[N-(4-ethylphenyl) carbamoylmethyl]-1,3-thiazol-4-ine hydrochloride (R1=4-CH$_2$CH$_3$, $R_2$=4-CN, HX=HCl)
Yield: 52% Melting point: 226~229° C. $^1$H NMR (DMSO-d$_6$), δ 1.12~1.17 (t, 3H, J=7.6 Hz CH$_2$CH$_3$), 2.50~2.56 (q, 2H, J=7.6Hz CH$_2$CH$_3$), 3.69 (s, 3H, 3-CH$_3$), 3.97 (s, 2H, 4-CH$_2$), 6.89 (s, 1H, 5-vinyl H), 7.20~7.92 (m, 8H, ArH), 10.51 (s, 1H, NH); FT-IR (KBr) 3448, 1655, 1603, 1560, 1544.

[Compound 342]
2-(4-chloro-5-isopropoxy-2-fluorophenylimino)-3-methyl-4-[N-(4-methylphenyl)carbamoylmethyl-1,3-thiazol-4-ine hydrochloride ($R_1$=4-CH$_3$, $R_2$=4-Cl, 2-F, 5-OCH(CH$_3$)$_2$, HX=HCl).
Yield: 39% Melting point: 194.7~198.2° C. $^1$H NMR (DMSO-d$_6$+CDCl$_3$=1:2) δ 1.37 (d, 6H, OCH(CH$_3$)$_2$), 2.31 (s, 3H, CH$_3$), 4.01 (s, 3H, 3-CH$_3$), 4.07 (s, 2H, 4-CH$_2$), 4.52~4.56 (m, 1H, OCH(CH$_3$)$_2$), 7.08 (s, 1H, 5-vinyl H), 7.10~7.85 (m, 6H, ArH), 10.64 (s, 1H, NH); FT-IR (KBr) 3404, 1676, 1586.

[Compound 343]
2-(4-trifluoromethylphenylimino)-3-methyl-4-[N-(3-fluoro-4-methoxyphenyl)carbamoylmethyl]-1,3-thiazol-4-ine hydrochloride (R1=3-F, 4-OCH$_3$, $R_2$=4-CF$_3$, HX=HCl).
Yield: 23% Melting point: 228° C. $^1$H NMR (DMSO-d$_6$), δ 3.70 (s, 3H, 3-CH$_3$), 3.80 (s, 2H, 4-CH$_2$), 3.98 (s, 3H, 4-OCH$_3$), 6.92 (s, 1H, 5-vinyl H), 7.11~7.86 (m, 7H, ArH), 10.68 (s, 1H, NH); FT-IR (KBr) 3426, 1654, 1562, 1515.

[Compound 344]
2-(4-cyanophenylimino)-3-methyl-4-[N-(3-fluoro-4-methoxyphenyl)carbamoylmethyl]-1,3-thiazol-4-ine hydrochloride (R1=3-F, 4-OCH$_3$, $R_2$=4-CN, HX=HCl).
Yield: 23% Melting point: 233–234 C. $^1$H NMR (DMSO-d$_6$), δ 3.73 (s, 3H, 3-CH$_3$), 3.80 (s, 2H, 4-CH$_2$), 4.00 (s, 3H, 4-OCH$_3$), 7.00 (s, 1H, 5-vinyl H), 7.10~7.94 (m, 7H, ArH), 10.81 (s, 1H, NH); FT-IR (KBr) 3422, 1648, 1601, 1562, 1508.

[Compound 345]

2-(4-cyanophenylimino)-3-methyl-4-[N-(4-ethylphenyl) carbamoylmethyl]-1,3-thiazol-4-ine hydrochloride (R1=4-CH$_2$CH$_3$, R$_2$=4-CN, HX=HCl).

Yield: 81% Melting point: 243° C. $^1$H NMR (DMSO-d$_6$), δ 1.12~1.17 (t, 3H, J=7.6Hz CH$_2$CH$_3$), 2.49~2.56 (q, 2H, J=7.6Hz CH$_2$CH$_3$), 3.38 (s, 3H, 3-CH$_3$), 3.75 (s, 2H, 4-CH$_2$), 6.89 (s, 1H, 5-vinyl H), 7.14~7.91 (m, 8H, ArH), 10.51 (s, 1H, NH); FT-IR (KBr) 3448, 2216, 1656, 1562.

[Compound 346]

2-(4-trifluoromethylphenylimino)-3-methyl-4-[N-(4-ethylphenyl)carbamoylmethyl]-1,3-thiazol-4-ine hydrochloride (R1=4-CH$_2$CH$_3$, R$_2$=4-OCH$_3$, HX=HCl).

Yield: 67% Melting point: 258~260° C. $^1$H NMR (DMSO-d$_8$), δ 1.12~1.17 (t, 3H, J=7.6Hz CH$_2$CH$_3$), 2.51~2.56 (q, 2H, J=7.6Hz CH$_2$CH$_3$), 3.81 (s, 3H, 3-CH$_3$), 4.05 (s, 2H, 4-CH$_2$), 7.06 (s, 1H, 5-vinyl H), 7.13~7.68 (m, 8H, ArH), 10.72 (s, 1H, NH); FT-IR (KBr) 3424, 1656, 1613, 1577, 1541, 1506.

Controlling Mechanism of the Compound of the Present Invention for the Treatment of Rice Blast When the spore of rice blast fungi (*Magnaporthe grisea, Pyricularia grisea* etc.) arrives the surface of the host plant, appressorium is formed after the germination of the spores. Melanin pigment accumulates between the cell membrane and cell wall of appressorium. This pigment plays an important role in maintaining the high pressure necessary for the invading hydra to pass through the host cell wall. If melanin cannot be accumulated by suppressing the biosynthesis of melanin pigment, rice blast cannot invade the host. Therefore, the biosynthesis process of melanin is an important target site of the fungicide to prevent rice blast, and many fungicides have been developed by using this action mechanism.

The melanin pigment produced from *Magnaporthe grisea* is 1,8-dihydroxynaphthalene (1,8-DHN) melanin whose biosynthesis path is shown in FIG. 1. Melanin is produced by the following mechanism. First 1,3,6,8-THN is synthesized through Pentaketide synthesis and cyclization. 1,8-DHN is synthesized after two repetitive reduce and dehydration reactions of 1,3,6,8-THN. Finally melanin is synthesized by oxidation of 1,8-DHN. Among many melanin biosynthesis inhibitors (MBI) developed up to date, most of the MBIs except carpropamid prevent reduction process. Carpropamids inhibit the dehydration step to prevent the invasion of rice blast into the host plant. These MBIs have little effect on the growth of the microorganisms and low toxicity due to the specificity to the related enzymes and therefore are considered to be environmentally friendly fungicides. Up to now, MBIs that prevent the synthesis and cyclization of pentaketide in the melanin biosynthesis process have not been developed.

The 2-imino-1,3-thiazoline compounds of the present invention effectively prevent rice blast confirmed by the in vivo screening experiment. Also these compounds are shown to inhibit the biosynthesis of melanin confirmed by target assay. The present inventors have selected compound 5 (test code KSC35421) of the present invention and verified the characteristics and the target site during melanin biosynthesis.

In other words, spore germination of rice blast fungi, formation of the appressorium and the effect of the accumulation of melanin pigment in the appressorium were investigated. As shown in Table 2, compound 5 of the present invention inhibited the accumulation of melanin in the appressorium at the concentration above 10 μg/ml. At the concentration lower than 10 μg/ml, the compound had a negligible effect on spore germination and the formation of appressorium, but prevent almost completely the spore germination and the formation of appressorium above 100 μg/ml. Since the concentration that prevents spore germination and the formation of appressorium is far above the concentration inhibiting the biosynthesis of melanin, however, compound 5 is an MBI.

TABLE 2

Effect of concentrations of KSC35421 on spore germination of rice blast fungi, formation of appressorium and accumulation of melanin inside the appressorium

| Compound 5 (μg/ml) | Spore Germination (%)[b] | Formation of Appressorium (%)[c] | Accumulation of Melanin in Appressorium |
|---|---|---|---|
| 0 | 94 ± 5.2 | 74 ± 4.3 | + |
| 0.1 | 94 ± 3.4 | 84 ± 5.2 | − |
| 1 | 89 ± 2.3 | 79 ± 2.4 | − |
| 10 | 79 ± 1.3 | 57 ± 1.4 | − |
| 100 | 17 ± 2.0 | 9.0 ± 1.2 | − |

Figure 2:
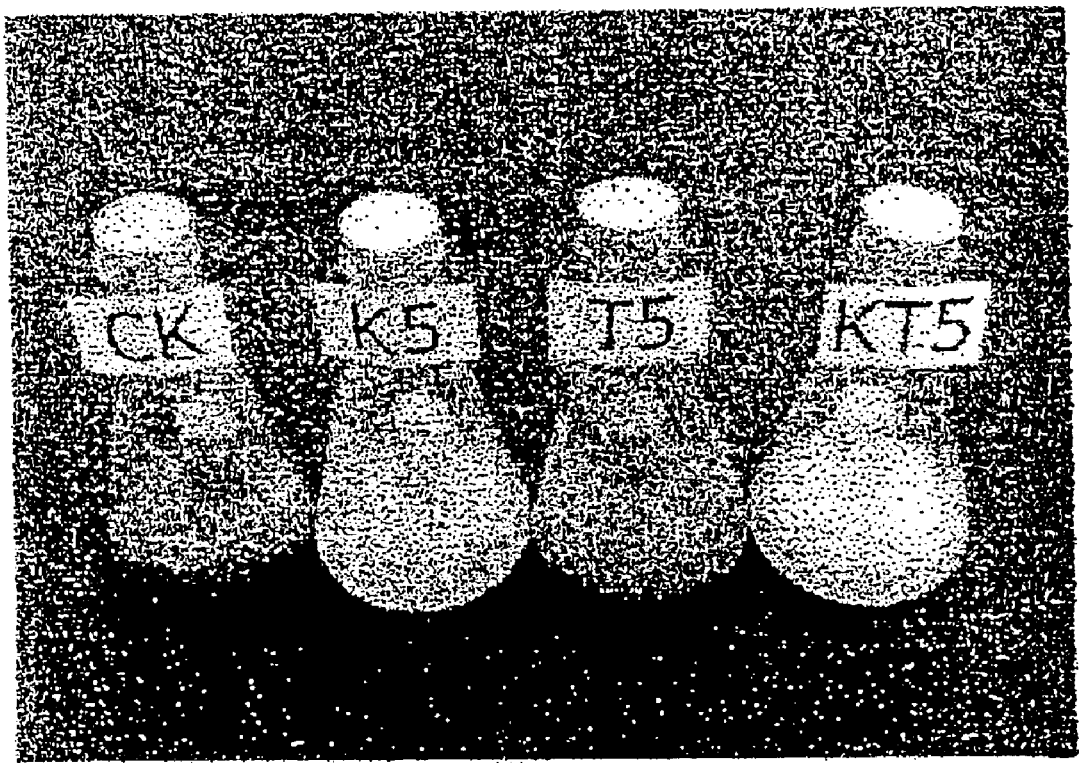
FIG. 2 is a graph to confirm the target site of the compound of the present invention related to melanin synthesis in preventing *Magnaporthe grisea* using the compound of Example 5 according to the present invention (CK-no treatment control group; K5 test group treated with compound 5 of the present invention; T5 test group treated with tricyclazole; KT5 test group treated with compound 5 of the present invention and tricyclazole).

To investigate in which step compound 5 inhibits the biosynthesis of melanin, the medium inoculated with rice blast fungi was treated with compound 5 (5 μg/ml) of the present invention, tricyclazole (5 μg/ml) and the mixture of compound 5 of the present invention and tricyclazole or not treated to record the color change in the medium (FIG. 2). As shown in FIG. 2, the color of the medium became red in case of the tricyclazole treated group (T5) acting by inhibiting the reducing step. In case of the no treatment group, the medium turned black since melanin synthesis was not inhibited. On the other hand, the color of the medium was white for the group treated with compound 5 (5 μg/ml) of the present invention and with the mixture of compound 5 of the present invention and tricyclazole. Therefore, it can be confirmed that the target site of compound 5 of the present invention is an upper stream step of the reducing step, which can be inhibited by tricyclazole. In other words, the target site of compound 5 of the present invention is the pentaketide synthesis and cyclization step, which is a step before the synthesis of 1,3,6,8-THN.

Method of Biological Activity Test

The antimicrobial activity of the compounds of the present invention was measured at the Agricultural Chemical Activity Research Center in Korea Research Institute of Chemical Technology (Taejon, Korea). The results are shown in Tables 3 and 4.

(1) Preparation of the Compound Treatment Solution

After the compounds of the present invention were dissolved in dimethylsulfoxide (DMSO), 250 μg/ml tween 20 solution was used to dilute the solution to 250 μg/ml, 100 μg/ml, 10 μg/ml and 2 μg/ml. The concentration of DMSO in the final treatment solution was controlled to be 1%. After side-spraying 2.5 ml of the compound solution per pot, they were wind-dried in a warm room for 1 day.

(2) Evaluation of the Effect of the Compound against Rice Blast (RCB)

Storage of the Pathogen

After cultivating *Pyricularia grisea*, a rice at 25° C. in potato dextrose agar (PDA) for 5 days, a piece of hypha was detached from the fungus. The piece of hypha was stored in 6% DMSO solution at −70° C. for a prolonged storage. For the evaluation test of the compound, the stored hypha pieces were inoculated in new PDA and cultivated at 25° C. The piece of hypha was detached from the fungi cultivated for 5 days, transplanted PDA clivus medium and cultivated further under identical conditions. The pathogen was stored at 4° C. for further experiments.

Preparation of the Plant

The Nakdong rice species sensitive to rice blast was planted in water for 3 days at 25° C., and three leaves were planted in each pots (diameter; 5 cm, height; 4.5 cm) in rich soil. The rice was cultivated in a glass green house until trilobate period and used to evaluate the compounds of the present invention.

Treatment of the Compound Solution

The rice leaves in trilobate period were sprayed with 2.5 ml of the solution per pot and dried by wind for one day in the green house.

(3) Preparation and Inoculation of the Pathogen

*Pyricuraria grisea* was inoculated in the rice bran agar medium (Rice Polish; 20 g, dextrose; 10 g, agar; 12 g, distilled water; 1 L) and cultivated for 2 weeks at 25° C. After removing the hypha formed on the surface, it was stored for 48 hours in a cultivating chamber (light/dark; 12 hr/12 hr) to induce the formation of spore. The formed conidiopore was harvested by using the sterile distilled water, the concentration of the spore in the suspension was controlled to $1 \times 10^6$/ml. After enough amount of the suspension was sprayed for inoculation on the rice treated with the compound, the rice was stored in a humidity chamber (absolute humidity; >95%) for 1 day. The humidity treated rice was transferred into a chamber with a controlled temperature and humidity at 26° C. (absolute humidity; 80%) to induce the disease. The area of the lesion formed on trilobate was measured in 5 days. The effect of the compound in preventing rice blast was evaluated by using the below equation.

$$\text{Inbition Number} = \frac{\text{Area of lesion in no treatment group}(\%) - \text{Area of lesion in treatment group}(\%)}{\text{Area of lesion in no treatment group}(\%)} \times 100$$

(4) Test in Adult Organisms

The Nakdong rice species sensitive to rice blast was used. Seedling of trilobate period was transplanted on Wagner pot of 1/5000a and cultivated until heading period. The rice of heading stage was treated with 20 μg/ml of the aforementioned compound of 250 ppm and air-dried in a greenhouse for 1 day. The spore suspension of rice blast fungi (spore concentration; $1 \times 10^6$/ml) was spray-inoculated on rice leaves and stored in a vinyl chamber prepared in the greenhouse to induce rice blast. One week after the inoculation, the area (%) of the disease lesion occurred on adult organisms was investigated and the effect of disease control was determined in the same manner as in the above manner to investigate the activity of the compounds. The results are shown in Table 3.

TABLE 3

| Compound No. | Inhibiting Ratio (%) (at 250 ppm) |
|---|---|
| 1 | 75 |
| 2 | 86 |
| 3 | 95 |
| 4 | 83 |
| 5 | 100 |
| 6 | 99 |
| 7 | 97 |
| 8 | 90 |
| 13 | 99 |
| 14 | 99 |
| 15 | 91 |
| 16 | 100 |
| 18 | 93 |
| 19 | 91 |
| 20 | 91 |
| 21 | 88 |
| 22 | 97 |
| 23 | 96 |
| 24 | 97 |
| 25 | 100 |
| 26 | 100 |
| 27 | 98 |
| 28 | 100 |
| 29 | 100 |
| 30 | 100 |
| 31 | 100 |
| 32 | 100 |
| 33 | 100 |
| 34 | 100 |
| 35 | 100 |
| 36 | 98 |
| 37 | 100 |
| 39 | 99 |
| 42 | 100 |
| 43 | 93 |
| 44 | 95 |
| 45 | 93 |
| 46 | 100 |
| 47 | 100 |
| 48 | 100 |
| 49 | 100 |
| 50 | 100 |
| 51 | 99 |
| 52 | 99 |
| 53 | 99 |
| 54 | 96 |
| 55 | 96 |
| 56 | 96 |
| 57 | 96 |
| 58 | 96 |
| 59 | 96 |
| 60 | 100 |
| 61 | 100 |
| 62 | 100 |
| 63 | 96 |
| 65 | 98 |
| 66 | 96 |
| 67 | 100 |
| 68 | 95 |
| 69 | 96 |
| 70 | 96 |
| 78 | 91 |
| 79 | 90 |
| 89 | 83 |
| 90 | 91 |
| 98 | 96 |
| 102 | 93 |
| 104 | 93 |
| 105 | 90 |
| 108 | 91 |
| 118 | 99 |
| 124 | 93 |
| 128 | 98 |
| 129 | 96 |
| 130 | 98 |
| 131 | 96 |
| 132 | 99 |
| 133 | 99 |
| 134 | 98 |
| 135 | 98 |
| 136 | 97 |
| 137 | 97 |
| 138 | 95 |

TABLE 3-continued

| Compound No. | Inhibiting Ratio (%) (at 250 ppm) |
|---|---|
| 139 | 99 |
| 140 | 99 |
| 141 | 99 |
| 142 | 98 |
| 143 | 95 |
| 144 | 97 |
| 147 | 96 |
| 148 | 95 |
| 149 | 95 |
| 150 | 96 |
| 151 | 96 |
| 152 | 100 |
| 153 | 99 |
| 154 | 93 |
| 155 | 96 |
| 156 | 96 |
| 158 | 90 |
| 159 | 92 |
| 160 | 88 |
| 161 | 86 |
| 162 | 89 |
| 167 | 88 |
| 168 | 92 |
| 176 | 96 |
| 185 | 97 |
| 192 | 92 |
| 196 | 92 |
| 197 | 95 |
| 198 | 95 |
| 201 | 97 |
| 202 | 95 |
| 203 | 93 |
| 204 | 97 |
| 205 | 97 |
| 206 | 93 |
| 207 | 93 |
| 208 | 97 |
| 209 | 97 |
| 215 | 93 |
| 221 | 87 |
| 226 | 92 |
| 227 | 97 |
| 228 | 97 |
| 229 | 93 |
| 230 | 93 |
| 231 | 93 |
| 232 | 92 |
| 233 | 97 |
| 234 | 97 |
| 235 | 92 |
| 236 | 97 |
| 238 | 93 |
| 239 | 92 |
| 240 | 88 |
| 257 | 88 |
| 258 | 91 |
| 263 | 96 |
| 303 | 100 |
| 304 | 100 |
| 305 | 100 |
| 306 | 93 |
| 307 | 100 |
| 308 | 99 |
| 309 | 100 |
| 310 | 100 |
| 311 | 95 |
| 312 | 25 |
| 313 | 100 |
| 314 | 100 |
| 315 | 97 |
| 316 | 100 |
| 317 | 100 |
| 318 | 100 |
| 319 | 100 |
| 320 | 100 |
| 321 | 97 |
| 323 | 97 |
| 323 | 97 |
| 324 | 90 |
| 325 | 97 |
| 326 | 97 |
| 327 | 62 |
| 328 | 97 |
| 329 | 100 |
| 330 | 100 |
| 331 | 96 |
| 332 | 100 |
| 333 | 98 |
| 334 | 96 |
| 335 | 99 |
| 336 | 96 |
| 337 | 95 |
| 338 | 97 |
| 339 | 98 |
| 340 | 94 |

Further, Table 4 summarizes the results of the pest control activity on rice blast of the twenty compounds among the above compounds, which show particularly excellent controlling effect at the concentrations of 100 ppm, 10 ppm, and 2 ppm. As noted from the following Table 4, the compounds wherein each of $R_1$ and $R_2$ represent methyl, ethyl, methoxy, isopropoxy, fluoro, chloro, bromo, trifluormethyl, trifluoromethoxy, isopropoxy, fluoro, chloro, bromo, trifluoromethyl, trifluoromethoxy, or cyano and $R_3$ is methyl, particularly, the compounds wherein $R_1$ represents p-methyl, p-methoxy, or p-ethyl and $R_2$ is p-cyano or p-fluoro, methyl, methoxy, etc. show excellent controlling effect on rice blast as they shows controlling effect of at least 90% at 10 ppm, and at least 70% at the concentration of as low as 2 ppm.

TABLE 4

| No. | $R_1$ | $R_2$ | $R_3$ | X | 100 ppm | 10 ppm | 2 ppm |
|---|---|---|---|---|---|---|---|
| 341 | $CH_2CONHC_6H_4(4-CH_2CH_3)$ | $N—C_6H_4(4-CN)$ | $CH_3$ | HCl | 93 | 98 | 96 |
| 202 | $CH_2CONHC_6H_4(4-OCH_3)$ | $N—C_6H_3(3-Cl, 4-F)$ | $CH_3$ | HCl | 95 | 98 | 93 |
| 203 | $CH_2CONHC_6H_4(4-OCH_3)$ | $N—C_6H_4(3-F)$ | $CH_3$ | HCl | 93 | 99 | 93 |
| 205 | $CH_2CONHC_6H_4(4-OCH_3)$ | $N—C_6H_4(4-CF_3)$ | $CH_3$ | HCl | 97 | 98 | 93 |
| 206 | $CH_2CONHC_6H_4(4-OCH_3)$ | $N—C_6H_3(2,4-F_2)$ | $CH_3$ | HCl | 93 | 97 | 93 |
| 342 | $CH_2CONHC_6H_4(4-CH_3)$ | $N—C_6H_2(4-Cl, 2-F, 5-OCH(CH_3)_2)$ | $CH_3$ | HCl | 92 | 98 | 90 |
| 343 | $CH_2CONHC_6H_3(3-F, 4-OCH_3)$ | $N—C_6H_4(4-CF_3)$ | $CH_3$ | HCl | 98 | 94 | 90 |
| 201 | $CH_2CONHC_6H_4(4-OCH_3)$ | $N—C_6H_4(3-Br)$ | $CH_3$ | HCl | 97 | 99 | 87 |

TABLE 4-continued

| No. | R₁ | R₂ | R₃ | X | 100 ppm | 10 ppm | 2 ppm |
|---|---|---|---|---|---|---|---|
| 128 | $CH_2CONHC_6H_4$(4-Cl) | $N{-}C_6H_4$(4-CN) | $CH_3$ | HBr | 100 | 100 | 85 |
| 197 | $CH_2CONHC_6H_4$(4-$OCH_3$) | $N{-}C_6H_4$(4-$(CH_2)_3CH_3$) | $CH_3$ | HCl | 95 | 98 | 83 |
| 204 | $CH_2CONHC_6H_4$(4-$OCH_3$) | $N{-}C_6H_4$(2-F) | $CH_3$ | HCl | 97 | 95 | 83 |
| 344 | $CH_2CONHC_6H_3$(3-F, 4-$OCH_3$) | $N{-}C_6H_4$(4-CN) | $CH_3$ | HCl | 98 | 97 | 83 |
| 339 | $CH_2CONHC_6H_4$(4-$OCH_3$) | $N{-}C_6H_4$(4-$CF_3$) | $CH_3$ | Free | 96 | 95 | 80 |
| 27 | $CH_2CONHC_6H_5$ | $N{-}C_6H_3$(2,4-$F_2$) | $CH_3$ | HBr | 98 | 91 | 80 |
| 31 | $CH_2CONHC_6H_4$(4-$CH_3$) | $N{-}C_6H_3$(2,4-$F_2$) | $CH_3$ | HBr | 100 | 91 | 80 |
| 234 | $CH_2CONHC_6H_3$(3-Cl, 4-$CH_3$) | $N{-}C_6H_4$(4-$(CH_2)_3CH_3$) | $CH_3$ | HCl | 97 | 92 | 75 |
| 323 | $CH_2CONHC_6H_4$(4-$OCH_3$) | $N{-}C_6H_4$(4-CN) | $CH_3$ | HBr | 100 | 100 | 75 |
| 335 | $CH_2CONHC_6H_4$(4-$OCH_3$) | $N{-}C_6H_3$(3-Br) | $CH_3$ | Free | 94 | 95 | 72 |
| 152 | $CH_2CONHC_6H_4$(2-F) | $N{-}C_6H_4$(4-Br) | $CH_3$ | HCl | 99 | 85 | 70 |
| 345 | $CH_2CONHC_6H_4$(4-$CH_2CH_3$) | $N{-}C_6H_4$(4-CN) | $CH_3$ | Free | 97 | 94 | 70 |
| 346 | $CH_2CONHC_6H_4$(4-$CH_2CH_3$) | $N{-}C_6H_4$(4-$OCF_3$) | $CH_3$ | HCl | 99 | 96 | 79 |

Toxicity Test

To establish the toxicity of the present invention, three kinds of toxicity tests, bacterial reverse mutation assay in *Salmonella typhimurium*, acute toxicity test in fish andsingle dose oral toxicity test in rat were performed for the representative compound 204. Safety Research Center in Korea Advanced Institute of Science and Technology were commissioned to perform the toxicity tests. The test protocols were as follows.

(1) Bacterial Reverse Mutation Assay
1. Test material: compound 204(KHG 21864: white powder with 99.8% purity, lot number not allocated)
2. Code number in the Testing Organization: K-1209
3. Test number: N 0 0 0 3 5
4. Testing organization: Korea Advanced Institute of Science and Technology
5. Test protocol and results
   (1) Test cell line: *Salmonella typhimurium* TA100 and TA98.
   (2) Concentration of the test material: 19.6~5000 μg/plate (common ratio 2, solubilized in DMSO)
   (3) Determination of the concentration: The highest concentration was set to 5000 μg/plate according to the Toxicity Test Standards of Medical Supplies.
   (4) Test protocol: The protocol followed the method by Maron & Ames(1 983).
   (5) Decision of the result: The result of the test was decided as follows. The result was decided positive when the colony number of the bacterial reverse mutation assay was dependent on the concentration of the test material and increased by more than twice. It was decided negative when the colony number of the bacterial reverse mutation assay in the test group was less than twice of the colony number in the negative control group.
   (6) Results: The colony number in the group treated with the test material was less than twice of that in the negative control group. The colony number decreased slightly in the group treated with the highest concentration, but it was not enough to be considered antimicrobial. There are no noticeable observations except that an insoluble suspension was formed when the solution containing the test material at 156.3 μg/plate was mixed with top agar.
6. Conclusion: Compound 204 of the present invention does not cause bacterial reverse mutation in the bacterial cell lines TA100 and TA98 under the present experimental conditions.

(2) Acute Toxicity Test in Fish
Test Number: EN00011—compound 204 (Acute toxicity test in Fish of KHG 21864)

1. Test material
   (1) Name: compound 204 (KHG 21864, (K-1209)
   (2) Purity: 99.8%
   (3) Storage conditions: refrigerated
2. Test protocol
   (1) Test Organism and Cultivation Protocol
   *Oryzias latipes* used in the toxicity test was cultivated for approximately 10 months in the fish breeding room. The body length and weight of the group treated with 0.1 mg/L of the test material were measured after the experiment and represented as the average and standard deviation.
   body length: 3.2±0.1 cm
   body weight: 0.30±0.05 g
   The breeding water was the underground water that passed through a membrane filter (1 μm) and an activated carbon filtration unit. *Oryzias latipes* used in the toxicity test was cultivated at the water temperature of 23~26° C., 16 hours of light and 8 hours of dark cycles. The fish were fed with larvae of brine shrimp (GOLDEN WEST ARTEMIA, USA) in the morning and with Tetramine flake (Tetra®, Germany) in the afternoon.
   (2) Adaptation and Fasting
   *Oryzias latipes* used in the experiment underwent adaptation period under identical environmental conditions as that of the toxicity test. The fish were fasted for 24 hours before the initiation of the test. The occurrence of the dead fish and the water temperature during the adaptation and fasting period were recorded. There was no dead fish during the adaptation and fasting period. The health condition of the fish was satisfactory, and the water temperature was 23.8~24.0° C.
   (3) Experimental conditions
   1) Diluent
   The diluent used in the experiment was the breeding water that passed through a membrane filter (1 μm) and an activated carbon filtration unit.
   2) Light Cycle
   The light cycle was controlled with a lamp to be a 16 hours of light and 8 hours of dark cycle.
   3) Food and Air Supply
   Food and air were not supplied during the test period.
   (4) Exposure Concentration and Method
   The toxicity test was carried out at 0.1, 1, 10, 100 mg/L. Static method that the test solution was not exchanged during the test period was used.
   (5) Preparation of the Test Solution
   The stock solution at a concentration of 50,000 mg/L was prepared by adding 251 mg of the test material one drop of HCO-40 and Dimethyl Sulfoxide (DMSO, Merck, Germany) to the mark of a 5 mL volumetric flask. Equal amounts of the stock solution were added to a diluent to prepare test solutions with different concentrations.

(6) Administration of *Oryzias latipes*

After preparing the test solutions, 5 *Oryzias latipes* were put in the solution at random without repetition. The initiation of the test was set to the time point of Administration of *Oryzias latipes*.

(7) Observation and Recording

The occurrence of dead fish and toxicological symptoms were observed and recorded every day during the test period. The fish were considered dead if there is no reaction upon touching caudal peduncle and if the branchial respiration stops. The dead fish was eliminated from the test container immediately after discovery. During the test period, pH, dissolved oxygen (DO), water temperature of the test solution was measured and recorded before and after the experiment at the lowest and highest concentrations.

3. Results (1) The Water Quality and the Condition of the Test Material

During the test period, the water temperature was 24.5~25.0° C., dissolved oxygen concentration was 5.1~8.4 mg/L, and pH was 7.23~7.86. The test material in the water chamber was slightly turbid at the concentrations of 10 and 100 mg/L with the formation of the oil film at the surface. At 10 mg/L, small amount of precipitation was formed after 24 hours. Large quantity of precipitation was formed immediately after adding the test material is 100 mg/L.

(2) Toxicity

During the test period, there was no dead fish or fish showing toxicological symptoms in the concentration range studied. The running lethality with different exposure times is shown in Table 5.

TABLE 5

| Treatment | Number of | Accumulated number of dead animals | |
|---|---|---|---|
| Conc. (mg/L) | treated animals | 24 hr | 48 hr |
| 0.1 | 5 | 0 | 0 |
| 1 | 5 | 0 | 0 |
| 10 | 5 | 0 | 0 |
| 100 | 5 | 0 | 0 |

4. Summary

According to the test result, the acute toxicity value of compound 204 in *Oryzias latipes* is estimated to >100 mg/L (standardized by the established concentration)

(3) Single Dose Oral Toxicity Test in Rats

Test number: N00034

Title of the test: single dose oral toxicity test of compound 204 KHG21864) in rats Test client: Korea Institute of Science and Technology Ho Gyu Han material 1. Test material (1) Name of the test material: compound 204 (KHG21864: K-1209)

(2) Solvent: 0.5% Tween 80

2. Test system (1) Species and system of the animals: Specific Pathogen Free (SPF) Sprague-Dawley rats (2) Age of the animals: 4-week old when obtained, 5-week old at the beginning of the administration (3) Sex and number of the animals: 15 each of male and female rats (5 groups each for male and female rats, 3 rats for each group)

(4) Breeding condition: Temperature 22±3° C., Relative humidity 50±10%, Illumination 150~300 Lux 3. Number and method of administration: Single dose oral administration 4. Administration Dosage: Since the toxicological information of the test material of the present invention is not available, the highest concentration was set to the limiting test dosage of 2500 mg/kg in solid agricultural chemicals by the Guideline of Korean Rural Development Organization. Four low concentration groups were added by setting the dilution fold to 3.

5. Observation Items: observation of general symptoms and dead animals (up to 7 days after administration), body weight, postmortem examination report 6. Results (1) Dead Animals and Lethal Dose Dead dead animals were not observed during 7 days after administering the test material caused by the test material in either male or females rats. Therefore, the minimal lethal dose of the test material of the present invention in rats is considered to be higher than 2500 mg/kg.

(2) General Symptoms

Any abnormal observations were made using the test period caused by the test materials.

(3) Body Weight

Normal weight gain was observed in both the groups of male and female rats.

(4) Postmortem Examination

Postmortem examination does not show any abnormal conservation related to the administration of the test materials.

The compound of the present invention is a safe compound without any toxicity to the environments including the crops and the users after considering the results of the above three toxicological tests.

INDUSTRIAL APPLICABILITY

Since phenyliminothiazoline compounds and their hydrogen chloride and hydrobromides represented by Formula (I) of the present invention exert high activity at low concentration for treating rice blast through a new controlling mechanism and have low toxicity to environment or living organisms, they can be used as promising fungicides even with an increasing tolerance of *Magnaporthe grisea*.

What is claimed is:

1. 2-phenyliminothiazoline derivatives and their hydrochloride and hydrobromide salt represented by Formula (I):

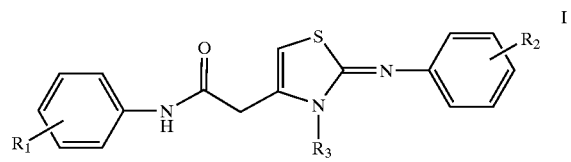

wherein, $R_1$ represents: (1) an alkyl group selected from the group consisting of methyl, ethyl, propyl, butyl, pentyl and hexyl; (2) a halide group selected from fluoro, chloro and bromo; (3) an alkoxy group selected from methoxy, ethoxy, propoxy, isopropoxy, butyl, isobutoxy and sec-butoxy: or (4) nitro, and R2 represents: (1) a hydrogen; (2) an alkyl group selected from the group consisting of methyl, ethyl, propyl, butyl, pentyl and hexyl; (3) a halide group selected from fluoro, chloro and bromo; (4) an alkoxy group selected from methoxy, ethoxy, propoxy, isopropoxy, butoxy, isobutoxy and sec-butoxy; (5) cyano, nitro, trifluoromethyl, trifluoromethoxy, methylthio, phenyl, phenoxy; or (6) an alkoxycarbonyl group selected from methoxycarbonyl, ethoxycarbonyl, propoxycarbonyl and isopropoxycarbonyl, and $R_3$ represents: (1) a hydrogen (2) an alkyl group selected from the group consisting of methyl, ethyl, propyl, isopropyl, cyclopropyl, butyl, pentyl; or (3) a cycloalkyl group selected from the group consisting of cyclopentyl, hexyl and cyclohexyl.

2. The 2-phenyliminothiazoline derivative and their hydrochloride hydrobromide salt according to claim 1, wherein $R_1$ represents methyl, ethyl methoxy, isopropoxy, fluoro, chloro or bromo, $R_2$ represents methyl, ethyl, methoxy, isopropoxy, fluoro, chloro, bromo, trifluoromethyl, trifluoromethoxy, or cyano and $R_3$ represent methyl.

3. The 2-phenyliminothiazoline derivative and their hydrochloride or hydrobromide salts according to claim 2, wherein $R_1$ is p-methyl, p-methoxy, or p-ethyl, and $R_2$ is p-cyano or p-fluoro.

4. The 2-phenyliminothiazoline derivative and their hydrochloride or hydrobromide salts according to any one of claims 1–3, selected from:

2-(4-cyanophenylimino)-3-methyl-4-[N-(4-ethylphenyl)carbamoylmethyl]-1,3-thiazol-4-ine hydrochloride, 2-(3-chloro-4-fluorophenylimino)-3-methyl-4-[N-(4-methoxyphenyl)carbamoyl methyl]-1,3-thiazol-4-ine hydrochloride, 2-(3-fluorophenylimino)-3-methyl-4-[N-(4-methoxyphenyl)carbamoylmethyl]-1,3-thiazol-4-ine hydrochloride, 2-(4-trifluoromethylphenylimino)-3methyl-4-[N-(4-ethoxyphenyl)carbamoyl methyl]-1,3-thiazol-4-ine hydrochloride, 2-(2,4-difluorophenylimino)-3-methyl-4-[N-(4-methoxyphenyl)carbamoylmethyl]-1,3-thiazol-4-ine hydrochloride, 2-(4-chloro-5-isopropoxy-2-fluorophenylimino)-3-methyl-4-[N-(4-methylphenyl) carbamoylmethyl]-1,3-thiazol-4-ine hydrochloride, 2-(4-trifluoromethylphenylimino)-3-methyl-4-[N-(3-fluoro-4-methoxyphenyl) carbamoylmethyl]-1,3-thiazol-4-ine hydrochloride, 2-(3-bromophenylimino)-3-methyl-4-[N-(4-methoxyphenyl)carbamoylmethyl]-1,3-thiazol-4-ine hydrochloride, 2-(4-cyanophenylimino)-3-methyl-4-[N-(4-chlorophenyl)carbamoylmethyl]-1,3-thiazol-4-ine hydrochloride, 2-[4-(n-butyl)phenylimino]-3-methyl-4-[N-(4-methoxyphenyl)carbamoylmethyl]-1,3-thiazol-4-ine hydrochloride, 2-(2-fluorophenylimino)-3-methyl-4-[N-(4-methoxyphenyl)carbamoylmethyl]-1,3-thiazol-4-ine hydrochloride, 2-(4-cyanophenylimino)-3-methyl-4-[N-(3-fluoro-4-methoxyphenyl)carbamoyl methyl]-1,3-thiazol-4-ine hydrochloride, 2-(3-trifluoromethoxyphenylimino)-3-methyl-4[N-(methoxyphenyl)carbamoyl methyl]-1,3-thiazol-4-ine, 2-(2,4-difluorophenylimino)-3-methyl-4-[N-(4-methylphenyl)carbamoylmethyl]-1,3-thiazol-4-ine hydrobromide, 2-[4-(n-butyl)phenylimino]-3-methyl-4-(N-[3-chloro-4-methylphenyl)carbamoyl methyl]-4-thiazoline hydrochloride, 2-(4-cyanophenylimino)-3-methy-4-[N-(4-methoxyphenyl)carbamoylmethyl]-1,3-thiazol-4-ine hydrobromide, 2-(3-bromophenylimino)-3-methyl-4-[N-(methoxyphenyl)carbamoylmethyl]-1,3-thiazol-4-ine, 2-(4-bromophenylimino)-3-methyl-4-[N-(2-fluorophenyl)carbamoylmethyl]-1,3-thiazol-4-ine hydrochloride, 2-(4-cyanophenylimino)-3-methyl-4-[N-(4-ethylphenyl)carbamoylmethyl]-1,3-thiazol-4-ine hydrochloride, and 2-(4-trifluoromethylphenylimino)-3-methyl-4-[N-(4-ethylphenyl)carbamoylmethyl]-1,3-thiazol-4-ine hydrochloride.

5. A rice blast fungicide comprising 2-phenyliminothiazoline derivatives and their hydrochloride or hydrobromide salt of claim 1 as an active ingredient.

6. A rice blast fungicide comprising 2-phenyliminothiazoline derivatives and their hydrochloride or hydrobromode salt of claim 2 as an active ingredient.

7. A rice blast fungicide comprising 2-phenyliminothiazoline derivatives and their hydrochloride or hydrobromide salt of claim 3 as an active ingredient.

8. A rice blast fungicide comprising 2-phenyliminothiazoline derivatives and their hydrochloride or hydrobromide salt of claim 4 as an active ingredient.

9. 2-phenyliminothiazoline derivatives and their hydrochloride and hydrobromide salt represented by Formula (I):

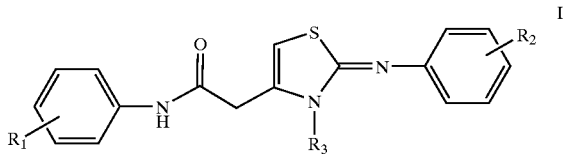

wherein $R_1$ represents: (1) an alkyl group selected from the group consisting of methyl, ethyl, propyl, butyl, pentyl and hexyl; (2) a halide group selected from fluoro, chloro and bromo; (3) an alkoxy group selected from methoxy, ethoxy, propoxy, isopropoxy, butyl, isobutoxy and sec-butoxy; or 4) cyano, nitro, trifluoromethyl, trifluoromethoxy, methylthio, phenyl, phenoxy, or an alkoxycarbonyl group selected from methoxycarbonyl, ethoxycarbonyl, propoxycarbonyl and isopropoxycarbonyl, and R2 represents: (1) a hydrogen; (2) an alkyl group selected from the group consisting of methyl, ethyl, propyl, butyl, pentyl and hexyl; (3) a halide group selected from fluoro, chloro and bromo; (4) an alkoxy group selected from methoxy, ethoxy, propoxy, isopropoxy, butoxy, isobutoxy and sec-butoxy; (5) cyano, nitro, trifluoromethyl, trifluoromethoxy, methylthio, phenyl, phenoxy; or (6) an alkoxycarbonyl group selected from methoxycarbonyl, ethoxycarbonyl, propoxycarbonyl and isopropoxycarbonyl, and isopropoxycarbonyl, and $R_3$ represents: (1) a hydrogen; (2) an alkyl group selected from the group consisting of methyl, ethyl, propyl, isopropyl, cyclopropyl, butyl, pentyl; or (3) a cycloalkyl group selected from the group consisting of cyclopentyl, hexyl and cyclohexyl.

10. A rice blast fungicide comprising 2-phenyliminothiazoline derivatives and their hydrochloride or hydrobromide salt of claim 9 as an active ingredient.

* * * * *